(12) United States Patent
Mitsunaka et al.

(10) Patent No.: US 11,939,592 B2
(45) Date of Patent: Mar. 26, 2024

(54) HOST BACTERIUM SPECIFIC NANOPARTICLE

(71) Applicant: NATIONAL UNIVERSITY CORPORATION TOKAI NATIONAL HIGHER EDUCATION AND RESEARCH SYSTEM, Nagoya (JP)

(72) Inventors: Shoichi Mitsunaka, Gifu (JP); Hiroki Ando, Gifu (JP)

(73) Assignee: NATIONAL UNIVERSITY CORPORATION TOKAI NATIONAL HIGHER EDUCATION AND RESEARCH SYSTEM, Nagoya (JP)

( * ) Notice: Subject to any disclaimer, the term of this patent is extended or adjusted under 35 U.S.C. 154(b) by 419 days.

(21) Appl. No.: 17/275,401

(22) PCT Filed: Dec. 5, 2019

(86) PCT No.: PCT/JP2019/047649
§ 371 (c)(1),
(2) Date: Mar. 11, 2021

(87) PCT Pub. No.: WO2020/137421
PCT Pub. Date: Jul. 2, 2020

(65) Prior Publication Data
US 2022/0056474 A1 Feb. 24, 2022

(30) Foreign Application Priority Data
Dec. 27, 2018 (JP) ................. 2018-244789

(51) Int. Cl.
*C12N 15/86* (2006.01)
*A61K 35/74* (2015.01)
*C12N 1/20* (2006.01)
*C12N 7/04* (2006.01)

(52) U.S. Cl.
CPC .............. *C12N 15/86* (2013.01); *A61K 35/74* (2013.01); *C12N 1/20* (2013.01); *C12N 7/045* (2013.01)

(58) Field of Classification Search
CPC ............................................. G01N 33/54346
See application file for complete search history.

(56) References Cited

FOREIGN PATENT DOCUMENTS

| JP | 2002-541822 A | 12/2002 |
|----|---------------|---------|
| JP | 2017-525377 A | 9/2017 |
| JP | 2017-634684 A | 11/2017 |
| WO | WO 00/61804 A1 | 10/2000 |
| WO | WO 2016/033088 A1 | 3/2016 |
| WO | WO 2016/071503 A1 | 5/2016 |
| WO | WO2017/095440 | * 6/2017 |

OTHER PUBLICATIONS

Healthline (https://www.healthline.com/health/infections, accessed on Jul. 11, 2023 (Year: 2023).*
Wang et al., International Journal of Nanomedicine, 2017; 12: 1227-1249 (Year: 2017).*
Ando et al., "Engineering Modular Viral Scaffolds for Targeted Bacterial Population Editing", Cell Systems, Sep. 23, 2015, vol. 1, No. 3, pp. 187-196, Total 27 pages.
Ando, "Creation of synthetic bacterial viruses", Japanese journal of bacteriology, Nov. 29, 2018, vol. 73, No. 4, pp. 201-210.
Górski et al., "Bacteriophage therapy for the treatment of infections", Current Opinion in Investigational Drugs, Aug. 2009, vol. 10, No. 8, pp. 766-774.
International Search Report (PCT/ISA/210) issued in PCT/JP2019/047649 mdated Mar. 17, 2020.
Keen, "Phage therapy: concept to cure", Frontiers in Microbiology, Jul. 19, 2012, vol. 3, Article 238, pp. 1-3.
Written Opinion (PCT/ISA/237) issued in PCT/JP2019/047649 dated Mar. 17, 2020.
Extended European Search Report for European Application No. 19904815.8, dated Sep. 06, 2022.
Westwater et al., "Use of Genetically Engineered Phage To Deliver Antimicrobial Agents to Bacteria: an Alternative Therapy for Treatment of Bacterial Infections," Antimicrobial Agents and Chemotherapy. vol. 47, No. 4, Apr. 2003, XP002483598, pp. 1301-1307.
Chinese Office Action and Search Report for corresponding Chinese Application No. 201980059542.7, dated Aug. 30, 2023, with English translation.
Japanese Office Action for Japanese Application No. 2020-563001, dated Oct. 3, 2023, with English translation.

* cited by examiner

*Primary Examiner* — Brian Gangle
*Assistant Examiner* — Lakia J Jackson-Tongue
(74) *Attorney, Agent, or Firm* — Birch, Stewart, Kolasch & Birch, LLP

(57) ABSTRACT

An object of the present invention is to provide a recombinant phage having high safety and excellent practicality and usefulness. Provided are a recombinant bacteriophage which is deprived of its proliferative capacity and can infect only once due to the fact that a bacteriophage genome in which a part of a virion constituent gene is deleted is stored in a head, and a method for preparing the same. In addition, provided are a recombinant bacteriophage which is deprived of its proliferative capacity and can infect only once due to the fact that a plasmid having a packaging site and encoding a target gene is stored in a head, and a method for preparing the same.

12 Claims, 15 Drawing Sheets
Specification includes a Sequence Listing.

T7 WT phage genome pTOW-T7-Δtail

T7 WT phage genome pTOW-T7-Δhead

T7 WT phage genome pTOW-T7-ΔPAC site

After culture for 6 hours

SEQUENCE LISTING

<160> NUMBER OF SEQ ID NOS: 50

<210> SEQ ID NO 1
<211> LENGTH: 1197
<212> TYPE: DNA

<213> ORGANISM: Bacteriophage T7

<400> SEQUENCE: 1

| | | | | | |
|---|---|---|---|---|---:|
| atggctagca | tgactggtgg | acagcaaatg | ggtactaacc | aaggtaaagg tgtagttgct | 60 |
| gctggagata | aactggcgtt | gttcttgaag | gtatttggcg | gtgaagtcct gactgcgttc | 120 |
| gctcgtacct | ccgtgaccac | ttctcgccac | atggtacgtt | ccatctccag cggtaaatcc | 180 |
| gctcagttcc | ctgttctggg | tcgcactcag | gcagcgtatc | tggctccggg cgagaacctc | 240 |
| gacgataaac | gtaaggacat | caaacacacc | gagaaggtaa | tcaccattga cggtctcctg | 300 |
| acggctgacg | ttctgattta | tgatattgag | gacgcgatga | accactacga cgttcgctct | 360 |
| gagtatacct | ctcagttggg | tgaatctctg | gcgatggctg | cggatggtgc ggttctggct | 420 |
| gagattgccg | tctgtgtaa | cgtggaaagc | aaatataatg | agaacatcga gggcttaggt | 480 |
| actgctaccg | taattgagac | cactcagaac | aaggccgcac | ttaccgacca agttgcgctg | 540 |
| ggtaaggaga | ttattgcggc | tctgactaag | gctcgtgcgg | ctctgaccaa gaactatgtt | 600 |
| ccggctgctg | accgtgtgtt | ctactgtgac | ccagatagc | actctgcgat tctggcagca | 660 |
| ctgatgccga | acgcagcaaa | ctacgctgct | ctgattgacc | ctgagaaggg ttctatccgc | 720 |
| aacgttatgg | gctttgaggt | tgtagaagtt | ccgcacctca | ccgctggtgg tgctggtacc | 780 |
| gctcgtgagg | gcactactgg | tcagaagcac | gtcttccctg | ccaataaagg tgagggtaat | 840 |
| gtcaaggttg | ctaaggacaa | cgttatcggc | ctgttcatgc | accgctctgc ggtaggtact | 900 |
| gttaagctgc | gtgacttggc | tctggagcgc | gctcgccgtg | ctaacttcca agcggaccag | 960 |
| attatcgcta | agtacgcaat | gggccacggt | ggtcttcgcc | cagaagctgc tggtgcagtg | 1020 |
| gtttttcaaa | gtggagtaat | gctgggggtg | gcctcaacgg | tcgctgctag tcccgaagag | 1080 |
| gcgagtgtta | cttcaacaga | agaaaccta | acgccagcac | aggaggccgc acgcacccgc | 1140 |
| gctgctaaca | agcccgaaa | ggaagctgag | ttggctgctg | ccaccgctga gcaataa | 1197 |

<210> SEQ ID NO 2
<211> LENGTH: 591
<212> TYPE: DNA
<213> ORGANISM: Bacteriophage T7

<400> SEQUENCE: 2

| | | | | | |
|---|---|---|---|---|---:|
| atgcgctcat | acgatatgaa | cgttgagact | gccgctgagt | tatcagctgt gaacgacatt | 60 |
| ctggcgtcta | tcggtgaacc | tccggtatca | acgctggaag | gtgacgctaa cgcagatgca | 120 |
| gcgaacgctc | ggcgtattct | caacaagatt | aaccgacaga | ttcaatctcg tggatggacg | 180 |
| ttcaacattg | aggaaggcat | aacgctacta | cctgatgttt | actccaacct gattgtatac | 240 |
| agtgacgact | atttatccct | aatgtctact | tccggtcaat | ccatctacgt taaccgaggt | 300 |
| ggctatgtgt | atgaccgaac | gagtcaatca | gaccgctttg | actctggtat tactgtgaac | 360 |
| attattcgtc | ccgcgacta | cgatgagatg | cctgagtgct | tccgttactg gattgtcacc | 420 |
| aaggcttccc | gtcagttcaa | caaccgattc | tttggggcac | cggaagtaga gggtgtactc | 480 |
| caagaagagg | aagatgaggc | tagacgtctc | tgcatggagt | atgagatgga ctacggtggg | 540 |
| tacaatatgc | tggatggaga | tgcgttcact | tctggtctac | tgactcgcta a | 591 |

<210> SEQ ID NO 3
<211> LENGTH: 2385
<212> TYPE: DNA
<213> ORGANISM: Bacteriophage T7

<400> SEQUENCE: 3

```
atggcactca ttagccaatc aatcaagaac ttgaagggtg gtatcagcca acagcctgac    60
atccttcgtt atccagacca agggtcacgc caagttaacg gttggtcttc ggagaccgag   120
ggcctccaaa agcgtccacc tcttgttttc ttaaatacac ttggagacaa cggtgcgtta   180
ggtcaagctc cgtacatcca cctgattaac cgagatgagc acgaacagta ttacgctgtg   240
ttcactggta gcggaatccg agtgttcgac cttcctggta acgagaagca agttaggtat   300
cctaacggtt ccaactacat caagaccgct aatccacgta acgacctgcg aatggttact   360
gtagcagact atacgttcat cgttaaccgt aacgttgttg cacagaagaa cacaaagtct   420
gtcaacttac cgaattacaa ccctaatcaa gacggattga ttaacgttcg tggtggtcag   480
tatggtaggg aactaattgt acacattaac ggtaaagacg ttgcgaagta aagatacca   540 gatggtagtc aacctgaaca cgtaaacaat acggatgccc aatggttagc tgaagagtta   600
gccaagcaga tgcgcactaa cttgtctgat ggactgtaa atgtagggca agggttcatc   660
catgtgaccg cacctagtgg tcaacagatt gactccttca cgactaaaga tggctacgca   720
gaccagttga ttaaccctgt gacccactac gctcagtcgt tctctaagct gccacctaat   780
gctcctaacg gctacatggt gaaaatcgta ggggacgcct ctaagtctgc cgaccagtat   840
tacgttcggt atgacgctga gcggaaagtt tggactgaga ctttaggttg gaacactgag   900
gaccaagttc tatgggaaac catgccacac gctcttgtgc gagccgctga cggtaatttc   960
gacttcaagt ggcttgagtg gtctcctaag tcttgtggtg acgttgacac caaccccttgg  1020 ccttcttttg ttggttcaag tattaacgat gtgttcttct tccgtaaccg cttaggattc  1080
cttagtgggg agaacatcat attgagtcgt acagccaaat acttcaactt ctaccctgcg  1140
tccattgcga accttagtga tgacgaccct atagacgtag ctgtgagtac caaccgaata  1200
gcaatcctta agtacgccgt tccgttctca gaagagttac tcatctggtc cgatgaagca  1260
caattcgtcc tgactgcctc gggtactctc acatctaagt cggttgagtt gaacctaacg  1320
acccagtttg acgtacagga ccgagcgaga cctttgggga ttgggcgtaa tgtctacttt  1380
gctagtccga ggtccagctt cacgtccatc cacaggtact acgctgtgca ggatgtcagt  1440
tccgttaaga atgctgagga cattacatca cacgttccta actacatccc taatggtgtg  1500
ttcagtattt gcggaagtgg tacgaaaaac ttctgttcgg tactatctca cggggaccct  1560
agtaaaatct tcatgtacaa attcctgtac ctgaacgaag agttaaggca acagtcgtgg  1620
tctcattggg actttgggga aaacgtacag gttctagctt gtcagagtat cagctcagat  1680
atgtatgtga ttcttcgcaa tgagttcaat acgttcctag ctagaatctc tttcactaag  1740
aacgccattg acttacaggg agaaccctat cgtgccttta tggacatgaa gattcgatac  1800
acgattccta gtgaacatca acgatgac acattcacta cctctattca tattccaaca   1860
atttatggtg caaacttcgg gaggggcaaa atcactgtat ggagcctga tggtaagata   1920 accgtgtttg agcaacctac ggctgggtgg aatagcgacc cttggctgag actcagcggt   1980
aacttggagg acgcatggt gtacattggg ttcaacatta acttcgtata tgagttctct   2040
aagttcctca tcaagcagac tgccgacgac gggtctacct ccacggaaga cattgggcgc   2100
ttacagttac gccgagcgtg ggttaactac gagaactctg gtacgtttga catttatgtt   2160
gagaaccaat cgtctaactg gaagtacaca atggctggtg cccgattagg ctctaacact   2220
ctgagggctg ggagactgaa cttagggacc ggacaatatc gattccctgt ggttggtaac   2280
gccaagttca acactgtata catcttgtca gatgagacta cccctctgaa catcattggg   2340
```

```
tgtggctggg aaggtaacta cttacggaga agttccggta tttaa            2385
```

```
<210> SEQ ID NO 4
<211> LENGTH: 1662
<212> TYPE: DNA
<213> ORGANISM: Bacteriophage T7

<400> SEQUENCE: 4
atggctaacg taattaaaac cgttttgact taccagttag atggctccaa tcgtgatttt    60
aatatcccgt ttgagtatct agcccgtaag ttcgtagtgg taactcttat tggtgtagac   120
cgaaaggtcc ttacgattaa tacagactat cgctttgcta cacgtactac tatctctctg   180
acaaaggctt ggggtccagc cgatggctac acgaccatcg agttacgtcg agtaacctcc   240
actaccgacc gattggttga ctttacggat ggttcaatcc tccgcgcgta tgaccttaac   300
gtcgctcaga ttcaaacgat gcacgtagcg gaagaggccc gtgacctcac tacggatact   360
atcggtgtca ataacgatgg tcacttggat gctcgtggtc gtcgaattgt gaacctagcg   420
aacgccgtgg atgaccgcga tgctgttccg tttggtcaac taagaccat gaaccagaac   480
tcatggcaag cacgtaatga agccttacag ttccgtaatg aggctgagac tttcagaaac   540
caagcggagg gctttaagaa cgagtccagt accaacgcta cgaacacaaa gcagtggcgc   600
gatgagacca agggtttccg agacgaagcc aagcggttca agaatacggc tggtcaatac   660
gctacatctg ctgggaactc tgcttccgct gcgcatcaat ctgaggtaaa cgctgagaac   720
tctgccacag catccgctaa ctctgctcat ttggcagaac agcaagcaga ccgtgcggaa   780
cgtgaggcag acaagctgga aaattacaat ggattggctg tgcaattga taaggtagat   840
ggaaccaatg tgtactggaa aggaaatatt cacgctaacg ggcgcccttta catgaccaca   900
aacggttttg actgtggcca gtatcaacag ttctttggtg gtgtcactaa tcgttactct   960
gtcatggagt ggggagatga gaacggatgg ctgatgtatg ttcaacgtag agagtggaca  1020
acagcgatag gcgtaacat ccagttagta gtaaacggac agatcatcac ccaaggtgga  1080
gccatgaccg gtcagctaaa attgcagaat gggcatgttc ttcaattaga gtccgcatcc  1140
gacaaggcgc actatattct atctaaagat ggtaacagga ataactggta cattggtaga  1200
gggtcagata caacaatga ctgtaccttc cactcctatg tacatggtac gaccttaaca  1260
ctcaagcagg actatgcagt agttaacaaa cacttccacg taggtcaggc cgttgtggcc  1320
actgatggta atattcaagg tactaagtgg ggaggtaaat ggctggatgc ttacctacgt  1380
gacagcttcg ttgcgaagtc caaggcgtgg actcaggtgt ggtctggtag tgctggcggt  1440
ggggtaagtg tgactgtttc acaggatctc cgcttccgca atatctggat taagtgtgcc  1500
aacaactctt ggaacttctt ccgtactggc cccgatggaa tctacttcat agcctctgat  1560
ggtggatggt tacgattcca aatacactcc aacggtctcg gattcaagaa tattgcagac  1620
agtcgttcag tacctaatgc aatcatggtg gagaacgagt aa                     1662
```

```
<210> SEQ ID NO 5
<211> LENGTH: 160
<212> TYPE: DNA
<213> ORGANISM: Bacteriophage T7

<400> SEQUENCE: 5
tctcacagtg tacggaccta aagttccccc atagggggta cctaaagccc agccaatcac    60
ctaaagtcaa ccttcggttg accttgaggg ttccctaagg gttggggatg acccttgggt   120
ttgtctttgg gtgttacctt gagtgtctct ctgtgtccct                         160
```

<210> SEQ ID NO 6
<211> LENGTH: 799
<212> TYPE: DNA
<213> ORGANISM: Bacteriophage T7

<400> SEQUENCE: 6

| | | | | | |
|---|---|---|---|---|---|
| ttaggactgc | atagggatgc | actatagacc | acggatggtc | agttctttaa | gttactgaaa | 60 |
| agacacgata | aattaatacg | actcactata | gggagaggag | ggacgaaagg | ttactatata | 120 |
| gatactgaat | gaatacttat | agagtgcata | agtatgcat | aatggtgtac | ctagagtgac | 180 |
| ctctaagaat | ggtgattata | ttgtattagt | atcaccttaa | cttaaggacc | aacataaagg | 240 |
| gaggagactc | atgttccgct | tattgttgaa | cctactgcgg | catagagtca | cctaccgatt | 300 |
| tcttgtggta | ctttgtgctg | cccttgggta | cgcatctctt | actggagacc | tcagttcact | 360 |
| ggagtctgtc | gtttgctcta | tactcacttg | tagcgattag | ggtcttcctg | accgactgat | 420 |
| ggctcaccga | gggattcagc | ggtatgattg | catcacacca | cttcatccct | atagagtcaa | 480 |
| gtcctaaggt | atacccataa | agagcctcta | atggtctatc | ctaaggtcta | tacctaaaga | 540 |
| taggccatcc | tatcagtgtc | acctaaagag | ggtcttagag | agggcctatg | gagttcctat | 600 |
| agggtccttt | aaaatatacc | ataaaaatct | gagtgactat | ctcacagtgt | acggacctaa | 660 |
| agttccccca | tagggggtac | ctaaagccca | gccaatcacc | taaagtcaac | cttcggttga | 720 |
| ccttgagggt | tccctaaggg | ttggggatga | cccttgggtt | tgtctttggg | tgttaccttg | 780 |
| agtgtctctc | tgtgtccct | | | | | 799 |

<210> SEQ ID NO 7
<211> LENGTH: 35276
<212> TYPE: DNA
<213> ORGANISM: Artificial Sequence
<220> FEATURE:
<223> OTHER INFORMATION: Phage genome with Tail genes deletion

<400> SEQUENCE: 7

| | | | | | |
|---|---|---|---|---|---|
| tctcacagtg | tacggaccta | aagttccccc | atagggggta | cctaaagccc | agccaatcac | 60 |
| ctaaagtcaa | ccttcggttg | accttgaggg | ttccctaagg | gttggggatg | acccttgggt | 120 |
| tgtctttgg | gtgttacctt | gagtgtctct | ctgtgtccct | atctgttaca | gtctcctaaa | 180 |
| gtatcctcct | aaagtcacct | cctaacgtcc | atcctaaagc | caacacctaa | agcctacacc | 240 |
| taaagaccca | tcaagtcaac | gcctatctta | aagtttaaac | ataaagacca | gacctaaaga | 300 |
| ccagacctaa | agacactaca | taagaccag | acctaaagac | gccttgttgt | tagccataaa | 360 |
| gtgataacct | ttaatcattg | tctttattaa | tacaactcac | tataaggaga | gacaacttaa | 420 |
| agagacttaa | aagattaatt | taaaatttat | caaaaagagt | attgacttaa | agtctaacct | 480 |
| ataggatact | tacagccatc | gagagggaca | cggcgaatag | ccatcccaat | cgacaccggg | 540 |
| gtcaaccgga | taagtagaca | gcctgataag | tcgcacgaaa | acaggtatt | gacaacatga | 600 |
| agtaacatgc | agtaagatac | aaatcgctag | gtaacactag | cagcgtcaac | cgggcgcaca | 660 |
| gtgccttcta | ggtgacttaa | gcgcaccacg | gcacataagg | tgaaacaaaa | cggttgacaa | 720 |
| catgaagtaa | acacggtacg | atgtaccaca | tgaaacgaca | gtgagtcacc | acactgaaag | 780 |
| gtgatgcggt | ctaacgaaac | ctgacctaag | acgctcttta | acaatctggt | aaatagctct | 840 |
| tgagtgcatg | actagcggat | aactcaaggg | tatcgcaagg | tgccctttat | gatattcact | 900 |
| aataactgca | cgaggtaaca | caagatggct | atgtctaaca | tgacttacaa | caacgttttc | 960 |

```
gaccacgctt acgaaatgct gaaagaaaac atccgttatg atgacatccg tgacactgat    1020
gacctgcacg atgctattca catggctgcc gataatgcag ttccgcacta ctacgctgac    1080
atctttagcg taatggcaag tgagggcatt gaccttgagt tcgaagactc tggtctgatg    1140
cctgacacca aggacgtaat ccgcatcctg caagcgcgta tctatgagca attaacgatt    1200
gacctctggg aagacgcaga agacttgctc aatgaatact tggaggaagt cgaggagtac    1260
gaggaggatg aagagtaatg tctactacca acgtgcaata cggtctgacc gctcaaactg    1320 tactttcta tagcgacatg gtgcgctgtg gctttaactg gtcactcgca atggcacagc    1380
tcaaagaact gtacgaaaac aacaaggcaa tagctttaga atctgctgag tgatagactc    1440
aaggtcgctc ctagcgagtg gcctttatga ttatcacttt acttatgagg gagtaatgta    1500
tatgcttact atcggtctac tcaccgctct aggtctagct gtaggtgcat cctttgggaa    1560
ggctttaggt gtagctgtag gttcctactt taccgcttgc atcatcatag gaatcatcaa    1620 agggcacta cgcaaatgat gaagcactac gttatgccaa tccacacgtc aacggggca    1680 accgtatgta cacctgatgg gttcgcaatg aaacaacgaa tcgaacgcct taagcgtgaa    1740
ctccgcatta accgcaagat taacaagata ggttccggct atgacagaac gcactgatgg    1800
cttaaagaaa ggttatatgc ccaatggcac actatacgct gcaaatcggc gaatagtgag    1860
aacttggcga gagaacaacc tcgaacgccg caaggacaag agagggcggc gtggcataga    1920
cgaaaggaaa aggttaaagc caagaaactc gccgcacttg aacaggcact agccaacaca    1980
ctgaacgcta tctcataacg aacataaagg acacaatgca atgaacatta ccgacatcat    2040
gaacgctatc gacgcaatca aagcactgcc aatctgtgaa cttgacaagc gtcaaggtat    2100
gcttatcgac ttactggtcg agatggtcaa cagcgagacg tgtgatggcg agctaaccga    2160
actaaatcag gcacttgagc atcaagattg gtggactacc ttgaagtgtc tcacggctga    2220
cgcagggttc aagatgctcg gtaatggtca cttctcggct gcttatagtc acccgctgct    2280
acctaacaga gtgattaagg tgggctttaa gaaagaggat tcaggcgcag cctataccgc    2340
attctgccgc atgtatcagg gtcgtcctgg tatccctaac gtctacgatg tacagcgcca    2400
cgctggatgc tataccggtgg tacttgacgc acttaaggat tgcgagcgtt tcaacaatga    2460
tgcccattat aaatacgctg agattgcaag cgacatcatt gattgcaatt cggatgagca    2520
tgatgagtta actggatggg atggtgagtt tgttgaaact tgtaaactaa tccgcaagtt    2580 cttgagggc atcgcctcat tcgacatgca tagcgggaac atcatgttct caaatggaga    2640
cgtaccatac atcaccgacc cggtatcatt tcgcagaag aaagacggtg gcgcattcag    2700
catcgaccct gaggaactca tcaaggaagt cgaggaagtc gcacgacaga aagaaattga    2760
ccgcgctaag gcccgtaaag aacgtcacga ggggcgctta gaggcacgca gattcaaacg    2820
tcgcaaccgc aaggcacgta aagcacacaa agctaagcgc gaaagaatgc ttgctgcgtg    2880
gcgatgggct gaacgtcaag aacggcgtaa ccatgaggta gctgtagatg tactaggaag    2940
aaccaataac gctatgctct gggtcaacat gttctctggg gactttaagg cgcttgagga    3000
acgaatcgcg ctgcactggc gtaatgctga ccggatggct atcgctaatg gtcttacgct    3060
caacattgat aagcaacttg acgcaatgtt aatgggctga tagtcttatc ttacaggtca    3120
tctgcgggtg gcctgaatag gtacgattta ctaactggaa gaggcactaa atgaacacga    3180
ttaacatcgc taagaacgac ttctctgaca tcgaactggc tgctatcccg ttcaacactc    3240
tggctgacca ttacggtgag cgtttagctc gcgaacagtt ggcccttgag catgagtctt    3300
acgagatggg tgaagcacgc ttccgcaaga tgtttgagcg tcaacttaaa gctggtgagg    3360
```

```
ttgcggataa cgctgccgcc aagcctctca tcactaccct actccctaag atgattgcac    3420
gcatcaacga ctggtttgag gaagtgaaag ctaagcgcgg caagcgcccg acagccttcc    3480
agttcctgca agaaatcaag ccggaagccg tagcgtacat caccattaag accactctgg    3540
cttgcctaac cagtgctgac aatacaaccg ttcaggctgt agcaagcgca atcggtcggg    3600
ccattgagga cgaggctcgc ttcggtcgta tccgtgacct tgaagctaag cacttcaaga    3660
aaaacgttga ggaacaactc aacaagcgcg tagggcacgc tacaagaaaa gcatttatgc    3720
aagttgtcga ggctgacatg ctctctaagg gtctactcgg tggcgaggcg tggtcttcgt    3780
ggcataagga agactctatt catgtaggag tacgctgcat cgagatgctc attgagtcaa    3840
ccggaatggt tagcttacac cgccaaaatg ctggcgtagt aggtcaagac tctgagacta    3900
tcgaactcgc acctgaatac gctgaggcta tcgcaacccg tgcaggtgcg ctggctggca    3960
tctctccgat gttccaacct tgcgtagttc ctcctaagcc gtggactggc attactggtg    4020
gtggctattg ggctaacggt cgtcgtcctc tggcgctggt gcgtactcac agtaagaaag    4080
cactgatgcg ctacgaagac gtttacatgc ctgaggtgta caaagcgatt aacattgcgc    4140
aaaacaccgc atggaaaatc aacaagaaag tcctagcggt cgccaacgta atcaccaagt    4200
ggaagcattg tccggtcgag gacatccctg cgattgagcg tgaagaactc ccgatgaaac    4260
cggaagacat cgacatgaat cctgaggctc tcaccgcgtg gaaacgtgct gccgctgctg    4320
tgtaccgcaa ggacaaggct cgcaagtctc gccgtatcag ccttgagttc atgcttgagc    4380
aagccaataa gtttgctaac cataaggcca tctggttccc ttacaacatg gactggcgcg    4440
gtcgtgttta cgctgtgtca atgttcaacc cgcaaggtaa cgatatgacc aaaggactgc    4500
ttacgctggc gaaaggtaaa ccaatcggta aggaaggtta ctactggctg aaaatccacg    4560
gtgcaaactg tgcgggtgtc gataaggttc cgttccctga gcgcatcaag ttcattgagg    4620
aaaaccacga gaacatcatg gcttgcgcta agtctccact ggagaacact tggtgggctg    4680
agcaagattc tccgttctgc ttccttgcgt tctgctttga gtacgctggg gtacagcacc    4740
acggcctgag ctataactgc tcccttccgc tggcgtttga cgggtcttgc tctggcatcc    4800
agcacttctc cgcgatgctc cgagatgagg taggtggtcg cgcggttaac ttgcttccta    4860
gtgaaaccgt tcaggacatc tacgggattg ttgctaagaa agtcaacgag attctacaag    4920
cagacgcaat caatgggacc gataacgaag tagttaccgt gaccgatgag aacactggtg    4980
aaatctctga gaaagtcaag ctgggcacta aggcactggc tggtcaatgg ctggcttacg    5040
gtgttactcg cagtgtgact aagcgttcag tcatgacgct ggcttacggg tccaaagagt    5100
tcggcttccg tcaacaagtg ctggaagata ccattcagcc agctattgat tccggcaagg    5160
gtctgatgtt cactcagccg aatcaggctg ctggatacat ggctaagctg atttgggaat    5220
ctgtgagcgt gacggtggta gctgcggttg aagcaatgaa ctggcttaag tctgctgcta    5280
agctgctggc tgctgaggtc aaagataaga agactggaga gattcttcgc aagcgttgcg    5340
ctgtgcattg ggtaactcct gatggttttc ctgtgtggca ggaatacaag aagcctattc    5400
agacgcgctt gaacctgatg ttcctcggtc agttccgctt acagcctacc attaacacca    5460
acaaagatag cgagattgat gcacacaaac aggagtctgg tatcgctcct aactttgtac    5520
acagccaaga cggtagccac cttcgtaaga ctgtagtgtg ggcacacgag aagtacggaa    5580
tcgaatcttt tgcactgatt cacgactcct tcggtaccat tccggctgac gctgcgaacc    5640
tgttcaaagc agtgcgcgaa actatggttg acacacatga gtcttgtgat gtactggctg    5700
```

```
atttctacga ccagttcgct gaccagttgc acgagtctca attggacaaa atgccagcac    5760
ttccggctaa aggtaacttg aacctccgtg acatcttaga gtcggacttc gcgttcgcgt    5820
aacgccaaat caatacgact cactatagag ggacaaactc aaggtcattc gcaagagtgg    5880
cctttatgat tgaccttctt ccggttaata cgactcacta taggagaacc ttaaggttta    5940
actttaagac ccttaagtgt taattagaga tttaaattaa agaattacta agagaggact    6000
ttaagtatgc gtaacttcga aaagatgacc aaacgttcta accgtaatgc tcgtgacttc    6060
gaggcaacca aaggtcgcaa gttgaataag actaagcgtg accgctctca aagcgtagc    6120 tgggagggtc agtaagatgg gacgtttata tagtggtaat ctggcagcat tcaaggcagc    6180
aacaaacaag ctgttccagt tagacttagc ggtcatttat gatgactggt atgatgccta    6240
tacaagaaaa gattgcatac ggttacgtat tgaggacagg agtggaaacc tgattgatac    6300
tagcaccttc taccaccacg acgaggacgt tctgttcaat atgtgtactg attggttgaa    6360
ccatatgtat gaccagttga aggactggaa gtaatacgac tcagtatagg gacaatgctt    6420
aaggtcgctc tctaggagtg gccttagtca tttaaccaat aggagataaa cattatgatg    6480
aacattaaga ctaacccgtt taaagccgtg tctttcgtag agtctgccat taagaaggct    6540
ctggataacg ctgggtatct tatcgctgaa atcaagtacg atggtgtacg cgggaacatc    6600
tgcgtagaca atactgctaa cagttactgg ctctctcgtg tatctaaaac gattccggca    6660
ctggagcact taaacgggtt tgatgttcgc tggaagcgtc tactgaacga tgaccgttgc    6720
ttctacaaag atggctttat gcttgatggg gaactcatgg tcaagggcgt agactttaac    6780
acagggtccg gcctactgcg taccaaatgg actgacacga agaaccaaga gttccatgaa    6840
gagttattcg ttgaaccaat ccgtaagaaa gataaagttc cctttaagct gcacactgga    6900
caccttcaca taaaactgta cgctatcctc ccgctgcaca tcgtggagtc tggagaagac    6960
tgtgatgtca tgacgttgct catgcaggaa cacgttaaga acatgctgcc tctgctacag    7020
gaatacttcc ctgaaatcga atggcaagcg gctgaatctt acgaggtcta cgatatggta    7080
gaactacagc aactgtacga gcagaagcga gcagaaggcc atgagggtct cattgtgaaa    7140
gacccgatgt gtatctataa gcgcggtaag aaatctggct ggtggaaaat gaaacctgag    7200
aacgaagctg acggtatcat tcagggtctg gtatgggta caaaaggtct ggctaatgaa    7260
ggtaaagtga ttggttttga ggtgcttctt gagagtggtc gtttagttaa cgccacgaat    7320
atctctcgcg ccttaatgga tgagttcact gagacagtaa aagaggccac cctaagtcaa    7380
tggggattct ttagcccata cggtattggc gacaacgatg cttgtactat taaccccttac    7440 gatggctggg cgtgtcaaat tagctacatg gaggaaacac ctgatggctc tttgcggcac    7500
ccatcgttcg taatgttccg tggcaccgag gacaaccctc aagagaaaat gtaatcacac    7560
tggctcacct tcgggtgggc ctttctgcgt ttataaggag acactttatg tttaagaagg    7620
ttggtaaatt ccttgcggct ttggcagcta tcctgacgct tgcgtatatt cttgcggtat    7680
accctcaagt agcactagta gtagttggcg cttgttactt agcggcagtg tgtgcttgcg    7740
tgtggagtat agttaactgg taatacgact cactaaagga ggtacacacc atgatgtact    7800
taatgccatt actcatcgtc attgtaggat gccttgcgct ccactgtagc gatgatgata    7860
tgccagatgg tcacgcttaa tacgactcac taaaggagac actatatgtt tcgacttcat    7920
tacaacaaaa gcgttaagaa tttcacggtt cgccgtgctg accgttcaat cgtatgtgcg    7980
agcgagcgcc gagctaagat acctcttatt ggtaacacag ttcctttggc accgagcgtc    8040
cacatcatta tcacccgtgg tgactttgag aaagcaatag acaagaaacg tccggttctt    8100
```

```
agtgtggcag tgacccgctt cccgttcgtc cgtctgttac tcaaacgaat caaggaggtg   8160
ttctgatggg actgttagat ggtgaagcct gggaaaaaga aaacccgcca gtacaagcaa   8220
ctgggtgtat agcttgctta gagaaagatg accgttatcc acacacctgt aacaaaggag   8280
ctaacgatat gaccgaacgt gaacaagaga tgatcattaa gttgatagac aataatgaag   8340
gtcgcccaga tgatttgaat ggctgcggta ttctctgctc caatgtccct tgccacctct   8400
gccccgcaaa taacgatcaa agataaccct taggtgaaat ccgagcgatg gacccacgta   8460
aaccacatct gaataaacct gaggtaactc ctacagatga ccagccttcc gctgagacaa   8520
tcgaaggtgt cactaagcct tcccactaca tgctgtttga cgacattgag ctatcgaag    8580 tgattgctcg ttcaatgacc gttgagcagt caagggata ctgcttcggt aacatcttaa    8640
agtacagact acgtgctggt aagaagtcag agttagcgta cttagagaaa gacctagcga   8700
aagcagactt ctataaagaa ctctttgaga acataagga taaatgttat gcataacttc    8760
aagtcaaccc cacctgccga cagcctatct gatgacttca catcttgctc agagtggtgc   8820
cgaaagatgt gggaagagac attcgacgat gcgtacatca agctgtatga actttggaaa   8880
tcgagaggtc aatgactatg tcaaacgtaa atacaggttc acttagtgtg gacaataaga   8940
agttttgggc taccgtagag tcctcggagc attccttcga ggttccaatc tacgctgaga   9000 ccctagcga agctctggag ttagccgaat ggcaatacgt tccggctggc tttgaggtta    9060
ctcgtgtgcg tccttgtgta gcaccgaagt aatacgactc actattaggg aagactccct   9120
ctgagaaacc aaacgaaacc taaggagat taacattatg ctaagaaga ttttcacctc     9180 tgcgctgggt accgctgaac cttacgctta catcgccaag ccggactacg gcaacgaaga   9240
gcgtggcttt gggaaccctc gtggtgtcta taaagttgac ctgactattc caacaaaga    9300 cccgcgctgc cagcgtatgg tcgatgaaat cgtgaagtgt cacgaagagg cttatgctgc   9360
tgccgttgag gaatacgaag ctaatccacc tgctgtagct cgtggtaaga aaccgctgaa   9420
accgtatgag ggtgacatgc cgttcttcga taacggtgac ggtacgacta cctttaagtt   9480
caaatgctac gcgtctttcc aagacaagaa gaccaaagag accaagcaca tcaatctggt   9540
tgtggttgac tcaaaaggta agaagatgga agacgttccg attatcggtg gtggctctaa   9600
gctgaaagtt aaatattctc tggttccata caagtggaac actgctgtag gtgcgagcgt   9660
taagctgcaa ctggaatccg tgatgctggt cgaactggct acctttggtg gcggtgaaga   9720
cgattgggct gacgaagttg aagagaacgg ctatgttgcc tctggttctg ccaaagcgag   9780
caaaccacgc gacgaagaaa gctgggacga agacgacgaa gagtccgagg aagcagacga   9840
agacggagac ttctaagtgg aactgcggga gaaaatcctt gagcgaatca aggtgacttc   9900
ctctgggtgt tgggagtggc agggcgctac gaacaataaa gggtacgggc aggtgtggtg   9960
cagcaatacc ggaaaggttg tctactgtca tcgcgtaatg tctaatgctc cgaaaggttc  10020
taccgtcctg cactcctgtg ataatccatt atgttgtaac cctgaacacc tatccatagg  10080
aactccaaaa gagaactcca ctgacatggt aaataagggt cgctcacaca aggggtataa  10140
actttcagac gaagacgtaa tgcaatcat ggagtccagc gagtccaatg tatccttagc   10200
tcgcacctat ggtgtctccc aacagactat ttgtgatata cgcaagggga ggcgacatgg  10260
caggttacgg cgctaaagga tccgaaagg ttggagcgtt tcgctctggc ctagaggaca   10320
aggtttcaaa gcagttggaa tcaaaaggta ttaaattcga gtatgaagag tggaaagtgc  10380
cttatgtaat tccggcgagc aatcacactt acactccaga cttcttactt ccaaacggta  10440
```

```
tattcgttga gacaaagggt ctgtgggaaa gcgatgatag aaagaagcac ttattaatta    10500
gggagcagca ccccgagcta gacatccgta ttgtcttctc aagctcacgt actaagttat    10560
acaaaggttc tccaacgtct tatggagagt tctgcgaaaa gcatggtatt aagttcgctg    10620
ataaactgat acctgctgag tggataaagg aacccaagaa ggaggtcccc tttgatagat    10680
taaaaaggaa aggaggaaag aaataatggc tcgtgtacag tttaaacaac gtgaatctac    10740
tgacgcaatc tttgttcact gctcggctac caagccaagt cagaatgttg gtgtccgtga    10800
gattcgccag tggcacaaag agcagggttg gctcgatgtg ggataccact ttatcatcaa    10860
gcgagacggt actgtggagg caggacgaga tgagatggct gtaggctctc acgctaaggg    10920
ttacaaccac aactctatcg gcgtctgcct tgttggtggt atcgacgata aggtaagtt    10980 cgacgctaac tttacgccag cccaaatgca atcccttcgc tcactgcttg tcacactgct    11040
ggctaagtac gaaggcgctg tgcttcgcgc ccatcatgag gtggcgccga aggcttgccc    11100
ttcgttcgac cttaagcgtt ggtgggagaa gaacgaactg gtcacttctg accgtggata    11160
attaattgaa ctcactaaag ggagaccaca gcggtttccc tttgttcgca ttggaggtca    11220
aataatgcgc aagtcttata acaattcta taaggctccg aggaggcata tccaagtgtg    11280
ggaggcagcc aatgggccta taccaaaagg ttattatata gaccacattg acggcaatcc    11340
actcaacgac gccttagaca atctccgtct ggctctccca aaagaaaact catggaacat    11400
gaagactcca aagagcaata cctcaggact aaagggactg agttggagca aggaaaggga    11460
gatgtggaga ggcactgtaa cagctgaggg taaacagcat aactttcgta gtagagatct    11520
attggaagtc gttgcgtgga tttatagaac taggagggaa ttgcatggac aattcgcacg    11580
attccgatag tgtatttctt taccacattc cttgtgacaa ctgtgggagt agtgatggga    11640
actcgctgtt ctctgacgga cacacgttct gctacgtatg cgagaagtgg actgctggta    11700
atgaagacac taagagagg gcttcaaaac ggaaaccctc aggaggtaaa ccaatgactt    11760
acaacgtgtg gaacttcggg gaatccaatg gacgctactc cgcgttaact gcgagaggaa    11820
tctccaagga aacctgtcag aaggctggct actggattgc caaagtagac ggtgtgatgt    11880
accaagtggc tgactatcgg gaccagaacg gcaacattgt gagtcagaag gttcgagata    11940
aagataagaa cttta agacc actggtagtc acaagagtga cgctctgttc gggaagcact    12000
tgtggaatgg tggtaagaag attgtcgtta cagaaggtga aatcgacatg cttaccgtga    12060
tggaacttca agactgtaag tatcctgtag tgtcgttggg tcacggtgcc tctgccgcta    12120
agaagacatg cgctgccaac tacgaatact ttgaccagtt cgaacagatt atcttaatgt    12180
tcgatatgga cgaagcaggg cgcaaagcag tcgaagaggc tgcacaggtt ctacctgctg    12240
gtaaggtacg agtggcagtt cttccgtgta aggatgcaaa cgagtgtcac ctaaatggtc    12300
acgaccgtga aatcatggag caagtgtgga atgctggtcc ttggattcct gatggtgtgg    12360
tatcggctct ttcgttacgt gaacgaatcc gtgagcacct atcgtccgag gaatcagtag    12420
gtttactttt cagtggctgc actggtatca acgataagac cttaggtgcc cgtggtggtg    12480
aagtcattat ggtcacttcc ggttccggta tgggtaagtc aacgttcgtc cgtcaacaag    12540
ctctacaatg gggcacagcg atgggcaaga aggtaggctt agcgatgctt gaggagtccg    12600
ttgaggagac cgctgaggac cttataggtc tacacaaccg tgtccgactg agacaatccg    12660
actcactaaa gagagagatt attgagaacg taagttcga ccaatggttc gatgaactgt    12720
tcggcaacga tacgttccat ctatatgact cattcgccga ggctgagacg gatagactgc    12780
tcgctaagct ggcctacatg cgctcaggct tgggctgtga cgtaatcatt ctagaccaca    12840
```

```
tctcaatcgt cgtatccgct tctggtgaat ccgatgagcg taagatgatt gacaacctga   12900
tgaccaagct caaagggttc gctaagtcaa ctggggtggt gctggtcgta atttgtcacc   12960
ttaagaaccc agacaaaggt aaagcacatg aggaaggtcg ccccgtttct attactgacc   13020
tacgtggttc tggcgcacta cgccaactat ctgatactat tattgccctt gagcgtaatc   13080
agcaaggcga tatgcctaac cttgtcctcg ttcgtattct caagtgccgc tttactggtg   13140
atactggtat cgctggctac atggaataca acaaggaaac cggatggctt gaaccatcaa   13200
gttactcagg ggaagaagag tcacactcag agtcaacaga ctggtccaac gacactgact   13260
tctgacagga ttcttgatga ctttccagac gactacgaga agtttcgctg gagagtccca   13320
ttctaatacg actcactaaa ggagacacac catgttcaaa ctgattaaga gttaggcca    13380
actgctggtt cgtatgtaca acgtggaagc caagcgactg aacgatgagg ctcgtaaaga   13440
ggccacacag tcacgcgctc tggcgattcg ctccaacgaa ctggctgaca gtgcatccac   13500
taaagttacc gaggctgccc gtgtggcaaa ccaagctcaa cagcttttcca aattctttga   13560
gtaatcaaac aggagaaacc attatgtcta acgtagctga aactatccgt ctatccgata   13620
cagctgacca gtggaaccgt cgagtccaca tcaacgttcg caacggtaag gcgactatgg   13680
tttaccgctg gaaggactct aagtcctcta agaatcacac tcagcgtatg acgttgacag   13740
atgagcaagc actgcgtctg gtcaatgcgc ttaccaaagc tgccgtgaca gcaattcatg   13800
aagctggtcg cgtcaatgaa gctatggcta tcctcgacaa gattgataac taagagtggt   13860
atcctcaagg tcgccaaagt ggtggccttc atgaatacta ttcgactcac tataggagat   13920
attaccatgc gtgaccctaa agttatccaa gcagaaatcg ctaaactgga agctgaactg   13980
gaggacgtta agtaccatga agctaagact cgctccgctg ttcacatctt gaagaactta   14040
ggctggactt ggacaagaca gactggctgg aagaaaccag aagttaccaa gctgagtcat   14100
aaggtgttcg ataaggacac tatgacccac atcaaggctg gtgattgggt taaggttgac   14160
atgggagttg ttggtggata cggctacgtc cgctcagtta gtggcaaata tgcacaagtg   14220
tcatacatca caggtgttac tccacgcggt gcaatcgttg ccgataagac caacatgatt   14280
cacacaggtt tcttgacagt tgtttcatat gaagagattg ttaagtcacg ataatcaata   14340
ggagaaatca atatgatcgt ttctgacatc gaagctaacg ccctcttaga gagcgtcact   14400
aagttccact gcggggttat ctacgactac tccaccgctg agtacgtaag ctaccgtccg   14460
agtgacttcg gtgcgtatct ggatgcgctg gaagccgagg ttgcacgagg cggtcttatt   14520
gtgttccaca acggtcacaa gtatgacgtt cctgcattga ccaaactggc aaagttgcaa   14580
ttgaaccgag agttccacct tcctcgtgag aactgtattg acacccttgt gttgtcacgt   14640
ttgattcatt ccaacctcaa ggacaccgat atgggtcttc tgcgttccgg caagttgccc   14700
ggaaaacgct ttgggtctca cgctttggag gcgtggggtt atcgcttagg cgagatgaag   14760
ggtgaataca aagacgactt taagcgtatg cttgaagagc agggtgaaga atacgttgac   14820
ggaatggagt ggtggaactt caacgaagag atgatggact ataacgttca ggacgttgtg   14880
gtaactaaag ctctccttga gaagctactc tctgacaaac attacttccc tcctgagatt   14940
gactttacga acgtaggata cactacgttc tggtcagaat cccttgaggc cgttgacatt   15000
gaacatcgtg ctgcatggct gctcgctaaa caagagcgca acgggttccc gtttgacaca   15060
aaagcaatcg aagagttgta cgtagagtta gctgctcgcc gctctgagtt gctccgtaaa   15120
ttgaccgaaa cgttcggctc gtggtatcag cctaaaggtg gcactgagat gttctgccat   15180
```

```
ccgcgaacag gtaagccact acctaaatac cctcgcatta agacacctaa agttggtggt    15240
atctttaaga agcctaagaa caaggcacag cgagaaggcc gtgagccttg cgaacttgat    15300
acccgcgagt acgttgctgg tgctccttac accccagttg aacatgttgt gtttaaccct    15360
tcgtctcgtg accacattca gaagaaactc caagaggctg ggtgggtccc gaccaagtac    15420
accgataagg gtgctcctgt ggtggacgat gaggtactcg aaggagtacg tgtagatgac    15480
cctgagaagc aagccgctat cgacctcatt aaagagtact tgatgattca gaagcgaatc    15540
ggacagtctg ctgagggaga caaagcatgg cttcgttatg ttgctgagga tggtaagatt    15600
catggttctg ttaaccctaa tggagcagtt acgggtcgtg cgacccatgc gttcccaaac    15660
cttgcgcaaa ttccgggtgt acgttctcct tatggagagc agtgtcgcgc tgcttttggc    15720
gctgagcacc atttggatgg gataactggt aagccttggg ttcaggctgg catcgacgca    15780
tccggtcttg agctacgctg cttggctcac ttcatggctc gctttgataa cggcgagtac    15840
gctcacgaga ttcttaacgg cgacatccac actaagaacc agatagctgc tgaactacct    15900
acccgagata acgctaagac gttcatctat gggttcctct atggtgctgg tgatgagaag    15960
attggacaga ttgttggtgc tggtaaagag cgcggtaagg aactcaagaa gaaattcctt    16020
gagaacaccc ccgcgattgc agcactccgc gagtctatcc aacagacact tgtcgagtcc    16080
tctcaatggg tagctggtga gcaacaagtc aagtggaaac gccgctggat taaaggtctg    16140
gatggtcgta aggtacacgt tcgtagtcct cacgctgcct tgaataccct actgcaatct    16200
gctggtgctc tcatctgcaa actgtggatt atcaagaccg aagagatgct cgtagagaaa    16260
ggcttgaagc atggctggga tggggacttt gcgtacatgg catgggtaca tgatgaaatc    16320
caagtaggct gccgtaccga agagattgct caggtggtca ttgagaccgc acaagaagcg    16380
atgcgctggg ttggagacca ctggaacttc cggtgtcttc tggataccga aggtaagatg    16440
ggtcctaatt gggcgatttg ccactgatac aggaggctac tcatgaacga aagacactta    16500
acaggtgctg cttctgaaat gctagtagcc tacaaattta ccaaagctgg gtacactgtc    16560
tattacccta tgctgactca gagtaaagag gacttggttg tatgtaagga tggtaaattt    16620
agtaaggttc aggttaaaac agccacaacg gttcaaacca acacaggaga tgccaagcag    16680
gttaggctag gtggatgcgg taggtccgaa tataaggatg gagactttga cattcttgcg    16740
gttgtggttg acgaagatgt gcttattttc acatgggacg aagtaaaagg taagacatcc    16800
atgtgtgtcg gcaagagaaa caaaggcata aaactatagg agaaattatt atggctatga    16860
caaagaaatt taaagtgtcc ttcgacgtta ccgcaaagat gtcgtctgac gttcaggcaa    16920
tcttagagaa agatatgctg catctatgta agcaggtcgg ctcaggtgcg attgtcccca    16980
atggtaaaca gaaggaaatg attgtccagt tcctgacaca cggtatggaa ggattgatga    17040
cattcgtagt acgtacatca tttcgtgagg ccattaagga catgcacgaa gagtatgcag    17100
ataaggactc tttcaaacaa tctcctgcaa cagtacggga ggtgttctga tgtctgacta    17160
cctgaaagtg ctgcaagcaa tcaaaagttg ccctaagact ttccagtcca actatgtacg    17220
gaacaatgcg agcctcgtag cggaggccgc ttcccgtggt cacatctcgt gcctgactac    17280
tagtggacgt aacggtggcg cttgggaaat cactgcttcc ggtactcgct ttctgaaacg    17340
aatgggagga tgtgtctaat gtctcgtgac cttgtgacta ttccacgcga tgtgtggaac    17400
gatatacagg gctacatcga ctctctggaa cgtgagaacg atagccttaa gaatcaacta    17460
atggaagctg acgaatacgt agcggaacta gaggagaaac ttaatggcac ttcttgacct    17520
taaacaattc tatgagttac gtgaaggctg cgacgacaag ggtatccttg tgatggacgg    17580
```

```
cgactggctg gtcttccaag ctatgagtgc tgctgagttt gatgcctctt gggaggaaga    17640
gatttggcac cgatgctgtg accacgctaa ggcccgtcag attcttgagg attccattaa    17700
gtcctacgag acccgtaaga aggcttgggc aggtgctcca attgtccttg cgttcaccga    17760
tagtgttaac tggcgtaaag aactggttga cccgaactat aaggctaacc gtaaggccgt    17820
gaagaaacct gtagggtact ttgagttcct tgatgctctc tttgagcgcg aagagttcta    17880
ttgcatccgt gagcctatgc ttgagggtga tgacgttatg ggagttattg cttccaatcc    17940
gtctgccttc ggtgctcgta aggctgtaat catctcttgc gataaggact ttaagaccat    18000
ccctaactgt gacttcctgt ggtgtaccac tggtaacatc ctgactcaga ccgaagagtc    18060
cgctgactgg tggcacctct tccagaccat caagggtgac atcactgatg gttactcagg    18120
gattgctgga tggggtgata ccgccgagga cttcttgaat aacccgttca taaccgagcc    18180
taaaacgtct gtgcttaagt ccggtaagaa caaaggccaa gaggttacta aatgggttaa    18240
acgcgaccct gagcctcatg agacgctttg ggactgcatt aagtccattg gcgcgaaggc    18300
tggtatgacc gaagaggata ttatcaagca gggccaaatg gctcgaatcc tacggttcaa    18360
cgagtacaac tttattgaca aggagattta cctgtggaga ccgtagcgta tattggtctg    18420
ggtctttgtg ttctcggagt gtgcctcatt tcgtgggcc tttgggactt agccagaata    18480
atcaagtcgt tacacgacac taagtgataa actcaaggtc cctaaattaa tacgactcac    18540 tataggga ga taggggcctt tacgattatt actttaagat ttaactctaa gaggaatctt    18600
tattatgtta acacctatta accaattact taagaaccct aacgatattc cagatgtacc    18660
tcgtgcaacc gctgagtatc tacaggttcg attcaactat gcgtacctcg aagcgtctgg    18720
tcatatagga cttatgcgtg ctaatggttg tagtgaggcc cacatcttgg gtttcattca    18780
gggcctacag tatgcctcta acgtcattga cgagattgag ttacgcaagg aacaactaag    18840
agatgatggg gaggattgac actatgtgtt tctcaccgaa aattaaaact ccgaagatgg    18900
ataccaatca gattcgagcc gttgagccag cgcctctgac ccaagaagtg tcaagcgtgg    18960
agttcggtgg gtcttctgat gagacggata ccgagggcac cgaagtgtct ggacgcaaag    19020
gcctcaaggt cgaacgtgat gattccgtag cgaagtctaa agccagcggc aatggctccg    19080
ctcgtatgaa atcttccatc cgtaagtccg catttggagg taagaagtga tgtctgagtt    19140
cacatgtgtg gaggctaaga gtcgcttccg tgcaatccgg tggactgtgg aacaccttgg    19200
gttgcctaaa ggattcgaag gacactttgt gggctacagc ctctacgtag acgaagtgat    19260
ggacatgtct ggttgccgtg aagagtacat tctggactct accggaaaac atgtagcgta    19320
cttcgcgtgg tgcgtaagct gtgacattca ccacaaagga gacattctgg atgtaacgtc    19380
cgttgtcatt aatcctgagg cagactctaa ggcttacag cgattcctag cgaaacgctt    19440
taagtacctt gcggaactcc acgattgcga ttgggtgtct cgttgtaagc atgaaggcga    19500
gacaatgcgt gtatacttta aggaggtata agttatgggt aagaaagtta agaaggccgt    19560
gaagaaagtc accaagtccg ttaagaaagt cgttaaggaa ggggctcgtc cggttaaaca    19620
ggttgctggc ggtctagctg gtctggctgg tggtactggt gaagcacaga tggtggaagt    19680
accacaagct gccgcacaga ttgttgacgt acctgagaaa gaggtttcca ctgaggacga    19740
agcacagaca gaaagcggac gcaagaaagc tcgtgctggc ggtaagaaat ccttgagtgt    19800
agcccgtagc tccggtggcg gtatcaacat ttaatcagga ggttatcgtg gaagactgca    19860
ttgaatggac cggaggtgtc aactctaagg gttatggtcg taagtgggtt aatggtaaac    19920
```

```
ttgtgactcc acataggcac atctatgagg agacatatgg tccagttcca acaggaattg    19980
tggtgatgca tatctgcgat aaccctaggt gctataacat aaagcacctt acgcttggaa    20040
ctccaaagga taattccgag gacatggtta ccaaaggtag acaggctaaa ggagaggaac    20100
taagcaagaa acttacagag tcagacgttc tcgctatacg ctcttcaacc ttaagccacc    20160
gctccttagg agaactgtat ggagtcagtc aatcaaccat aacgcgaata ctacagcgta    20220
agacatggag acacatttaa tggctgagaa acgaacagga cttgcggagg atggcgcaaa    20280
gtctgtctat gagcgtttaa agaacgaccg tgctccctat gagacacgcg ctcagaattg    20340
cgctcaatat accatcccat cattgttccc taaggactcc gataacgcct ctacagatta    20400
tcaaactccg tggcaagccg tgggcgctcg tggtctgaac aatctagcct ctaagctcat    20460
gctggctcta ttccctatgc agacttggat gcgacttact atatctgaat atgaagcaaa    20520
gcagttactg agcgaccccg atggactcgc taaggtcgat gagggcctct cgatggtaga    20580
gcgtatcatc atgaactaca ttgagtctaa cagttaccgc gtgactctct ttgaggctct    20640
caaacagtta gtcgtagctg gtaacgtcct gctgtaccta ccggaaccgg aagggtcaaa    20700
ctataatccc atgaagctgt accgattgtc ttcttatgtg gtccaacgag acgcattcgg    20760
caacgttctg caaatggtga ctcgtgacca gatagctttt ggtgctctcc ctgaggacat    20820
ccgtaaggct gtagaaggtc aaggtggtga aagaaagct gatgagacaa tcgacgtgta    20880
cactcacatc tatctggatg aggactcagg tgaataccatc cgatacgaag aggtcgaggg    20940
tatggaagtc caaggctccg atgggactta tcctaaagag gcttgcccat acatcccgat    21000
tcggatggtc agactagatg gtgaatccta cggtcgttcg tacattgagg aatacttagg    21060
tgacttacgg tcccttgaaa atctccaaga ggctatcgtc aagatgtcca tgattagctc    21120
taaggttatc ggcttagtga atcctgctgg tatcacccag ccacgccgac tgaccaaagc    21180
tcagactggt gacttcgtta ctggtcgtcc agaagacatc tcgttcctcc aactggagaa    21240
gcaagcagac tttactgtag ctaaagccgt aagtgacgct atcgaggctc gccttcgtt    21300
tgcctttatg ttgaactctg cggttcagcg tacaggtgaa cgtgtgaccg ccgaagagat    21360
tcggtatgta gcttctgaac ttgaagatac tttaggtggt gtctactcta tcctttctca    21420
agaattacaa ttgcctctgg tacgagtgct cttgaagcaa ctacaagcca cgcaacagat    21480
tcctgagtta cctaaggaag ccgtagagcc aaccattagt acaggtctgg aagcaattgg    21540
tcgaggacaa gaccttgata agctggagcg gtgtgtcact gcgtgggctg cactggcacc    21600
tatgcgggac gaccctgata ttaaccttgc gatgattaag ttacgtattg ccaacgctat    21660
cggtattgac acttctggta ttctactcac cgaagaacag aagcaacaga gatggcccca    21720
acagtctatg caaatgggta tggataatgg tgctgctgcg ctggctcaag gtatggctgc    21780
acaagctaca gcttcacctg aggctatggc tgctgccgct gattccgtag gtttacagcc    21840
gggaatttaa tacgactcac tatagggaga cctcatcttt gaaatgagcg atgcaagag    21900
gttggagtcc tcggtcttcc tgtagttcaa ctttaaggag acaataataa tggctgaatc    21960
taatgcagac gtatatgcat cttttggcgt gaactccgct gtgatgtctg gtggttccgt    22020
tgaggaacat gagcagaaca tgctggctct tgatgttgct gcccgtgatg gcgatgatgc    22080
aatcgagtta gcgtcagacg aagtggaaac agaacgtgac ctgtatgaca actctgaccc    22140
gttcggtcaa gaggatgacg aaggccgcat tcaggttcgt atcggtgatg ctctgagcc    22200
gaccgatgtg gacactggag aagaaggcgt tgagggcacc gaaggttccg aagagtttac    22260
cccactgggc gagactccag aagaactggt agctgcctct gagcaacttg gtgagcacga    22320
```

```
agagggcttc caagagatga ttaacattgc tgctgagcgt ggcatgagtg tcgagaccat   22380
tgaggctatc cagcgtgagt acgaggagaa cgaagagttg tccgccgagt cctacgctaa   22440
gctggctgaa attggctaca cgaaggcttt cattgactcg tatatccgtg gtcaagaagc   22500
tctggtggag cagtacgtaa acagtgtcat tgagtacgct ggtggtcgtg aacgttttga   22560
tgcactgtat aaccaccttg agacgcacaa ccctgaggct gcacagtcgc tggataatgc   22620
gttgaccaat cgtgacttag cgaccgttaa ggctatcatc aacttggctg gtgagtctcg   22680
cgctaaggcg ttcggtcgta agccaactcg tagtgtgact aatcgtgcta ttccggctaa   22740
acctcaggct accaagcgtg aaggctttgc ggaccgtagc gagatgatta agctatgag   22800 tgaccctcgg tatcgcacag atgccaacta cgtcgtcaa gtcgaacaga agtaatcga   22860 ttcgaacttc tgatagactt cgaaattaat acgactcact ataggagac cacaacggtt   22920 tccctctaga ataattttg tttaacttta agaaggagat atacatatgg ctagcatgac   22980
tggtggacag caaatgggta ctaaccaagg taaaggtgta gttgctgctg gagataaact   23040
ggcgttgttc ttgaaggtat ttggcggtga agtcctgact gcgttcgctc gtacctccgt   23100
gaccacttct cgccacatgg tacgttccat ctccagcggt aaatccgctc agttccctgt   23160
tctgggtcgc actcaggcag cgtatctggc tccgggcgag aacctcgacg ataaacgtaa   23220
ggacatcaaa cacaccgaga aggtaatcac cattgacggt ctcctgacgg ctgacgttct   23280
gatttatgat attgaggacg cgatgaacca ctacgacgtt cgctctgagt atacctctca   23340
gttgggtgaa tctctggcga tggctgcgga tggtgcggtt ctggctgaga ttgccggtct   23400
gtgtaacgtg gaaagcaaat ataatgagaa catcgagggc ttaggtactg ctaccgtaat   23460
tgagaccact cagaacaagg ccgcacttac cgaccaagtt gcgctgggta aggagattat   23520
tgcggctctg actaaggctc gtgcggctct gaccaagaac tatgttccgg ctgctgaccg   23580
tgtgttctac tgtgacccag atagctactc tgcgattctg gcagcactga tgccgaacgc   23640
agcaaactac gctgctctga ttgaccctga aagggttct atccgcaacg ttatgggctt   23700
tgaggttgta gaagttccgc acctcaccgc tggtggtgct ggtaccgctc gtgagggcac   23760
tactggtcag aagcacgtct tccctgccaa taaaggtgag ggtaatgtca aggttgctaa   23820
ggacaacgtt atcggcctgt tcatgcaccg ctctgcggta ggtactgtta agctgcgtga   23880
cttggctctg gagcgcgctc gccgtgctaa cttccaagcg gaccagatta tcgctaagta   23940
cgcaatgggc cacggtggtc ttcgcccaga agctgctggt gcagtggttt tcaaagtgga   24000
gtaatgctgg gggtggcctc aacggtcgct gctagtcccg aagaggcgag tgttacttca   24060
acagaagaaa ccttaacgcc agcacaggag ccgcacgca cccgcgctgc taacaaagcc   24120
cgaaaggaag ctgagttggc tgctgccacc gctgagcaat aactagcata ccccttgggg   24180
gcctctaaac gggtcttgag gggttttttg ctgaaaggag gaactattta atattctcc   24240 ctgtggtggc tcgaaattaa tacgactcac tataggaga caatacgac tacgggaggg   24300 ttttcttatg atgactataa gacctactaa aagtacagac tttgaggtat tcactccggc   24360
tcaccatgac attcttgaag ctaaggctgc tggtattgag ccgagtttcc ctgatgcttc   24420
cgagtgtgtc acgttgagcc tctatgggtt ccctctagct atcggtggta actgcgggga   24480
ccagtgctgg ttcgttacga gcgaccaagt gtggcgactt agtggaaagg ctaagcgaaa   24540
gttccgtaag ttaatcatgg agtatcgcga taagatgctt gagaagtatg atactctttg   24600
gaattacgta tgggtaggca atacgtccca cattcgtttc ctcaagacta tcggtgcggt   24660
```

```
attccatgaa gagtacacac gagatggtca atttcagtta tttacaatca cgaaaggagg   24720
ataaccatat gtgttgggca gccgcaatac ctatcgctat atctggcgct caggctatca   24780
gtggtcagaa cgctcaggcc aaaatgattg ccgctcagac cgctgctggt cgtcgtcaag   24840
ctatggaaat catgaggcag acgaacatcc agaatgctga cctatcgttg caagctcgaa   24900
gtaaacttga ggaagcgtcc gccgagttga cctcacagaa catgcagaag gtccaagcta   24960
ttgggtctat ccgagcggct atcggagaga gtatgcttga aggttcctca atggaccgca   25020
ttaagcgagt cacagaagga cagttcattc gggaagccaa tatggtaact gagaactatc   25080
gccgtgacta ccaagcaatc ttcgcacagc aacttggtgg tactcaaagt gctgcaagtc   25140
agattgacga aatctataag agcgaacaga aacagaagag taagctacag atggttctgg   25200
acccactggc tatcatgggg tcttccgctg cgagtgctta cgcatccggt gcgttcgact   25260
ctaagtccac aactaaggca cctattgttg ccgctaaagg aaccaagacg gggaggtaat   25320
gagctatgag taaaattgaa tctgcccttc aagcggcaca accgggactc tctcggttac   25380
gtggtggtgc tggaggtatg ggctatcgtg cagcaaccac tcaggccgaa cagccaaggt   25440
caagcctatt ggacaccatt ggtcggttcg ctaaggctgg tgccgatatg tataccgcta   25500
aggaacaacg agcacgagac ctagctgatg aacgctctaa cgagattatc cgtaagctga   25560
cccctgagca acgtcgagaa gctctcaaca acgggaccct tctgtatcag gatgacccat   25620
acgctatgga agcactccga gtcaagactg gtcgtaacgc tgcgtatctt gtggacgatg   25680
acgttatgca gaagataaaa gagggtgtct tccgtactcg cgaagagatg gaagagtatc   25740
gccatagtcg ccttcaagag ggcgctaagg tatacgctga gcagttcggc atcgaccctg   25800
aggacgttga ttatcagcgt ggtttcaacg gggacattac cgagcgtaac atctcgctgt   25860
atggtgcgca tgataacttc ttgagccagc aagctcagaa gggcgctatc atgaacagcc   25920
gagtggaact caacggtgtc cttcaagacc ctgatatgct gcgtcgtcca gactctgctg   25980
acttctttga gaagtatatc gacaacggtc tggttactgg cgcaatccca tctgatgctc   26040
aagccacaca gcttataagc caagcgttca gtgacgcttc tagccgtgct ggtggtgctg   26100
acttcctgat gcgagtcggt gacaagaagg taacacttaa cggagccact acgacttacc   26160
gagagttgat tggtgaggaa cagtggaacg ctctcatggt cacagcacaa cgttctcagt   26220
ttgagactga cgcgaagctg aacgagcagt atcgcttgaa gattaactct gcgctgaacc   26280
aagaggaccc aaggacagct tgggagatgc ttcaaggtat caaggctgaa ctagataagg   26340
tccaacctga tgagcagatg acaccacaac gtgagtggct aatctccgca caggaacaag   26400
ttcagaatca gatgaacgca tggacgaaag ctcaggccaa ggctctggac gattccatga   26460
agtcaatgaa caaacttgac gtaatcgaca agcaattcca gaagcgaatc aacggtgagt   26520
gggtctcaac ggatttttaag gatatgccag tcaacgagaa cactggtgag ttcaagcata   26580
gcgatatggt taactacgcc aataagaagc tcgctgagat tgacagtatg gacattccag   26640
acggtgccaa ggatgctatg aagttgaagt accttcaagc ggactctaag gacggagcat   26700
tccgtacagc catcggaacc atggtcactg acgctggtca agagtggtct ccgctgtga   26760 ttaacggtaa gttaccagaa cgaacccag ctatggatgc tctgcgcaga atccgcaatg   26820
ctgaccctca gttgattgct gcgctatacc cagaccaagc tgagctattc ctgacgatgg   26880
acatgatgga caagcagggt attgacccctc aggttattct tgatgccgac cgactgactg   26940
ttaagcggtc caaagagcaa cgctttgagg atgataaagc attcgagtct gcactgaatg   27000
catctaaggc tcctgagatt gcccgtatgc cagcgtcact gcgcgaatct gcacgtaaga   27060
```

```
tttatgactc cgttaagtat cgctcgggga acgaaagcat ggctatggag cagatgacca   27120
agttccttaa ggaatctacc tacacgttca ctggtgatga tgttgacggt gataccgttg   27180
gtgtgattcc taagaatatg atgcaggtta actctgaccc gaaatcatgg gagcaaggtc   27240
gggatattct ggaggaagca cgtaagggaa tcattgcgag caaccttgg ataaccaata    27300 agcaactgac catgtattct caaggtgact ccatttacct tatggacacc acaggtcaag   27360
tcagagtccg atacgacaaa gagttactct cgaaggtctg gagtgagaac cagaagaaac   27420
tcgaagagaa agctcgtgag aaggctctgg ctgatgtgaa caagcgagca cctatagttg   27480
ccgctacgaa ggcccgtgaa gctgctgcta acgagtccg agagaaacgt aaacagactc    27540
ctaagttcat ctacggacgt aaggagtaac taaaggctac ataaggaggc cctaaatgga   27600
taagtacgat aagaacgtac caagtgatta tgatggtctg ttccaaaagg ctgctgatgc   27660
caacggggtc tcttatgacc ttttacgtaa agtcgcttgg acagaatcac gatttgtgcc   27720
tacagcaaaa tctaagactg gaccattagg catgatgcaa tttaccaagg caaccgctaa   27780
ggccctcggt ctgcgagtta ccgatggtcc agacgacgac cgactgaacc ctgagttagc   27840
tattaatgct gccgctaagc aacttgcagg tctggtaggg aagtttgatg gcgatgaact   27900
caaagctgcc cttgcgtaca accaaggcga gggacgcttg ggtaatccac aacttgaggc   27960
gtactctaag ggagacttcg catcaatctc tgaggaggga cgtaactaca tgcgtaacct   28020
tctggatgtt gctaagtcac ctatggctgg acagttggaa acttttggtg gcataacccc   28080
aaagggtaaa ggcattccgg ctgaggtagg attggctgga attggtcaca gcagaaagt    28140 aacacaggaa cttcctgagt ccacaagttt tgacgttaag ggtatcgaac aggaggctac   28200
ggcgaaacca ttcgccaagg acttttggga gacccacgga gaaacacttg acgagtacaa   28260
cagtcgttca accttcttcg gattcaaaaa tgctgccgaa gctgaactct ccaactcagt   28320
cgctgggatg gctttccgtg ctggtcgtct cgataatggt tttgatgtgt ttaaagacac   28380
cattacgccg actcgctgga actctcacat ctggactcca gaggagttag agaagattcg   28440
aacagaggtt aagaaccctg cgtacatcaa cgttgtaact ggtggttccc ctgaaacct    28500 cgatgacctc attaaattgg ctaacgagaa cttttgagaat gactcccgcg ctgccgaggc   28560
tggcctaggt gccaaactga gtgctggtat tattggtgct ggtgtggacc cgcttagcta   28620
tgttcctatg gtcggtgtca ctggtaaggg ctttaagtta atcaataagg ctcttgtagt   28680
tggtgccgaa agtgctgctc tgaacgttgc atccgaaggt ctccgtacct ccgtagctgg   28740
tggtgacgca gactatgcgg gtgctgcctt aggtggcttt gtgtttggcg caggcatgtc   28800
tgcaatcagt gacgctgtag ctgctggact gaaacgcagt aaaccagaag ctgagttcga   28860
caatgagttc atcggtccta tgatgcgatt ggaagcccgt gagacagcac gaaacgccaa   28920
ctctgcggac ctctctcgga tgaacactga gaacatgaag tttgaaggtg aacataatgg   28980
tgtcccttat gaggacttac caacagagag aggtgccgtg gtgttacatg atggctccgt   29040
tctaagtgca agcaacccaa tcaaccctaa gactctaaaa gagttctccg aggttgaccc   29100
tgagaaggct cgcgcgagga atcaaactgg ctgggttcac cgagattggc tgaagacctt   29160
ggggtctgac gatgctgaca tccgtagagt ggctatcgac ctcgttcgct ctcctactgg   29220
tatgcagtct ggtgcctcag gtaagttcgg tgcaacagct tctgacatcc atgagagact   29280
tcatggtact gaccagcgta cttataatga cttgtacaaa gcaatgtctg acgctatgaa   29340
agaccctgag ttctctactg gcggcgctaa gatgtcccgt gaagaaactc gatacactat   29400
```

```
ctaccgtaga gcggcactag ctattgagcg tccagaacta cagaaggcac tcactccgtc    29460
tgagagaatc gttatggaca tcattaagcg tcactttgac accaagcgtg aacttatgga    29520
aaacccagca atattcggta acacaaaggc tgtgagtatc ttccctgaga gtcgccacaa    29580
aggtacttac gttcctcacg tatatgaccg tcatgccaag gcgctgatga ttcaacgcta    29640
cggtgccgaa ggtttgcagg aagggattgc ccgctcatgg atgaacagct acgtctccag    29700
acctgaggtc aaggccagag tcgatgagat gcttaaggaa ttacgcgggg tgaaggaagt    29760
aacaccagag atggtagaga agtacgctat ggataaggct tatggtatct cccactcaga    29820
ccagttcacc aacagttcca taatagaaga gaacattgag ggcttagtag gtatcgagaa    29880
taactcattc cttgaggcac gtaacttgtt tgattcggac ctatccatca ctatgccaga    29940
cggacagcaa ttctcagtga atgacctaag ggacttcgat atgttccgca tcatgccagc    30000
gtatgaccgc cgtgtcaatg gtgacatcgc catcatgggg tctactggta aaaccactaa    30060
ggaacttaag gatgagattt tggctctcaa agcgaaagct gagggagacg gtaagaagac    30120
tggcgaggta catgctttaa tggataccgt taagattctt actggtcgtg ctagacgcaa    30180
tcaggacact gtgtgggaaa cctcactgcg tgccatcaat gacctagggt tcttcgctaa    30240
gaacgcctac atgggtgctc agaacattac ggagattgct gggatgattg tcactggtaa    30300
cgttcgtgct ctagggcatg gtatcccaat tctgcgtgat acactctaca agtctaaacc    30360
agtttcagct aaggaactca aggaactcca tgcgtctctg ttcgggaagg aggtggacca    30420
gttgattcgg cctaaacgtg ctgacattgt gcagcgccta agggaagcaa ctgataccgg    30480
acctgccgtg gcgaacatcg tagggacctt gaagtattca acacaggaac tggctgctcg    30540
ctctccgtgg actaagctac tgaacggaac cactaactac cttctggatg ctgcgcgtca    30600
aggtatgctt ggggatgtta ttagtgccac cctaacaggt aagactaccc gctgggagaa    30660
agaaggcttc cttcgtggtg cctccgtaac tcctgagcag atggctggca tcaagtctct    30720
catcaaggaa catatggtac gcggtgagga cgggaagttt accgttaagg acaagcaagc    30780
gttctctatg gacccacggg ctatggactt atggagactg gctgacaagg tagctgatga    30840
ggcaatgctg cgtccacata aggtgtcctt acaggattcc catgcgttcg gagcactagg    30900
taagatggtt atgcagttta agtctttcac tatcaagtcc cttaactcta gttcctgcg    30960
aaccttctat gatggataca agaacaaccg agcgattgac gctgcgctga gcatcatcac    31020
ctctatgggt ctcgctggtg gtttctatgc tatggctgca cacgtcaaag catacgctct    31080
gcctaaggag aaacgtaagg agtacttgga gcgtgcactg gacccaacca tgattgccca    31140
cgctgcgtta tctcgtagtt ctcaattggg tgctccttg gctatggttg acctagttgg    31200
tggtgtttta gggttcgagt cctccaagat ggctcgctct acgattctac ctaaggacac    31260
cgtgaaggaa cgtgacccaa acaaaccgta cacctctaga gaggtaatgg gcgctatggg    31320
ttcaaacctt ctggaacaga tgccttcggc tggctttgtg gctaacgtag gggctacctt    31380
aatgaatgct gctggcgtgg tcaactcacc taataaagca accgagcagg acttcatgac    31440
tggtctatg aactccacaa agagttagt accgaacgac ccattgactc aacagcttgt    31500
gttgaagatt tatgaggcga acggtgttaa cttgagggag cgtaggaaat aatacgactc    31560
actatagga gaggcgaaat aatcttctcc ctgtagtctc ttagatttac tttaaggagg    31620
tcaattggta aatcacaagg aaagacgtgt agtccacgga tggactctca aggaggtaca    31680
aggtgctatc attagacttt aacaacgaat tgattaaggc tgctccaatt gttgggacgg    31740
gtgtagcaga tgttagtgct cgactgttct ttgggttaag ccttaacgaa tggttctacg    31800
```

```
ttgctgctat cgcctacaca gtggttcaga ttggtgccaa ggtagtcgat aagatgattg   31860
actggaagaa agccaataag gagtgatatg tatggaaaag gataagagcc ttattacatt   31920
cttagagatg ttggacactg cgatggctca gcgtatgctt gcggacctt  cggaccatga   31980 gcgtcgctct ccgcaactct ataatgctat taacaaactg ttagaccgcc acaagttcca   32040
gattggtaag ttgcagccgg atgttcacat cttaggtggc cttgctggtg ctcttgaaga   32100
gtacaaagag aaagtcggtg ataacggtct tacggatgat gatatttaca cattacagtg   32160
atatactcaa ggccactaca gatagtggtc tttatggatg tcattgtcta tacgagatgc   32220
tcctacgtga aatctgaaag ttaacgggag gcattatgct agaatttta  cgtaagctaa   32280 tcccttgggt tctcgctggg atgctattcg ggttaggatg gcatctaggg tcagactcaa   32340
tggacgctaa atggaaacag gaggtacaca atgagtacgt taagagagtt gaggctgcga   32400
agagcactca aagagcaatc gatgcggtat ctgctaagta tcaagaagac cttgccgcgc   32460
tggaagggag cactgatagg attatttctg atttgcgtag cgacaataag cggttgcgcg   32520
tcagagtcaa aactaccgga acctccgatg gtcagtgtgg attcgagcct gatggtcgag   32580
ccgaacttga cgaccgagat gctaaacgta ttctcgcagt gacccagaag ggtgacgcat   32640
ggattcgtgc gttacaggat actattcgtg aactgcaacg taagtaggaa atcaagtaag   32700
gaggcaatgt gtcctactcaa tccaatcgta atgcgctcgt agtggcgcaa ctgaaaggag   32760
acttcgtggc gttcctattc gtcttatgga aggcgctaaa cctaccggtg cccactaagt   32820
gtcagattga catggctaag gtgctggcga atggagacaa caagaagttc atcttacagg   32880
ctttccgtgg tatcggtaag tcgttcatca catgtgcgtt cgttgtgtgg tccttatgga   32940
gagaccctca gttgaagata cttatcgtat cagcctctaa ggagcgtgca gacgctaact   33000
ccatctttat taagaacatc attgacctgc tgccattcct atctgagtta aagccaagac   33060
ccggacagcg tgactcggta atcagctttg atgtaggccc agccaatcct gaccactctc   33120
ctagtgtgaa atcagtaggt atcactggtc agttaactgg tagccgtgct gacattatca   33180
ttgcggatga cgttgagatt ccgtctaaca gcgcaactat gggtgcccgt gagaagctat   33240
ggactctggt tcaggagttc gctgcgttac ttaaaccgct gccttcctct cgcgttatct   33300
accttggtac acctcagaca gagatgactc tctataagga acttgaggat aaccgtgggt   33360
acacaaccat tatctggcct gctctgtacc caaggacacg tgaagagaac ctctattact   33420
cacagcgtct tgctcctatg ttacgcgctg agtacgatga gaaccctgag gcacttgctg   33480
ggactccaac agacccagtg cgctttgacc gtgatgacct cgcgagcgt  gagttggaat   33540 acggtaaggc tggctttacg ctacagttca tgcttaaccc taaccttagt gatgccgaga   33600
agtacccgct gaggcttcgt gacgctatcg tagcggcctt agacttagag aaggcccaa   33660 tgcattacca gtggcttccg aaccgtcaga acatcattga ggaccttcct aacgttggcc   33720
ttaagggtga tgacctgcat acgtaccacg attgttccaa caactcaggt cagtaccaac   33780
agaagattct ggtcattgac cctagtggtc gcggtaagga cgaaacaggt tacgctgtgc   33840
tgtacacact gaacggttac atctacctta tggaagctgg aggtttccgt gatggctact   33900
ccgataagac ccttgagtta ctcgctaaga aggcaaagca atggggagtc cagacggttg   33960
tctacgagag taacttcggt gacggtatgt tcggtaaggt attcagtcct atccttctta   34020
aacaccacaa ctgtgcgatg gaagagattc gtgcccgtgg tatgaaagag atgcgtattt   34080
gcgataccct tgagccagtc atgcagactc accgccttgt aattcgtgat gaggtcatta   34140
```

-continued

```
gggccgacta ccagtccgct cgtgacgtag acggtaagca tgacgttaag tactcgttgt    34200
tctaccagat gacccgtatc actcgtgaga aaggcgctct ggctcatgat gaccgattgg    34260
atgcccttgc gttaggcatt gagtatctcc gtgagtccat gcagttggat tccgttaagg    34320
tcgagggtga agtacttgct gacttccttg aggaacacat gatgcgtcct acggttgctg    34380
ctacgcatat cattgagatg tctgtgggag gagttgatgt gtactctgag gacgatgagg    34440
gttacggtac gtctttcatt gagtggtgat ttatgcatta ggactgcata gggatgcact    34500
atagaccacg gatggtcagt tctttaagtt actgaaaaga cacgataaat taatacgact    34560
cactataggg agaggaggga cgaaaggtta ctatatagat actgaatgaa tacttataga    34620
gtgcataaag tatgcataat ggtgtaccta gagtgacctc taagaatggt gattatattg    34680
tattagtatc accttaactt aaggaccaac ataaagggag gagactcatg ttccgcttat    34740
tgttgaacct actgcggcat agagtcacct accgatttct tgtggtactt tgtgctgccc    34800
ttgggtacgc atctcttact ggagacctca gttcactgga gtctgtcgtt tgctctatac    34860
tcacttgtag cgattagggt cttcctgacc gactgatggc tcaccgaggg attcagcggt    34920
atgattgcat cacaccactt catccctata gagtcaagtc ctaaggtata cccataaaga    34980
gcctctaatg gtctatccta aggtctatac ctaaagatag gccatcctat cagtgtcacc    35040
taaagagggt cttagagagg gcctatggag ttcctatagg gtcctttaaa ataccata     35100 aaaatctgag tgactatctc acagtgtacg gacctaaagt tcccccatag ggggtaccta    35160
aagcccagcc aatcacctaa agtcaacctt cggttgacct tgagggttcc ctaagggttg    35220
gggatgaccc ttgggtttgt ctttgggtgt taccttgagt gtctctctgt gtccct         35276
```

<210> SEQ ID NO 8
<211> LENGTH: 60
<212> TYPE: DNA
<213> ORGANISM: Artificial Sequence
<220> FEATURE:
<223> OTHER INFORMATION: Forward primer

<400> SEQUENCE: 8

```
cttgaagacg aaagggcctc gtgatacgcc tctcacagtg tacggaccta aagttccccc    60
```

<210> SEQ ID NO 9
<211> LENGTH: 30
<212> TYPE: DNA
<213> ORGANISM: Artificial Sequence
<220> FEATURE:
<223> OTHER INFORMATION: Reverse primer

<400> SEQUENCE: 9

```
attacgcgat gacagtagac aacctttccg                                     30
```

<210> SEQ ID NO 10
<211> LENGTH: 30
<212> TYPE: DNA
<213> ORGANISM: Artificial Sequence
<220> FEATURE:
<223> OTHER INFORMATION: Forward primer

<400> SEQUENCE: 10

```
tgcagcaata ccggaaaggt tgtctactgt                                     30
```

<210> SEQ ID NO 11
<211> LENGTH: 30
<212> TYPE: DNA
<213> ORGANISM: Artificial Sequence

```
<220> FEATURE:
<223> OTHER INFORMATION: Reverse primer

<400> SEQUENCE: 11
atatgtctcc tcatagatgt gcctatgtgg                                30

<210> SEQ ID NO 12
<211> LENGTH: 30
<212> TYPE: DNA
<213> ORGANISM: Artificial Sequence
<220> FEATURE:
<223> OTHER INFORMATION: Forward primer

<400> SEQUENCE: 12
acttgtgact ccacataggc acatctatga                                30

<210> SEQ ID NO 13
<211> LENGTH: 45
<212> TYPE: DNA
<213> ORGANISM: Artificial Sequence
<220> FEATURE:
<223> OTHER INFORMATION: Reverse primer

<400> SEQUENCE: 13
agggagaata tttaaatagt tcctcctttc agcaaaaaac ccctc               45

<210> SEQ ID NO 14
<211> LENGTH: 41
<212> TYPE: DNA
<213> ORGANISM: Artificial Sequence
<220> FEATURE:
<223> OTHER INFORMATION: Forward primer

<400> SEQUENCE: 14
gaaaggagga actatttaaa tattctccct gtggtggctc g                   41

<210> SEQ ID NO 15
<211> LENGTH: 30
<212> TYPE: DNA
<213> ORGANISM: Artificial Sequence
<220> FEATURE:
<223> OTHER INFORMATION: Reverse primer

<400> SEQUENCE: 15
gaataacctg agggtcaata ccctgcttgt                                30

<210> SEQ ID NO 16
<211> LENGTH: 30
<212> TYPE: DNA
<213> ORGANISM: Artificial Sequence
<220> FEATURE:
<223> OTHER INFORMATION: Forward primer

<400> SEQUENCE: 16
gacatgatgg acaagcaggg tattgaccct                                30

<210> SEQ ID NO 17
<211> LENGTH: 44
<212> TYPE: DNA
<213> ORGANISM: Artificial Sequence
<220> FEATURE:
<223> OTHER INFORMATION: Reverse primer

<400> SEQUENCE: 17
cttgtgattt accaattgac ctccttaaag taaatctaag agac                44
```

<210> SEQ ID NO 18
<211> LENGTH: 45
<212> TYPE: DNA
<213> ORGANISM: Artificial Sequence
<220> FEATURE:
<223> OTHER INFORMATION: Forward primer

<400> SEQUENCE: 18
ctttaaggag gtcaattggt aaatcacaag gaaagacgtg tagtc                45

<210> SEQ ID NO 19
<211> LENGTH: 60
<212> TYPE: DNA
<213> ORGANISM: Artificial Sequence
<220> FEATURE:
<223> OTHER INFORMATION: Reverse primer

<400> SEQUENCE: 19
cataatagaa acgacacgaa attacaaaat agggacacag agagacactc aagtaacac  60

<210> SEQ ID NO 20
<211> LENGTH: 30
<212> TYPE: DNA
<213> ORGANISM: Artificial Sequence
<220> FEATURE:
<223> OTHER INFORMATION: Forward primer

<400> SEQUENCE: 20
attttgtaat tcgtgtcgt ttctattatg                                   30

<210> SEQ ID NO 21
<211> LENGTH: 30
<212> TYPE: DNA
<213> ORGANISM: Artificial Sequence
<220> FEATURE:
<223> OTHER INFORMATION: Reverse primer

<400> SEQUENCE: 21
ggcgtatcac gaggcccttt cgtcttcaag                                  30

<210> SEQ ID NO 22
<211> LENGTH: 38661
<212> TYPE: DNA
<213> ORGANISM: Artificial Sequence
<220> FEATURE:
<223> OTHER INFORMATION: Phage genome with head gene deletion

<400> SEQUENCE: 22
tctcacagtg tacggaccta agttcccccc atagggggta cctaaagccc agccaatcac   60
ctaaagtcaa ccttcggttg accttgaggg ttccctaagg gttggggatg acccttgggt  120
ttgtctttgg gtgttacctt gagtgtctct ctgtgtccct atctgttaca gtctcctaaa  180
gtatcctcct aaagtcacct cctaacgtcc atcctaaagc caacacctaa agcctacacc  240
taaagaccca tcaagtcaac gcctatctta agtttaaac ataaagacca gacctaaaga   300
ccagacctaa agacactaca taaagaccag acctaaagac gccttgttgt tagccataaa  360
gtgataacct ttaatcattg tctttattaa tacaactcac tataaggaga gacaacttaa  420
agagacttaa aagattaatt taaatttat caaaagagt attgacttaa agtctaacct   480
ataggatact tacagccatc gagagggaca cggcgaatag ccatcccaat cgacaccggg  540
gtcaaccgga taagtagaca gcctgataag tcgcacgaaa acaggtatt gacaacatga   600 agtaacatgc agtaagatac aaatcgctag gtaacactag cagcgtcaac cgggcgcaca  660

```
gtgccttcta ggtgacttaa gcgcaccacg gcacataagg tgaaacaaaa cggttgacaa      720
catgaagtaa acacggtacg atgtaccaca tgaaacgaca gtgagtcacc acactgaaag      780
gtgatgcggt ctaacgaaac ctgacctaag acgctcttta acaatctggt aaatagctct      840
tgagtgcatg actagcggat aactcaaggg tatcgcaagg tgcccttat gatattcact       900 aataactgca cgaggtaaca caagatggct atgtctaaca tgacttacaa caacgttttc      960
gaccacgctt acgaaatgct gaaagaaaac atccgttatg atgacatccg tgacactgat     1020
gacctgcacg atgctattca catggctgcc gataatgcag ttccgcacta ctacgctgac     1080
atctttagcg taatggcaag tgagggcatt gaccttgagt tcgaagactc tggtctgatg     1140
cctgacacca aggacgtaat ccgcatcctg caagcgcgta tctatgagca attaacgatt     1200
gacctctggg aagacgcaga agacttgctc aatgaatact tggaggaagt cgaggagtac     1260
gaggaggatg aagagtaatg tctactacca acgtgcaata cggtctgacc gctcaaactg     1320
tacttttcta tagcgacatg gtgcgctgtg gctttaactg gtcactcgca atggcacagc     1380
tcaaagaact gtacgaaaac aacaaggcaa tagctttaga atctgctgag tgatagactc     1440
aaggtcgctc ctagcgagtg gcctttatga ttatcacttt acttatgagg gagtaatgta     1500
tatgcttact atcggtctac tcaccgctct aggtctagct gtaggtgcat cctttgggaa     1560
ggctttaggt gtagctgtag gttcctactt taccgcttgc atcatcatag gaatcatcaa     1620
aggggcacta cgcaaatgat gaagcactac gttatgccaa tccacacgtc caacggggca     1680
accgtatgta cacctgatgg gttcgcaatg aaacaacgaa tcgaacgcct taagcgtgaa     1740
ctccgcatta accgcaagat taacaagata ggttccggct atgacagaac gcactgatgg     1800
cttaaagaaa ggttatatgc ccaatggcac actatacgct gcaaatcggc gaatagtgag     1860
aacttggcga gagaacaacc tcgaacgccg caaggacaag agagggcggc gtggcataga     1920
cgaaaggaaa aggttaaagc caagaaactc gccgcacttg aacaggcact agccaacaca     1980
ctgaacgcta tctcataacg aacataaagg acacaatgca atgaacatta ccgacatcat     2040
gaacgctatc gacgcaatca aagcactgcc aatctgtgaa cttgacaagc gtcaaggtat     2100
gcttatcgac ttactggtcg agatggtcaa cagcgagacg tgtgatggcg agctaaccga     2160
actaaatcag gcacttgagc atcaagattg gtggactacc ttgaagtgtc tcacggctga     2220
cgcagggttc aagatgctcg gtaatggtca cttctcggct gcttatagtc acccgctgct     2280
acctaacaga gtgattaagg tgggctttaa gaaagaggat tcaggcgcag cctataccgc     2340
attctgccgc atgtatcagg tcgtcctgg tatccctaac gtctacgatg tacagcgcca     2400
cgctggatgc tatacggtgg tacttgacgc acttaaggat tgcgagcgtt tcaacaatga     2460
tgcccattat aaatacgctg agattgcaag cgacatcatt gattgcaatt cggatgagca     2520
tgatgagtta actggatggg atggtgagtt tgttgaaact tgtaaactaa tccgcaagtt     2580
ctttgagggc atcgcctcat tcgacatgca tagcgggaac atcatgttct caaatgagaa     2640
cgtaccatac atcaccgacc cggtatcatt ctcgcagaag aaagacggtg gcgcattcag     2700 catcgacccct gaggaactca tcaaggaagt cgaggaagtc gcacgacaga aagaaattga     2760
ccgcgctaag gcccgtaaag aacgtcacga ggggcgctta gaggcacgca gattcaaacg     2820
tcgcaaccgc aaggcacgta aagcacacaa agctaagcgc gaaagaatgc ttgctgcgtg     2880
gcgatgggct gaacgtcaag aacggcgtaa ccatgaggta gctgtagatg tactaggaag     2940
aaccaataac gctatgctct gggtcaacat gttctctggg gactttaagg cgcttgagga     3000
```

```
acgaatcgcg ctgcactggc gtaatgctga ccggatggct atcgctaatg gtcttacgct    3060
caacattgat aagcaacttg acgcaatgtt aatgggctga tagtcttatc ttacaggtca    3120
tctgcgggtg gcctgaatag gtacgattta ctaactggaa gaggcactaa atgaacacga    3180
ttaacatcgc taagaacgac ttctctgaca tcgaactggc tgctatcccg ttcaacactc    3240
tggctgacca ttacggtgag cgtttagctc gcgaacagtt ggcccttgag catgagtctt    3300
acgagatggg tgaagcacgc ttccgcaaga tgtttgagcg tcaacttaaa gctggtgagg    3360
ttgcggataa cgctgccgcc aagcctctca tcactaccct actccctaag atgattgcac    3420
gcatcaacga ctggtttgag gaagtgaaag ctaagcgcgg caagcgcccg acagccttcc    3480
agttcctgca agaaatcaag ccggaagccg tagcgtacat caccattaag accactctgg    3540
cttgcctaac cagtgctgac aatacaaccg ttcaggctgt agcaagcgca atcggtcggg    3600
ccattgagga cgaggctcgc ttcggtcgta tccgtgacct tgaagctaag cacttcaaga    3660
aaaacgttga ggaacaactc aacaagcgcg tagggcacgt ctacaagaaa gcatttatgc    3720
aagttgtcga ggctgacatg ctctctaagg gtctactcgg tggcgaggcg tggtcttcgt    3780
ggcataagga agactctatt catgtaggag tacgctgcat cgagatgctc attgagtcaa    3840
ccggaatggt tagcttacac cgccaaaatg ctggcgtagt aggtcaagac tctgagacta    3900
tcgaactcgc acctgaatac gctgaggcta tcgcaacccg tgcaggtgcg ctggctggca    3960
tctctccgat gttccaacct tgcgtagttc ctcctaagcc gtggactggc attactggtg    4020
gtggctattg ggctaacggt cgtcgtcctc tggcgctggt gcgtactcac agtaagaaag    4080
cactgatgcg ctacgaagac gtttacatgc ctgaggtgta caaagcgatt aacattgcgc    4140
aaaacaccgc atggaaaatc aacaagaaag tcctagcggt cgccaacgta atcaccaagt    4200
ggaagcattg tccggtcgag gacatccctg cgattgagcg tgaagaactc ccgatgaaac    4260
cggaagacat cgacatgaat cctgaggctc tcaccgcgtg gaaacgtgct gccgctgctg    4320
tgtaccgcaa ggacaaggct cgcaagtctc gccgtatcag ccttgagttc atgcttgagc    4380
aagccaataa gtttgctaac cataaggcca tctggttccc ttacaacatg gactggcgcg    4440
gtcgtgttta cgctgtgtca atgttcaacc cgcaaggtaa cgatatgacc aaaggactgc    4500
ttacgctggc gaaaggtaaa ccaatcggta aggaaggtta ctactggctg aaaatccacg    4560
gtgcaaactg tgcgggtgtc gataaggttc cgttccctga gcgcatcaag ttcattgagg    4620
aaaaccacga gaacatcatg gcttgcgcta agtctccact ggagaacact tggtgggctg    4680
agcaagattc tccgttctgc ttccttgcgt tctgctttga gtacgctggg gtacagcacc    4740
acggcctgag ctataactgc tcccttccgc tggcgtttga cgggtcttgc tctggcatcc    4800
agcacttctc cgcgatgctc cgagatgagg taggtggtcg cgcggttaac ttgcttccta    4860
gtgaaaccgt tcaggacatc tacgggattg ttgctaagaa agtcaacgag attctacaag    4920
cagacgcaat caatgggacc gataacgaag tagttaccgt gaccgatgag aacactggtg    4980
aaatctctga gaaagtcaag ctgggcacta aggcactggc tggtcaatgg ctggcttacg    5040
gtgttactcg cagtgtgact aagcgttcag tcatgacgct ggcttacggg tccaaagagt    5100
tcggcttccg tcaacaagtg ctggaagata ccattcagcc agctattgat tccggcaagg    5160
gtctgatgtt cactcagccg aatcaggctg ctggatacat ggctaagctg atttgggaat    5220
ctgtgagcgt gacggtggta gctgcggttg aagcaatgaa ctggcttaag tctgctgcta    5280
agctgctggc tgctgaggtc aaagataaga agactggaga gattcttcgc aagcgttgcg    5340
ctgtgcattg ggtaactcct gatggtttcc ctgtgtggca ggaatacaag aagcctattc    5400
```

```
agacgcgctt gaacctgatg ttcctcggtc agttccgctt acagcctacc attaacacca    5460
acaaagatag cgagattgat gcacacaaac aggagtctgg tatcgctcct aactttgtac    5520
acagccaaga cggtagccac cttcgtaaga ctgtagtgtg ggcacacgag aagtacggaa    5580
tcgaatcttt tgcactgatt cacgactcct tcggtaccat tccggctgac gctgcgaacc    5640
tgttcaaagc agtgcgcgaa actatggttg acacatatga gtcttgtgat gtactggctg    5700
atttctacga ccagttcgct gaccagttgc acgagtctca attggacaaa atgccagcac    5760
ttccggctaa aggtaacttg aacctccgtg acatcttaga gtcggacttc gcgttcgcgt    5820
aacgccaaat caatacgact cactatagag ggacaaactc aaggtcattc gcaagagtgg    5880
cctttatgat tgaccttctt ccggttaata cgactcacta taggagaacc ttaaggttta    5940
actttaagac ccttaagtgt taattagaga tttaaattaa agaattacta agagaggact    6000
ttaagtatgc gtaacttcga aaagatgacc aaacgttcta accgtaatgc tcgtgacttc    6060
gaggcaacca aaggtcgcaa gttgaataag actaagcgtg accgctctca caagcgtagc    6120
tgggagggtc agtaagatgg gacgtttata tagtggtaat ctggcagcat tcaaggcagc    6180
aacaaacaag ctgttccagt tagacttagc ggtcatttat gatgactggt atgatgccta    6240
tacaagaaaa gattgcatac ggttacgtat tgaggacagg agtggaaacc tgattgatac    6300
tagcaccttc taccaccacg acgaggacgt tctgttcaat atgtgtactg attggttgaa    6360
ccatatgtat gaccagttga aggactggaa gtaatacgac tcagtatagg acaatgctt    6420 aaggtcgctc tctaggagtg gccttagtca tttaaccaat aggagataaa cattatgatg    6480
aacattaaga ctaacccgtt taaagccgtg tctttcgtag agtctgccat taagaaggct    6540
ctggataacg ctgggtatct tatcgctgaa atcaagtacg atggtgtacg cgggaacatc    6600
tgcgtagaca atactgctaa cagttactgg ctctctcgtg tatctaaaac gattccggca    6660
ctggagcact taaacgggtt tgatgttcgc tggaagcgtc tactgaacga tgaccgttgc    6720
ttctacaaag atggctttat gcttgatggg gaactcatgg tcaagggcgt agactttaac    6780
acagggtccg gcctactgcg taccaaatgg actgacacga agaaccaaga gttccatgaa    6840
gagttattcg ttgaaccaat ccgtaagaaa gataaagttc cctttaagct gcacactgga    6900
caccttcaca taaaactgta cgctatcctc ccgctgcaca tcgtggagtc tggagaagac    6960
tgtgatgtca tgacgttgct catgcaggaa cacgttaaga acatgctgcc tctgctacag    7020
gaatacttcc ctgaaatcga atggcaagcg gctgaatctt acgaggtcta cgatatggta    7080
gaactacagc aactgtacga gcagaagcga gcagaaggcc atgagggtct cattgtgaaa    7140
gacccgatgt gtatctataa gcgcggtaag aaatctggct ggtggaaaat gaaacctgag    7200
aacgaagctg acggtatcat tcagggtctg tatgggggta caaaaggtct ggctaatgaa    7260
ggtaaagtga ttggttttga ggtgcttctt gagagtggtc gtttagttaa cgccacgaat    7320
atctctcgcg ccttaatgga tgagttcact gagacagtaa agaggccac cctaagtcaa    7380 tggggattct ttagcccata cggtattggc gacaacgatg cttgtactat taaccttac    7440 gatggctggg cgtgtcaaat tagctacatg gaggaaacac ctgatggctc tttgcggcac    7500
ccatcgttcg taatgttccg tggcaccgag gacaaccctc aagagaaaat gtaatcacac    7560
tggctcacct tcgggtgggc ctttctgcgt ttataaggag acactttatg tttaagaagg    7620
ttggtaaatt ccttgcggct ttggcagcta tcctgacgct tgcgtatatt cttgcggtat    7680
accctcaagt agcactagta gtagttggcg cttgttactt agcggcagtg tgtgcttgcg    7740
```

```
tgtggagtat agttaactgg taatacgact cactaaagga ggtacacacc atgatgtact    7800
taatgccatt actcatcgtc attgtaggat gccttgcgct ccactgtagc gatgatgata    7860
tgccagatgg tcacgcttaa tacgactcac taaaggagac actatatgtt tcgacttcat    7920
tacaacaaaa gcgttaagaa tttcacggtt cgccgtgctg accgttcaat cgtatgtgcg    7980
agcgagcgcc gagctaagat acctcttatt ggtaacacag ttcctttggc accgagcgtc    8040
cacatcatta tcacccgtgg tgactttgag aaagcaatag acaagaaacg tccggttctt    8100
agtgtggcag tgacccgctt cccgttcgtc cgtctgttac tcaaacgaat caaggaggtg    8160
ttctgatggg actgttagat ggtgaagcct gggaaaaaga aaacccgcca gtacaagcaa    8220
ctgggtgtat agcttgctta gagaaagatg accgttatcc acacacctgt aacaaaggag    8280
ctaacgatat gaccgaacgt gaacaagaga tgatcattaa gttgatagac aataatgaag    8340
gtcgcccaga tgatttgaat ggctgcggta ttctctgctc caatgtccct tgccacctct    8400
gccccgcaaa taacgatcaa aagataacct taggtgaaat ccgagcgatg gacccacgta    8460
aaccacatct gaataaacct gaggtaactc ctacagatga ccagccttcc gctgagacaa    8520
tcgaaggtgt cactaagcct tcccactaca tgctgtttga cgacattgag gctatcgaag    8580
tgattgctcg ttcaatgacc gttgagcagt tcaaggggata ctgcttcggt aacatcttaa    8640
agtacagact acgtgctggt aagaagtcag agttagcgta cttagagaaa gacctagcga    8700
aagcagactt ctataaagaa ctctttgaga aacataagga taaatgttat gcataacttc    8760
aagtcaaccc cacctgccga cagcctatct gatgacttca catcttgctc agagtggtgc    8820
cgaaagatgt gggaagagac attcgacgat gcgtacatca agctgtatga actttggaaa    8880
tcgagaggtc aatgactatg tcaaacgtaa atacaggttc acttagtgtg gacaataaga    8940
agttttgggc taccgtagag tcctcggagc attccttcga ggttccaatc tacgctgaga    9000
ccctagacga agctctggag ttagccgaat ggcaatacgt tccggctggc tttgaggtta    9060
ctcgtgtgcg tccttgtgta gcaccgaagt aatacgactc actattaggg aagactccct    9120
ctgagaaacc aaacgaaacc taaaggagat taacattatg gctaagaaga ttttcacctc    9180
tgcgctgggt accgctgaac cttacgctta catcgccaag ccggactacg gcaacgaaga    9240
gcgtggcttt gggaaccctc gtggtgtcta taaagttgac ctgactattc ccaacaaaga    9300
cccgcgctgc cagcgtatgg tcgatgaaat cgtgaagtgt cacgaagagg cttatgctgc    9360
tgccgttgag gaatacgaag ctaatccacc tgctgtagct cgtggtaaga aaccgctgaa    9420
accgtatgag ggtgacatgc cgttcttcga taacggtgac ggtacgacta cctttaagtt    9480
caaatgctac gcgtctttcc aagacaagaa gaccaaagag accaagcaca tcaatctggt    9540
tgtggttgac tcaaaaggta agaagatgga agacgttccg attatcggtg gtggctctaa    9600
gctgaaagtt aaatattctc tggttccata caagtggaac actgctgtag gtgcgagcgt    9660
taagctgcaa ctggaatccg tgatgctggt cgaactggct acctttggtg gcggtgaaga    9720
cgattgggct gacgaagttg aagagaacgg ctatgttgcc tctggttctg ccaaagcgag    9780
caaaccacgc gacgaagaaa gctgggacga agacgacgaa gagtccgagg aagcagacga    9840
agacggagac ttctaagtgg aactgcggga gaaaatcctt gagcgaatca aggtgacttc    9900
ctctgggtgt tgggagtggc agggcgctac gaacaataaa gggtacgggc aggtgtggtg    9960
cagcaatacc ggaaaggttg tctactgtca tcgcgtaatg tctaatgctc cgaaaggttc   10020
taccgtcctg cactcctgtg ataatccatt atgttgtaac cctgaacacc tatccatagg   10080
aactccaaaa gagaactcca ctgacatggt aaataagggt cgctcacaca aggggtataa   10140
```

```
actttcagac gaagacgtaa tggcaatcat ggagtccagc gagtccaatg tatccttagc    10200
tcgcacctat ggtgtctccc aacagactat ttgtgatata cgcaaaggga ggcgacatgg    10260
caggttacgg cgctaaagga atccgaaagg ttggagcgtt tcgctctggc ctagaggaca    10320
aggtttcaaa gcagttggaa tcaaaaggta ttaaattcga gtatgaagag tggaaagtgc    10380
cttatgtaat tccggcgagc aatcacactt acactccaga cttcttactt ccaaacggta    10440
tattcgttga dacaaagggt ctgtgggaaa gcgatgatag aaagaagcac ttattaatta    10500
gggagcagca ccccgagcta dacatccgta ttgtcttctc aagctcacgt actaagttat    10560
acaaaggttc tccaacgtct tatggagagt tctgcgaaaa gcatggtatt aagttcgctg    10620
ataaactgat acctgctgag tggataaagg aacccaagaa ggaggtcccc tttgatagat    10680
taaaaaggaa aggaggaaag aaataatggc tcgtgtacag tttaaacaac gtgaatctac    10740
tgacgcaatc tttgttcact gctcggctac caagccaagt cagaatgttg gtgtccgtga    10800
gattcgccag tggcacaaag agcagggttg gctcgatgtg ggataccact ttatcatcaa    10860
gcgagacggt actgtggagg caggacgaga tgagatggct gtaggctctc acgctaaggg    10920
ttacaaccac aactctatcg gcgtctgcct tgttggtggt atcgacgata aaggtaagtt    10980
cgacgctaac tttacgccag cccaaatgca atcccttcgc tcactgcttg tcacactgct    11040
ggctaagtac gaaggcgctg tgcttcgcgc ccatcatgag gtggcgccga aggcttgccc    11100
ttcgttcgac cttaagcgtt ggtgggagaa gaacgaactg gtcacttctg accgtggata    11160
attaattgaa ctcactaaag ggagaccaca gcggtttccc tttgttcgca ttggaggtca    11220
aataatgcgc aagtcttata acaattcta taaggctccg aggaggcata tccaagtgtg    11280
ggaggcagcc aatgggccta taccaaaagg ttattatata gaccacattg acggcaatcc    11340
actcaacgac gccttagaca atctccgtct ggctctccca aaagaaaact catggaacat    11400
gaagactcca aagagcaata cctcaggact aaagggactg agttggagca aggaaaggga    11460
gatgtggaga ggcactgtaa cagctgaggg taaacagcat aactttcgta gtagagatct    11520
attggaagtc gttgcgtgga tttatagaac taggagggaa ttgcatggac aattcgcacg    11580
attccgatag tgtatttctt taccacattc cttgtgacaa ctgtgggagt agtgatggga    11640
actcgctgtt ctctgacgga cacacgttct gctacgtatg cgagaagtgg actgctggta    11700
atgaagacac taaagagagg gcttcaaaac ggaaaccctc aggaggtaaa ccaatgactt    11760
acaacgtgtg gaacttcggg gaatccaatg gacgctactc cgcgttaact gcgagaggaa    11820
tctccaagga aacctgtcag aaggctggct actggattgc caaagtagac ggtgtgatgt    11880
accaagtggc tgactatcgg gaccagaacg gcaacattgt gagtcagaag gttcgagata    11940
aagataagaa ctttaagacc actggtagtc acaagagtga cgctctgttc gggaagcact    12000
tgtggaatgg tggtaagaag attgtcgtta cagaaggtga aatcgacatg cttaccgtga    12060
tggaacttca agactgtaag tatcctgtag tgtcgttggg tcacggtgcc tctgccgcta    12120
agaagacatg cgctgccaac tacgaatact tgaccagtt cgaacagatt atcttaatgt    12180
tcgatatgga cgaagcaggg cgcaaagcag tcgaagaggc tgcacaggtt ctacctgctg    12240
gtaaggtacg agtggcagtt cttccgtgta aggatgcaaa cgagtgtcac ctaaatggtc    12300
acgaccgtga aatcatggag caagtgtgga atgctggtcc ttggattcct gatggtgtgg    12360
tatcggctct ttcgttacgt gaacgaatcc gtgagcacct atcgtccgag gaatcagtag    12420
gtttactttt cagtggctgc actggtatca acgataagac cttaggtgcc cgtgtggtg    12480
```

```
aagtcattat ggtcacttcc ggttccggta tgggtaagtc aacgttcgtc cgtcaacaag    12540
ctctacaatg gggcacagcg atgggcaaga aggtaggctt agcgatgctt gaggagtccg    12600
ttgaggagac cgctgaggac cttataggtc tacacaaccg tgtccgactg agacaatccg    12660
actcactaaa gagagagatt attgagaacg gtaagttcga ccaatggttc gatgaactgt    12720
tcggcaacga tacgttccat ctatatgact cattcgccga ggctgagacg atagactgc     12780 tcgctaagct ggcctacatg cgctcaggct gggctgtga cgtaatcatt ctagaccaca     12840
tctcaatcgt cgtatccgct tctggtgaat ccgatgagcg taagatgatt gacaacctga    12900
tgaccaagct caaagggttc gctaagtcaa ctggggtggt gctggtcgta atttgtcacc    12960
ttaagaaccc agacaaaggt aaagcacatg aggaaggtcg ccccgtttct attactgacc    13020
tacgtggttc tggcgcacta cgccaactat ctgatactat tattgcccct gagcgtaatc    13080
agcaaggcga tatgcctaac cttgtcctcg ttcgtattct caagtgccgc tttactggtg    13140
atactggtat cgctggctac atggaataca acaaggaaac cggatggctt gaaccatcaa    13200
gttactcagg ggaagaagag tcacactcag agtcaacaga ctggtccaac gacactgact    13260
tctgacagga ttcttgatga ctttccagac gactacgaga agtttcgctg gagagtccca    13320
ttctaatacg actcactaaa ggagacacac catgttcaaa ctgattaaga agttaggcca    13380
actgctggtt cgtatgtaca acgtggaagc caagcgactg aacgatgagg ctcgtaaaga    13440
ggccacacag tcacgcgctc tggcgattcg ctccaacgaa ctggctgaca gtgcatccac    13500
taaagttacc gaggctgccc gtgtggcaaa ccaagctcaa cagctttcca aattctttga    13560
gtaatcaaac aggagaaacc attatgtcta acgtagctga aactatccgt ctatccgata    13620
cagctgacca gtggaaccgt cgagtccaca tcaacgttcg caacggtaag gcgactatgg    13680
tttaccgctg gaaggactct aagtcctcta agaatcacac tcagcgtatg acgttgacag    13740
atgagcaagc actgcgtctg gtcaatgcgc ttaccaaagc tgccgtgaca gcaattcatg    13800
aagctggtcg cgtcaatgaa gctatggcta tcctcgacaa gattgataac taagagtggt    13860
atcctcaagg tcgccaaagt ggtggccttc atgaatacta ttcgactcac tataggagat    13920
attaccatgc gtgaccctaa agttatccaa gcagaaatcg ctaaactgga agctgaactg    13980
gaggacgtta agtaccatga agctaagact cgctccgctg ttcacatctt gaagaactta    14040
ggctggactt ggacaagaca gactggctgg aagaaaccag aagttaccaa gctgagtcat    14100
aaggtgttcg ataaggacac tatgacccac atcaaggctg gtgattgggt taaggttgac    14160
atgggagttt ggtggata cggctacgtc cgctcagtta gtggcaaata tgcacaagtg       14220
tcatacatca caggtgttac tccacgcggt gcaatcgttg ccgataagac caacatgatt    14280
cacacaggtt tcttgacagt tgtttcatat gaagagattg ttaagtcacg ataatcaata    14340
ggagaaatca atatgatcgt ttctgacatc gaagctaacg ccctcttaga gagcgtcact    14400
aagttccact gcggggttat ctacgactac tccaccgctg agtacgtaag ctaccgtccg    14460
agtgacttcg gtgcgtatct ggatgcgctg gaagccgagg ttgcacgagg cggtcttatt    14520
gtgttccaca acgtcacaa gtatgacgtt cctgcattga ccaaactggc aaagttgcaa    14580
ttgaaccgag agttccacct tcctcgtgag aactgtattg acacccttgt gttgtcacgt    14640
ttgattcatt ccaacctcaa ggacaccgat atgggtcttc tgcgttccgg caagttgccc    14700
ggaaaacgct ttgggtctca cgctttggag gcgtggggtt atcgcttagg cgagatgaag    14760
ggtgaataca aagacgactt taagcgtatg cttgaagagc agggtgaaga atacgttgac    14820
ggaatggagt ggtggaactt caacgaagag atgatggact ataacgttca ggacgttgtg    14880
```

```
gtaactaaag ctctccttga gaagctactc tctgacaaac attacttccc tcctgagatt   14940
gactttacgg acgtaggata cactacgttc tggtcagaat cccttgaggc cgttgacatt   15000
gaacatcgtg ctgcatggct gctcgctaaa caagagcgca acgggttccc gtttgacaca   15060
aaagcaatcg aagagttgta cgtagagtta gctgctcgcc gctctgagtt gctccgtaaa   15120
ttgaccgaaa cgttcggctc gtggtatcag cctaaaggtg gcactgagat gttctgccat   15180
ccgcgaacag gtaagccact acctaaatac cctcgcatta agacacctaa agttggtggt   15240
atctttaaga agcctaagaa caaggcacag cgagaaggcc gtgagccttg cgaacttgat   15300
acccgcgagt acgttgctgg tgctccttac accccagttg aacatgttgt gtttaaccct   15360
tcgtctcgtg accacattca gaagaaactc aagaggctg ggtgggtccc gaccaagtac    15420
accgataagg tgctcctgt ggtggacgat gaggtactcg aaggagtacg tgtagatgac     15480
cctgagaagc aagccgctat cgacctcatt aaagagtact tgatgattca gaagcgaatc   15540
ggacagtctg ctgagggaga caaagcatgg cttcgttatg ttgctgagga tggtaagatt   15600
catggttctg ttaaccctaa tggagcagtt acgggtcgtg cgacccatgc gttcccaaac   15660
cttgcgcaaa ttccgggtgt acgttctcct tatggagagc agtgtcgcgc tgcttttggc   15720
gctgagcacc atttggatgg gataactggt aagccttggg ttcaggctgg catcgacgca   15780
tccggtcttg agctacgctg cttggctcac ttcatggctc gctttgataa cggcgagtac   15840
gctcacgaga ttcttaacgg cgacatccac actaagaacc agatagctgc tgaactacct   15900
acccgagata cgctaagac gttcatctat gggttcctct atggtgctgg tgatgagaag     15960
attggacaga ttgttggtgc tggtaaagag cgcggtaagg aactcaagaa gaaattcctt   16020
gagaacaccc ccgcgattgc agcactccgc gagtctatcc aacagacact tgtcgagtcc   16080
tctcaatggg tagctggtga gcaacaagtc aagtggaaac gccgctggat taaaggtctg   16140
gatggtcgta aggtacacgt tcgtagtcct cacgctgcct tgaatacct actgcaatct     16200
gctggtgctc tcatctgcaa actgtggatt atcaagaccg aagagatgct cgtagagaaa   16260
ggcttgaagc atggctggga tggggactt gcgtacatgg catgggtaca tgatgaaatc     16320
caagtaggct gccgtaccga agagattgct caggtggtca ttgagaccgc acaagaagcg   16380
atgcgctggg ttggagacca ctggaacttc cggtgtcttc tggataccga aggtaagatg   16440
ggtcctaatt gggcgatttg ccactgatac aggaggctac tcatgaacga aagcacttta   16500
acaggtgctg cttctgaaat gctagtagcc tacaaatta ccaaagctgg gtacactgtc      16560
tattacccta tgctgactca gagtaaagag gacttggttg tatgtaagga tggtaaattt   16620
agtaaggttc aggttaaaac agccacaacg gttcaaacca acacaggaga tgccaagcag   16680
gttaggctag gtgatgcgg taggtccgaa tataaggatg gagactttga cattcttgcg    16740
gttgtggttg acgaagatgt gcttattttc acatgggacg aagtaaaagg taagacatcc   16800
atgtgtgtcg gcaagagaaa caaaggcata aaactatagg agaaattatt atggctatga   16860
caaagaaatt taaagtgtcc ttcgacgtta ccgcaaagat gtcgtctgac gttcaggcaa   16920
tcttagagaa agatatgctg catctatgta agcaggtcgg ctcaggtgcg attgtcccca   16980
atggtaaaca gaaggaaatg attgtccagt tcctgacaca cggtatggaa ggattgatga   17040
cattcgtagt acgtacatca tttcgtgagg ccattaagga catgcacgaa gagtatgcag   17100
ataaggactt tttcaaacaa tctcctgcaa cagtacggga ggtgttctga tgtctgacta   17160
cctgaaagtg ctgcaagcaa tcaaaagttg ccctaagact ttccagtcca actatgtacg   17220
```

```
gaacaatgcg agcctcgtag cggaggccgc ttcccgtggt cacatctcgt gcctgactac    17280
tagtggacgt aacggtggcg cttgggaaat cactgcttcc ggtactcgct ttctgaaacg    17340
aatgggagga tgtgtctaat gtctcgtgac cttgtgacta ttccacgcga tgtgtggaac    17400
gatatacagg gctacatcga ctctctggaa cgtgagaacg atagccttaa gaatcaacta    17460
atggaagctg acgaatacgt agcggaacta gaggagaaac ttaatggcac ttcttgacct    17520
taaacaattc tatgagttac gtgaaggctg cgacgacaag ggtatccttg tgatggacgg    17580
cgactggctg gtcttccaag ctatgagtgc tgctgagttt gatgcctctt gggaggaaga    17640
gatttggcac cgatgctgtg accacgctaa ggcccgtcag attcttgagg attccattaa    17700
gtcctacgag acccgtaaga aggcttgggc aggtgctcca attgtccttg cgttcaccga    17760
tagtgttaac tggcgtaaag aactggttga cccgaactat aaggctaacc gtaaggccgt    17820
gaagaaacct gtagggtact ttgagttcct tgatgctctc tttgagcgcg aagagttcta    17880
ttgcatccgt gagcctatgc ttgagggtga tgacgttatg ggagttattg cttccaatcc    17940
gtctgccttc ggtgctcgta aggctgtaat catctcttgc gataaggact ttaagaccat    18000
ccctaactgt gacttcctgt ggtgtaccac tggtaacatc ctgactcaga ccgaagagtc    18060
cgctgactgg tggcacctct tccagaccat caagggtgac atcactgatg gttactcagg    18120
gattgctgga tggggtgata ccgccgagga cttcttgaat aacccgttca taaccgagcc    18180
taaaacgtct gtgcttaagt ccggtaagaa caaaggccaa gaggttacta atgggttaa    18240 acgcgaccct gagcctcatg agacgctttg ggactgcatt aagtccattg gcgcgaaggc    18300
tggtatgacc gaagaggata ttatcaagca gggccaaatg gctcgaatcc tacgqttcaa    18360 cgagtacaac tttattgaca aggagattta cctgtggaga ccgtagcgta tattggtctg    18420
ggtctttgtg ttctcggagt gtgcctcatt tcgtggggcc tttgggactt agccagaata    18480
atcaagtcgt tacacgacac taagtgataa actcaaggtc cctaaattaa tacgactcac    18540
tatagggaga taggggcctt tacgattatt actttaagat ttaactctaa gaggaatctt    18600
tattatgtta acacctatta accaattact taagaaccct aacgatattc cagatgtacc    18660
tcgtgcaacc gctgagtatc tacaggttcg attcaactat gctacctcg aagcgtctgg     18720 tcatatagga cttatgcgtg ctaatggttg tagtgaggcc cacatcttgg gtttcattca    18780
gggcctacag tatgcctcta acgtcattga cgagattgag ttacgcaagg aacaactaag    18840
agatgatggg gaggattgac actatgtgtt tctcaccgaa aattaaaaact ccgaagatgg    18900 ataccaatca gattcgagcc gttgagccag cgcctctgac ccaagaagtg tcaagcgtgg    18960
agttcggtgg gtcttctgat gagacggata ccgagggcac cgaagtgtct ggacgcaaag    19020
gcctcaaggt cgaacgtgat gattccgtag cgaagtctaa agccagcggc aatggctccg    19080
ctcgtatgaa atcttccatc cgtaagtccg catttggagg taagaagtga tgtctgagtt    19140
cacatgtgtg gaggctaaga gtcgcttccg tgcaatccgg tggactgtgg aacaccttgg    19200
gttgcctaaa ggattcgaag gacactttgt gggctacagc ctctacgtag acgaagtgat    19260
ggacatgtct ggttgccgtg aagagtacat tctggactct accggaaaac atgtagcgta    19320
cttcgcgtgt tgcgtaagct gtgacattca ccacaaagga gacattctgg atgtaacgtc    19380
cgttgtcatt aatcctgagg cagactctaa gggcttacag cgattcctag cgaaacgctt    19440
taagtacctt gcggaactcc acgattgcga ttgggtgtct cgttgtaagc atgaaggcga    19500
gacaatgcgt gtatacttta aggaggtata agttatgggt aagaaagtta agaaggccgt    19560
gaagaaagtc accaagtccg ttaagaaagt cgttaaggaa ggggctcgtc cggttaaaca    19620
```

```
ggttgctggc ggtctagctg gtctggctgg tggtactggt gaagcacaga tggtggaagt    19680
accacaagct gccgcacaga ttgttgacgt acctgagaaa gaggtttcca ctgaggacga    19740
agcacagaca gaaagcggac gcaagaaagc tcgtgctggc ggtaagaaat ccttgagtgt    19800
agcccgtagc tccggtggcg gtatcaacat ttaatcagga ggttatcgtg gaagactgca    19860
ttgaatggac cggaggtgtc aactctaagg gttatggtcg taagtgggtt aatggtaaac    19920
ttgtgactcc acataggcac atctatgagg agacatatgg tccagttcca acaggaattg    19980
tggtgatgca tatctgcgat aaccctaggt gctataacat aaagcacctt acgcttggaa    20040
ctccaaagga taattccgag gacatggtta ccaaaggtag acaggctaaa ggagaggaac    20100
taagcaagaa acttacagag tcagacgttc tcgctatacg ctcttcaacc ttaagccacc    20160
gctccttagg agaactgtat ggagtcagtc aatcaaccat aacgcgaata ctacagcgta    20220
agacatggag acacatttaa tggctgagaa acgaacagga cttgcggagg atggcgcaaa    20280
gtctgtctat gagcgtttaa agaacgaccg tgctccctat gagacacgcg ctcagaattg    20340
cgctcaatat accatcccat cattgttccc taaggactcc gataacgcct ctacagatta    20400
tcaaactccg tggcaagccg tgggcgctcg tggtctgaac aatctagcct ctaagctcat    20460
gctggctcta ttccctatgc agacttggat gcgacttact atatctgaat atgaagcaaa    20520
gcagttactg agcgacccog atggactcgc taaggtcgat gagggcctct cgatggtaga    20580
gcgtatcatc atgaactaca ttgagtctaa cagttaccgc gtgactctct tgaggctct    20640 caaacagtta gtcgtagctg gtaacgtcct gctgtaccta ccggaaccgg aagggtcaaa    20700
ctataatccc atgaagctgt accgattgtc ttcttatgtg gtccaacgag acgcattcgg    20760
caacgttctg caaatggtga ctcgtgacca gatagctttt ggtgctctcc ctgaggacat    20820
ccgtaaggct gtagaaggtc aaggtggtga gaagaaagct gatgagacaa tcgacgtgta    20880
cactcacatc tatctggatg aggactcagg tgaatacctc cgatacgaag aggtcgaggg    20940
tatggaagtc caaggctccg atgggactta tcctaaagag gcttgcccat acatcccgat    21000
tcggatggtc agactagatg gtgaatccta cggtcgttcg tacattgagg aatacttagg    21060
tgacttacgg tcccttgaaa atctccaaga ggctatcgtc aagatgtcca tgattagctc    21120
taaggttatc ggcttagtga atcctgctgg tatcacccag ccacgccgac tgaccaaagc    21180
tcagactggt gacttcgtta ctggtcgtcc agaagacatc tcgttcctcc aactggaaaa    21240
gcaagcagac tttactgtag ctaaagccgt aagtgacgct atcgaggctc gccttcgtt    21300 tgcctttatg ttgaactctg cggttcagcg tacaggtgaa cgtgtgaccg ccgaagagat    21360
tcggtatgta gcttctgaac ttgaagatac tttaggtggt gtctactcta tcctttctca    21420
agaattacaa ttgcctctgg tacgagtgct cttgaagcaa ctacaagcca cgcaacagat    21480
tcctgagtta cctaaggaag ccgtagagcc aaccattagt acaggtctgg aagcaattgg    21540
tcgaggacaa gaccttgata agctggagcg gtgtgtcact gcgtgggctg cactggcacc    21600
tatgcgggac gaccctgata ttaaccttgc gatgattaag ttacgtattg ccaacgctat    21660
cggtattgac acttctggta ttctactcac cgaagaacag aagcaacaga agatggccca    21720
acagtctatg caaatgggta tggataatgg tgctgctgcg ctggctcaag gtatggctgc    21780
acaagctaca gcttcacctg aggctatggc tgctgccgct gattccgtag gtttacagcc    21840
gggaatttaa tacgactcac tatagggaga cctcatcttt gaaatgagcg atgacaagag    21900
gttggagtcc tcggtcttcc tgtagttcaa ctttaaggag acaataataa tggctgaatc    21960
```

```
taatgcagac gtatatgcat cttttggcgt gaactccgct gtgatgtctg gtggttccgt   22020
tgaggaacat gagcagaaca tgctggctct tgatgttgct gcccgtgatg gcgatgatgc   22080
aatcgagtta gcgtcagacg aagtggaaac agaacgtgac ctgtatgaca actctgaccc   22140
gttcggtcaa gaggatgacg aaggccgcat tcaggttcgt atcggtgatg gctctgagcc   22200
gaccgatgtg gacactggag aagaaggcgt tgagggcacc gaaggttccg aagagtttac   22260
cccactgggc gagactccag aagaactggt agctgcctct gagcaacttg gtgagcacga   22320
agagggcttc caagagatga ttaacattgc tgctgagcgt ggcatgagtg tcgagaccat   22380
tgaggctatc cagcgtgagt acgaggagaa cgaagagttg tccgccgagt cctacgctaa   22440
gctggctgaa attggctaca cgaaggcttt cattgactcg tatatccgtg gtcaagaagc   22500
tctggtggag cagtacgtaa acagtgtcat tgagtacgct ggtggtcgtg aacgttttga   22560
tgcactgtat aaccaccttg agacgcacaa ccctgaggct gcacagtcgc tggataatgc   22620
gttgaccaat cgtgacttag cgaccgttaa ggctatcatc aacttggctg gtgagtctcg   22680
cgctaaggcg ttcggtcgta agccaactcg tagtgtgact aatcgtgcta ttccggctaa   22740
acctcaggct accaagcgtg aaggctttgc ggaccgtagc gagatgatta agctatgag   22800 tgaccctcgg tatcgcacag atgccaacta tcgtcgtcaa gtcgaacaga agtaatcga   22860 ttcgaacttc tgatagactt cgaaatctag cataacccct tggggcctct aaacgggtct   22920
tgaggggttt tttgctgaaa ggaggaacta tatgcgctca tacgatatga acgttgagac   22980
tgccgctgag ttatcagctg tgaacgacat tctggcgtct atcggtgaac ctccggtatc   23040
aacgctggaa ggtgacgcta acgcagatgc agcgaacgct cggcgtattc tcaacaagat   23100
taaccgacag attcaatctc gtggatggac gttcaacatt gaggaaggca taacgctact   23160
acctgatgtt tactccaacc tgattgtata cagtgacgac tatttatccc taatgtctac   23220
ttccggtcaa tccatctacg ttaaccgagg tggctatgtg tatgaccgaa cgagtcaatc   23280
agaccgcttt gactctggta ttactgtgaa cattattcgt ctccgcgact acgatgagat   23340
gcctgagtgc ttccgttact ggattgtcac caaggcttcc cgtcagttca caaccgatt   23400 cttgggggca ccggaagtag agggtgtact ccaagaagag gaagatgagg ctagacgtct   23460
ctgcatggag tatgagatgg actacggtgg gtacaatatg ctggatggag atgcgttcac   23520
ttctggtcta ctgactcgct aacattaata aataaggagg ctctaatggc actcattagc   23580
caatcaatca agaacttgaa gggtggtatc agccaacagc ctgacatcct tcgttatcca   23640
gaccaagggt cacgccaagt taacggttgg tcttcggaga ccgagggcct ccaaaagcgt   23700
ccacctcttg tttcttaaa tacacttgga gacaacggtg cgttaggtca agctccgtac   23760
atccacctga ttaaccgaga tgagcacgaa cagtattacg ctgtgttcac tggtagcgga   23820
atccgagtgt tcgacctttc tggtaacgag aagcaagtta ggtatcctaa cggttccaac   23880
tacatcaaga ccgctaatcc acgtaacgac ctgcgaatgg ttactgtagc agactatacg   23940
ttcatcgtta accgtaacgt tgttgcacag aagaacacaa agtctgtcaa cttaccgaat   24000
tacaacccta atcaagacgg attgattaac gttcgtggtg gtcagtatgg tagggaacta   24060
attgtacaca ttaacggtaa agacgttgcg aagtataaga taccagatgg tagtcaacct   24120
gaacacgtaa acaatacgga tgcccaatgg ttagctgaag agttagccaa gcagatgcgc   24180
actaacttgt ctgattggac tgtaaatgta gggcaagggt tcatccatgt gaccgcacct   24240
agtggtcaac agattgactc cttcacgact aaagatggct acgcagacca gttgattaac   24300
cctgtgaccc actacgctca gtcgttctct aagctgccac ctaatgctcc taacggctac   24360
```

```
atggtgaaaa tcgtagggga cgcctctaag tctgccgacc agtattacgt tcggtatgac  24420
gctgagcgga aagtttggac tgagacttta ggttggaaca ctgaggacca agttctatgg  24480
gaaaccatgc cacacgctct tgtgcgagcc gctgacggta atttcgactt caagtggctt  24540
gagtggtctc ctaagtcttg tggtgacgtt gacaccaacc cttggccttc ttttgttggt  24600
tcaagtatta acgatgtgtt cttcttccgt aaccgcttag gattccttag tggggagaac  24660
atcatattga gtcgtacagc caaatacttc aacttctacc ctgcgtccat tgcgaacctt  24720
agtgatgacg accctataga cgtagctgtg agtaccaacc gaatagcaat ccttaagtac  24780
gccgttccgt tctcagaaga gttactcatc tggtccgatg aagcacaatt cgtcctgact  24840
gcctcgggta ctctcacatc taagtcggtt gagttgaacc taacgaccca gtttgacgta  24900
caggaccgag cgagaccttt tgggattggg cgtaatgtct actttgctag tccgaggtcc  24960
agcttcacgt ccatccacag gtactacgct gtgcaggatg tcagttccgt taagaatgct  25020
gaggacatta catcacacgt tcctaactac atccctaatg tgtgttcag  tatttgcgga  25080 agtggtacgg aaaacttctg ttcggtacta tctcacgggg accctagtaa aatcttcatg  25140
tacaaattcc tgtacctgaa cgaagagtta aggcaacagt cgtggtctca ttgggacttt  25200
ggggaaaacg tacaggttct agcttgtcag agtatcagct cagatatgta tgtgattctt  25260
cgcaatgagt tcaatacgtt cctagctaga atctctttca ctaagaacgc cattgactta  25320
cagggagaac cctatcgtgc ctttatggac atgaagattc gatacacgat tcctagtgga  25380
acatacaacg atgacacatt cactacctct attcatattc caacaattta tggtgcaaac  25440
ttcgggaggg gcaaaatcac tgtattggag cctgatggta agataaccgt gtttgagcaa  25500
cctacggctg ggtggaatag cgaccccttg ctgagactca gcggtaactt ggagggacgc  25560
atggtgtaca ttgggttcaa cattaacttc gtatatgagt tctctaagtt cctcatcaag  25620
cagactgccg acgacgggtc tacctccacg gaagacattg ggcgcttaca gttacgccga  25680
gcgtgggtta actacgagaa ctctggtacg tttgacattt atgttgagaa ccaatcgtct  25740
aactggaagt acacaatggc tggtgcccga ttaggctcta acactctgag gctgggagaa  25800
ctgaacttag ggaccggaca atatcgattc cctgtggttg gtaacgccaa gttcaacact  25860
gtatacatct tgtcagatga gactaccccct ctgaacatca ttgggtgtgg ctgggaaggt  25920
aactacttac ggagaagttc cggtatttaa ttaaatattc tccctgtggt ggctcgaaat  25980
taatacgact cactataggg agaacaatac gactacggga gggttttctt atgatgacta  26040
taagacctac taaaagtaca gactttgagg tattcactcc ggctcaccat gacattcttg  26100
aagctaaggc tgctggtatt gagccgagtt ccctgatgc ttccgagtgt gtcacgttga  26160
gcctctatgg gttccctcta gctatcggtg gtaactgcgg ggaccagtgc tggttcgtta  26220
cgagcgacca agtgtggcga cttagtggaa aggctaagcg aaagttccgt aagttaatca  26280
tggagtatcg cgataagatg cttgagaagt atgatactct ttggaattac gtatgggtag  26340
gcaatacgtc ccacattcgt ttcctcaaga ctatcggtgc ggtattccat gaagagtaca  26400
cacgagatgg tcaatttcag ttatttacaa tcacgaaagg aggataacca tatgtgttgg  26460
gcagccgcaa tacctatcgc tatatctggc gctcaggcta tcagtggtca gaacgctcag  26520
gccaaaatga ttgccgctca gaccgctgct ggtcgtcgtc aagctatgga aatcatgagg  26580
cagacgaaca tccagaatgc tgacctatcg ttgcaagctc gaagtaaact tgaggaagcg  26640
tccgccgagt tgacctcaca gaacatgcag aaggtccaag ctattgggtc tatccgagcg  26700
```

```
gctatcggag agagtatgct tgaaggttcc tcaatggacc gcattaagcg agtcacagaa   26760
ggacagttca ttcgggaagc caatatggta actgagaact atcgccgtga ctaccaagca   26820
atcttcgcac agcaacttgg tggtactcaa agtgctgcaa gtcagattga cgaaatctat   26880
aagagcgaac agaaacagaa gagtaagcta cagatggttc tggacccact ggctatcatg   26940
gggtcttccg ctgcgagtgc ttacgcatcc ggtgcgttcg actctaagtc cacaactaag   27000
gcacctattg ttgccgctaa aggaaccaag acggggaggt aatgagctat gagtaaaatt   27060
gaatctgccc ttcaagcggc acaaccggga ctctctcggt tacgtggtgg tgctggaggt   27120
atgggctatc gtgcagcaac cactcaggcc gaacagccaa ggtcaagcct attggacacc   27180
attggtcggt tcgctaaggc tggtgccgat atgtataccg ctaaggaaca acgagcacga   27240
gacctagctg atgaacgctc taacgagatt atccgtaagc tgacccctga gcaacgtcga   27300
gaagctctca acaacgggac ccttctgtat caggatgacc catacgctat ggaagcactc   27360
cgagtcaaga ctggtcgtaa cgctgcgtat cttgtggacg atgacgttat gcagaagata   27420
aaagagggtg tcttccgtac tcgcgaagag atggaagagt atcgccatag tcgccttcaa   27480
gagggcgcta aggtatacgc tgagcagttc ggcatcgacc ctgaggacgt tgattatcag   27540
cgtggtttca acggggacat taccgagcgt aacatctcgc tgtatggtgc gcatgataac   27600
ttcttgagcc agcaagctca gaagggcgct atcatgaaca gccgagtgga actcaacggt   27660
gtccttcaag accctgatat gctgcgtcgt ccagactctg ctgacttctt tgagaagtat   27720
atcgacaacg gtctggttac tggcgcaatc ccatctgatg ctcaagccac acagcttata   27780
agccaagcgt tcagtgacgc ttctagccgt gctggtggtg ctgacttcct gatgcgagtc   27840
ggtgacaaga aggtaacact taacggagcc actacgactt accgagagtt gattggtgag   27900
gaacagtgga acgctctcat ggtcacagca caacgttctc agtttgagac tgacgcgaag   27960
ctgaacgagc agtatcgctt gaagattaac tctgcgctga accaagagga cccaaggaca   28020
gcttgggaga tgcttcaagg tatcaaggct gaactagata aggtccaacc tgatgagcag   28080
atgacaccac aacgtgagtg gctaatctcc gcacaggaac aagttcagaa tcagatgaac   28140
gcatggacga aagctcaggc caaggctctg gacgattcca tgaagtcaat gaacaaactt   28200
gacgtaatcg acaagcaatt ccagaagcga atcaacggtg agtgggtctc aacggatttt   28260
aaggatatgc cagtcaacga gaacactggt gagttcaagc atagcgatat ggttaactac   28320
gccaataaga agctcgctga gattgacagt atggacattc cagacggtgc caaggatgct   28380
atgaagttga agtaccttca agcggactct aaggacggag cattccgtac agccatcgga   28440
accatggtca ctgacgctgg tcaagagtgg tctgccgctg tgattaacgg taagttacca   28500
gaacgaaccc cagctatgga tgctctgcgc agaatccgca atgctgaccc tcagttgatt   28560
gctgcgctat acccagacca agctgagcta ttcctgacga tggacatgat ggacaagcag   28620
ggtattgacc ctcaggttat tcttgatgcc gaccgactga ctgttaagcg gtccaaagag   28680
caacgctttg aggatgataa agcattcgag tctgcactga atgcatctaa ggctcctgag   28740
attgcccgta tgccagcgtc actgcgcgaa tctgcacgta agatttatga ctccgttaag   28800
tatcgctcgg ggaacgaaag catggctatg gagcagatga ccaagttcct taaggaatct   28860
acctacacgt tcactggtga tgatgttgac ggtgataccg ttggtgtgat tcctaagaat   28920
atgatgcagg ttaactctga cccgaaatca tgggagcaag gtcgggatat tctggaggaa   28980
gcacgtaagg gaatcattgc gagcaaccct tggataacca ataagcaact gaccatgtat   29040
tctcaaggtg actccattta ccttatggac accacaggtc aagtcagagt ccgatacgac   29100
```

```
aaagagttac tctcgaaggt ctggagtgag aaccagaaga aactcgaaga gaaagctcgt   29160
gagaaggctc tggctgatgt gaacaagcga gcacctatag ttgccgctac gaaggccgt    29220 gaagctgctg ctaaacgagt ccgagagaaa cgtaaacaga ctcctaagtt catctacgga   29280
cgtaaggagt aactaaaggc tacataagga ggccctaaat ggataagtac gataagaacg   29340
taccaagtga ttatgatggt ctgttccaaa aggctgctga tgccaacggg gtctcttatg   29400 acctttacg taaagtcgct tggacagaat cacgatttgt gcctacagca aaatctaaga    29460
ctggaccatt aggcatgatg caatttacca aggcaaccgc taaggccctc ggtctgcgag   29520
ttaccgatgg tccagacgac gaccgactga accctgagtt agctattaat gctgccgcta   29580
agcaacttgc aggtctggta gggaagtttg atggcgatga actcaaagct gcccttgcgt   29640
acaaccaagg cgagggacgc ttgggtaatc cacaacttga ggcgtactct aagggagact   29700
tcgcatcaat ctctgaggag ggacgtaact acatgcgtaa ccttctggat gttgctaagt   29760
cacctatggc tggacagttg gaaacttttg gtggcataac cccaaagggt aaaggcattc   29820
cggctgaggt aggattggct ggaattggtc acaagcagaa agtaacacag gaacttcctg   29880
agtccacaag ttttgacgtt aagggtatcg aacaggaggc tacggcgaaa ccattcgcca   29940 aggactttg ggagacccac ggagaaacac ttgacgagta caacagtcgt tcaaccttct    30000
tcggattcaa aaatgctgcc gaagctgaac tctccaactc agtcgctggg atggctttcc   30060
gtgctggtcg tctcgataat ggttttgatg tgtttaaaga caccattacg ccgactcgct   30120
ggaactctca catctggact ccagaggagt tagagaagat tcgaacagag gttaagaacc   30180
ctgcgtacat caacgttgta actggtggtt cccctgagaa cctcgatgac ctcattaaat   30240
tggctaacga gaactttgag aatgactccc gcgctgccga ggctggccta ggtgccaaac   30300
tgagtgctgg tattattggt gctggtgtgg acccgcttag ctatgttcct atggtcggtg   30360
tcactggtaa gggctttaag ttaatcaata aggctcttgt agttggtgcc gaaagtgctg   30420
ctctgaacgt tgcatccgaa ggtctccgta cctccgtagc tggtggtgac gcagactatg   30480
cgggtgctgc cttaggtggc tttgtgtttg gcgcaggcat gtctgcaatc agtgacgctg   30540
tagctgctgg actgaaacgc agtaaaccag aagctgagtt cgacaatgag ttcatcggtc   30600
ctatgatgcg attggaagcc cgtgagacag cacgaaacgc caactctgcg gacctctctc   30660
ggatgaacac tgagaacatg aagtttgaag gtgaacataa tggtgtccct tatgaggact   30720
taccaacaga gagaggtgcc gtggtgttac atgatggctc cgttctaagt gcaagcaacc   30780
caatcaaccc taagactcta aaagagttct ccgaggttga ccctgagaag gctgcgcgag   30840
gaatcaaact ggctgggttc accgagattg gcttgaagac cttggggtct gacgatgctg   30900
acatccgtag agtggctatc gacctcgttc gctctcctac tggtatgcag tctggtgcct   30960
caggtaagtt cggtgcaaca gcttctgaca tccatgagag acttcatggt actgaccagc   31020
gtacttataa tgacttgtac aaagcaatgt ctgacgctat gaaagaccct gagttctcta   31080
ctggcggcgc taagatgtcc cgtgaagaaa ctcgatacac tatctaccgt agagcggcac   31140
tagctattga gcgtccagaa ctacagaagg cactcactcc gtctgagaga atcgttatgg   31200
acatcattaa gcgtcacttt gacaccaagc gtgaacttat ggaaaaccca gcaatattcg   31260
gtaacacaaa ggctgtgagt atcttccctg agagtcgcca caaggtact tacgttcctc    31320 acgtatatga ccgtcatgcc aaggcgctga tgattcaacg ctacggtgcc gaaggtttgc   31380
aggaagggat tgcccgctca tggatgaaca gctacgtctc cagacctgag gtcaaggcca   31440
```

```
gagtcgatga gatgcttaag gaattacacg gggtgaagga agtaacacca gagatggtag    31500
agaagtacgc tatggataag gcttatggta tctcccactc agaccagttc accaacagtt    31560
ccataataga agagaacatt gagggcttag taggtatcga gaataactca ttccttgagg    31620
cacgtaactt gtttgattcg gacctatcca tcactatgcc agacggacag caattctcag    31680
tgaatgacct aagggacttc gatatgttcc gcatcatgcc agcgtatgac cgccgtgtca    31740
atggtgacat cgccatcatg gggtctactg gtaaaaccac taaggaactt aaggatgaga    31800
ttttggctct caaagcgaaa gctgagggag acggtaagaa gactggcgag gtacatgctt    31860
taatggatac cgttaagatt cttactggtc gtgctagacg caatcaggac actgtgtggg    31920
aaacctcact gcgtgccatc aatgacctag ggttcttcgc taagaacgcc tacatgggtg    31980
ctcagaacat tacggagatt gctgggatga ttgtcactgg taacgttcgt gctctagggc    32040
atggtatccc aattctgcgt gatacactct acaagtctaa accagtttca gctaaggaac    32100
tcaaggaact ccatgcgtct ctgttcggga aggaggtgga ccagttgatt cggcctaaac    32160
gtgctgacat tgtgcagcgc ctaagggaag caactgatac cggacctgcc gtggcgaaca    32220
tcgtagggac cttgaagtat tcaacacagg aactggctgc tcgctctccg tggactaagc    32280
tactgaacgg aaccactaac taccttctgg atgctgcgcg tcaaggtatg cttggggatg    32340
ttattagtgc caccctaaca ggtaagacta cccgctggga gaaagaaggc ttccttcgtg    32400
gtgcctccgt aactcctgag cagatggctg gcatcaagtc tctcatcaag gaacatatgg    32460
tacgcggtga ggacgggaag tttaccgtta aggacaagca agcgttctct atggacccac    32520
gggctatgga cttatggaga ctggctgaca aggtagctga tgaggcaatg ctgcgtccac    32580
ataaggtgtc cttacaggat tcccatgcgt tcggagcact aggtaagatg gttatgcagt    32640
ttaagtcttt cactatcaag tcccttaact ctaagttcct gcgaaccttc tatgatggat    32700
acaagaacaa ccgagcgatt gacgctgcgc tgagcatcat cacctctatg ggtctcgctg    32760
gtggtttcta tgctatggct gcacacgtca aagcatacgc tctgcctaag gagaaacgta    32820
aggagtactt ggagcgtgca ctggacccaa ccatgattgc ccacgctgcg ttatctcgta    32880
gttctcaatt gggtgctcct ttggctatgg ttgacctagt tggtggtgtt ttagggttcg    32940
agtcctccaa gatggctcgc tctacgattc tacctaagga caccgtgaag gaacgtgacc    33000
caaacaaacc gtacacctct agagaggtaa tgggcgctat gggttcaaac cttctggaac    33060
agatgccttc ggctggcttt gtggctaacg tagggctac cttaatgaat gctgctggcg    33120
tggtcaactc acctaataaa gcaaccgagc aggacttcat gactggtctt atgaactcca    33180
caaaagagtt agtaccgaac gacccattga ctcaacagct tgtgttgaag atttatgagg    33240
cgaacggtgt taacttgagg gagcgtagga aataatacga ctcactatag ggagaggcga    33300
aataatcttc tccctgtagt ctcttagatt tactttaagg aggtcaaatg gctaacgtaa    33360
ttaaaaccgt tttgacttac cagttagatg gctccaatcg tgattttaat atcccgtttg    33420
agtatctagc ccgtaagttc gtagtggtaa ctcttattgg tgtagaccga aaggtcctta    33480
cgattaatac agactatcgc tttgctacac gtactactat ctctctgaca aaggcttggg    33540
gtccagccga tggctacacg accatcgagt tacgtcgagt aacctccact accgaccgat    33600
tggttgactt tacggatggt tcaatcctcc gcgcgtatga ccttaacgtc gctcagattc    33660
aaacgatgca cgtagcggaa gaggcccgtg acctcactac ggatactatc ggtgtcaata    33720
acgatggtca cttggatgct cgtggtcgtc gaattgtgaa cctagcgaac gccgtggatg    33780
accgcgatgc tgttccgttt ggtcaactaa agaccatgaa ccagaactca tggcaagcac    33840
```

```
gtaatgaagc cttacagttc cgtaatgagg ctgagacttt cagaaaccaa gcggagggct    33900
ttaagaacga gtccagtacc aacgctacga acacaaagca gtggcgcgat gagaccaagg    33960
gtttccgaga cgaagccaag cggttcaaga atacggctgg tcaatacgct acatctgctg    34020
ggaactctgc ttccgctgcg catcaatctg aggtaaacgc tgagaactct gccacagcat    34080
ccgctaactc tgctcatttg gcagaacagc aagcagaccg tgcggaacgt gaggcagaca    34140
agctggaaaa ttacaatgga ttggctggtg caattgataa ggtagatgga accaatgtgt    34200
actggaaagg aaatattcac gctaacgggc gcctttacat gaccacaaac ggttttgact    34260
gtggccagta tcaacagttc tttggtggtg tcactaatcg ttactctgtc atggagtggg    34320
gagatgagaa cggatggctg atgtatgttc aacgtagaga gtggacaaca gcgataggcg    34380
gtaacatcca gttagtagta aacggacaga tcatcaccca aggtggagcc atgaccggtc    34440
agctaaaatt gcagaatggg catgttcttc aattagagtc cgcatccgac aaggcgcact    34500
atattctatc taaagatggt aacaggaata actggtacat tggtagaggg tcagataaca    34560
acaatgactg taccttccac tcctatgtac atggtacgac cttaacactc aagcaggact    34620
atgcagtagt taacaaacac ttccacgtag gtcaggccgt tgtggccact gatggtaata    34680
ttcaaggtac taagtgggga ggtaaatggc tggatgctta cctacgtgac agcttcgttg    34740
cgaagtccaa ggcgtggact caggtgtggt ctggtagtgc tggcggtggg gtaagtgtga    34800
ctgtttcaca ggatctccgc ttccgcaata tctggattaa gtgtgccaac aactcttgga    34860
acttcttccg tactggcccc gatggaatct acttcatagc ctctgatggt ggatggttac    34920
gattccaaat acactccaac ggtctcggat tcaagaatat tgcagacagt cgttcagtac    34980
ctaatgcaat catggtggag aacgagtaat tggtaaatca caaggaaaga cgtgtagtcc    35040
acggatggac tctcaaggag gtacaaggtg ctatcattag actttaacaa cgaattgatt    35100
aaggctgctc caattgttgg gacgggtgta gcagatgtta gtgctcgact gttctttggg    35160
ttaagcctta acgaatggtt ctacgttgct gctatcgcct acacagtggt tcagattggt    35220
gccaaggtag tcgataagat gattgactgg aagaaagcca ataaggagtg atatgtatgg    35280
aaaaggataa gagccttatt acattcttag agatgttgga cactgcgatg gctcagcgta    35340
tgcttgcgga ccttttcggac catgagcgtc gctctccgca actctataat gctattaaca    35400
aactgttaga ccgccacaag ttccagattg gtaagttgca gccggatgtt cacatcttag    35460
gtggccttgc tggtgctctt gaagagtaca agagaaagt cggtgataac ggtcttacgg    35520
atgatgatat ttcacacatta cagtgatata ctcaaggcca ctacagatag tggtctttat    35580
ggatgtcatt gtctatacga gatgctccta cgtgaaatct gaaagttaac gggaggcatt    35640
atgctagaat ttttacgtaa gctaatccct tgggttctcg ctgggatgct attcgggtta    35700
ggatggcatc tagggtcaga ctcaatggac gctaaatgga acaggaggt acacaatgag    35760 tacgttaaga gagttgaggc tgcgaagagc actcaaagag caatcgatgc ggtatctgct    35820
aagtatcaag aagaccttgc cgcgctggaa gggagcactg ataggattat ttctgatttg    35880
cgtagcgaca ataagcggtt gcgcgtcaga gtcaaaacta ccggaaccct cgatggtcag    35940
tgtggattcg agcctgatgg tcgagccgaa cttgacgacc gagatgctaa acgtattctc    36000
gcagtgaccc agaagggtga cgcatggatt cgtgcgttac aggatactat tcgtgaactg    36060
caacgtaagt aggaaatcaa gtaaggaggc aatgtgtcta ctcaatccaa tcgtaatgcg    36120
ctcgtagtgg cgcaactgaa aggagacttc gtggcgttcc tattcgtctt atggaaggcg    36180
```

```
ctaaacctac cggtgcccac taagtgtcag attgacatgg ctaaggtgct ggcgaatgga    36240
gacaacaaga agttcatctt acaggctttc cgtggtatcg gtaagtcgtt catcacatgt    36300
gcgttcgttg tgtggtcctt atggagagac cctcagttga agatacttat cgtatcagcc    36360
tctaaggagc gtgcagacgc taactccatc tttattaaga acatcattga cctgctgcca    36420
ttcctatctg agttaaagcc aagacccgga cagcgtgact cggtaatcag ctttgatgta    36480
ggcccagcca atcctgacca ctctcctagt gtgaaatcag taggtatcac tggtcagtta    36540
actggtagcc gtgctgacat tatcattgcg gatgacgttg agattccgtc taacagcgca    36600
actatgggtg cccgtgagaa gctatggact ctggttcagg agttcgctgc gttacttaaa    36660
ccgctgcctt cctctcgcgt tatctacctt ggtacacctc agacagagat gactctctat    36720
aaggaacttg aggataaccg tgggtacaca accattatct ggcctgctct gtacccaagg    36780
acacgtgaag agaacctcta ttactcacag cgtcttgctc ctatgttacg cgctgagtac    36840
gatgagaacc ctgaggcact tgctgggact ccaacagacc cagtgcgctt tgaccgtgat    36900
gacctgcgcg agcgtgagtt ggaatacggt aaggctggct ttacgctaca gttcatgctt    36960
aaccctaacc ttagtgatgc cgagaagtac ccgctgaggc ttcgtgacgc tatcgtagcg    37020
gccttagact tagagaaggc cccaatgcat taccagtggc ttccgaaccg tcagaacatc    37080
attgaggacc ttcctaacgt tggccttaag ggtgatgacc tgcatacgta ccacgattgt    37140
tccaacaact caggtcagta ccaacagaag attctggtca ttgaccctag tggtcgcggt    37200
aaggacgaaa caggttacgc tgtgctgtac acactgaacg gttacatcta ccttatggaa    37260
gctggaggtt ccgtgatgg ctactccgat aagacccttg agttactcgc taagaaggca    37320
aagcaatggg gagtccagac ggttgtctac gagagtaact tcggtgacgg tatgttcggt    37380
aaggtattca gtcctatcct tcttaaacac cacaactgtg cgatggaaga gattcgtgcc    37440
cgtggtatga aagagatgcg tatttgcgat acccttgagc cagtcatgca gactcaccgc    37500
cttgtaattc gtgatgaggt cattagggcc gactaccagt ccgctcgtga cgtagacggt    37560
aagcatgacg ttaagtactc gttgttctac cagatgaccc gtatcactcg tgagaaaggc    37620
gctctggctc atgatgaccg attggatgcc cttgcgttag gcattgagta tctccgtgag    37680
tccatgcagt tggattccgt taaggtcgag ggtgaagtac ttgctgactt ccttgaggaa    37740
cacatgatgc gtcctacggt tgctgctacg catatcattg agatgtctgt gggaggagtt    37800
gatgtgtact ctgaggacga tgagggttac ggtacgtctt tcattgagtg gtgatttatg    37860
cattaggact gcatagggat gcactataga ccacggatgg tcagttcttt aagttactga    37920
aaagacacga taaattaata cgactcacta tagggagagg agggacgaaa ggttactata    37980
tagatactga atgaatactt atagagtgca taaagtatgc ataatggtgt acctagagtg    38040
acctctaaga atggtgatta tattgtatta gtatcacctt aacttaagga ccaacataaa    38100
gggaggagac tcatgttccg cttattgttg aacctactgc ggcatagagt cacctaccga    38160
tttcttgtgg tactttgtgc tgcccttggg tacgcatctc ttactggaga cctcagttca    38220
ctggagtctg tcgtttgctc tatactcact tgtagcgatt agggtcttcc tgaccgactg    38280
atggctcacc gagggattca gcggtatgat tgcatcacac cacttcatcc ctatagagtc    38340
aagtcctaag gtatacccat aaagagcctc taatggtcta tcctaaggtc tatacctaaa    38400
gataggccat cctatcagtg tcacctaaag agggtcttag agagggccta tggagttcct    38460
atagggtcct ttaaaatata ccataaaaat ctgagtgact atctcacagt gtacggacct    38520
aaagttcccc cataggggt acctaaagcc cagccaatca cctaaagtca accttcggtt    38580
```

```
gaccttgagg gttccctaag ggttggggat gacccttggg tttgtctttg ggtgttacct    38640
tgagtgtctc tctgtgtccc t                                              38661
```

<210> SEQ ID NO 23
<211> LENGTH: 60
<212> TYPE: DNA
<213> ORGANISM: Artificial Sequence
<220> FEATURE:
<223> OTHER INFORMATION: Forward primer

<400> SEQUENCE: 23

```
cttgaagacg aaagggcctc gtgatacgcc tctcacagtg tacggaccta aagttccccc    60
```

<210> SEQ ID NO 24
<211> LENGTH: 30
<212> TYPE: DNA
<213> ORGANISM: Artificial Sequence
<220> FEATURE:
<223> OTHER INFORMATION: Reverse primer

<400> SEQUENCE: 24

```
attacgcgat gacagtagac aacctttccg                                     30
```

<210> SEQ ID NO 25
<211> LENGTH: 30
<212> TYPE: DNA
<213> ORGANISM: Artificial Sequence
<220> FEATURE:
<223> OTHER INFORMATION: Forward primer

<400> SEQUENCE: 25

```
tgcagcaata ccggaaaggt tgtctactgt                                     30
```

<210> SEQ ID NO 26
<211> LENGTH: 30
<212> TYPE: DNA
<213> ORGANISM: Artificial Sequence
<220> FEATURE:
<223> OTHER INFORMATION: Reverse primer

<400> SEQUENCE: 26

```
atatgtctcc tcatagatgt gcctatgtgg                                     30
```

<210> SEQ ID NO 27
<211> LENGTH: 30
<212> TYPE: DNA
<213> ORGANISM: Artificial Sequence
<220> FEATURE:
<223> OTHER INFORMATION: Forward primer

<400> SEQUENCE: 27

```
acttgtgact ccacataggc acatctatga                                     30
```

<210> SEQ ID NO 28
<211> LENGTH: 54
<212> TYPE: DNA
<213> ORGANISM: Artificial Sequence
<220> FEATURE:
<223> OTHER INFORMATION: Reverse primer

<400> SEQUENCE: 28

```
gccccaaggg gttatgctag atttcgaagt ctatcagaag ttcgaatcga ttac          54
```

<210> SEQ ID NO 29

```
<211> LENGTH: 50
<212> TYPE: DNA
<213> ORGANISM: Artificial Sequence
<220> FEATURE:
<223> OTHER INFORMATION: Forward primer

<400> SEQUENCE: 29
cttctgatag acttcgaaat ctagcataac cccttggggc ctctaaacgg          50

<210> SEQ ID NO 30
<211> LENGTH: 30
<212> TYPE: DNA
<213> ORGANISM: Artificial Sequence
<220> FEATURE:
<223> OTHER INFORMATION: Reverse primer

<400> SEQUENCE: 30
gaataacctg agggtcaata ccctgcttgt                                30

<210> SEQ ID NO 31
<211> LENGTH: 30
<212> TYPE: DNA
<213> ORGANISM: Artificial Sequence
<220> FEATURE:
<223> OTHER INFORMATION: Forward primer

<400> SEQUENCE: 31
gacatgatgg acaagcaggg tattgaccct                                30

<210> SEQ ID NO 32
<211> LENGTH: 60
<212> TYPE: DNA
<213> ORGANISM: Artificial Sequence
<220> FEATURE:
<223> OTHER INFORMATION: Reverse primer

<400> SEQUENCE: 32
cataatagaa acgacacgaa attacaaaat agggacacag agagacactc aaggtaacac 60

<210> SEQ ID NO 33
<211> LENGTH: 20
<212> TYPE: DNA
<213> ORGANISM: Artificial Sequence
<220> FEATURE:
<223> OTHER INFORMATION: Promoter

<400> SEQUENCE: 33
taatacgact cactataggg                                           20

<210> SEQ ID NO 34
<211> LENGTH: 79
<212> TYPE: DNA
<213> ORGANISM: Artificial Sequence
<220> FEATURE:
<223> OTHER INFORMATION: Forward primer

<400> SEQUENCE: 34
ccacaacggt ttccctctag aaataatttt gtttaacttt aagaaggaga tataccaatg 60
cgctcatacg atatgaacg                                            79

<210> SEQ ID NO 35
<211> LENGTH: 48
<212> TYPE: DNA
<213> ORGANISM: Artificial Sequence
<220> FEATURE:
<223> OTHER INFORMATION: Reverse primer
```

<400> SEQUENCE: 35
cgttagccat tggtatatct ccttcttta aataccggaa cttctccg 48

<210> SEQ ID NO 36
<211> LENGTH: 50
<212> TYPE: DNA
<213> ORGANISM: Artificial Sequence
<220> FEATURE:
<223> OTHER INFORMATION: Forward primer

<400> SEQUENCE: 36 ccggtatttta aaagaaggag ataccaat ggctaacgta attaaaaccg 50

<210> SEQ ID NO 37
<211> LENGTH: 34
<212> TYPE: DNA
<213> ORGANISM: Artificial Sequence
<220> FEATURE:
<223> OTHER INFORMATION: Reverse primer

<400> SEQUENCE: 37
cccgcggatc cttactcgtt ctccaccatg attg 34

<210> SEQ ID NO 38
<211> LENGTH: 58
<212> TYPE: DNA
<213> ORGANISM: Artificial Sequence
<220> FEATURE:
<223> OTHER INFORMATION: Forward primer

<400> SEQUENCE: 38
cccggaattc gaaattaata cgactcacta tagggagacc acaacggttt ccctctag 58

<210> SEQ ID NO 39
<211> LENGTH: 34
<212> TYPE: DNA
<213> ORGANISM: Artificial Sequence
<220> FEATURE:
<223> OTHER INFORMATION: Reverse primer

<400> SEQUENCE: 39
cccgcggatc cttactcgtt ctccaccatg attg 34

<210> SEQ ID NO 40
<211> LENGTH: 31
<212> TYPE: DNA
<213> ORGANISM: Artificial Sequence
<220> FEATURE:
<223> OTHER INFORMATION: Forward primer

<400> SEQUENCE: 40
cccgcggatc cttattgctc agcggtggca g 31

<210> SEQ ID NO 41
<211> LENGTH: 34
<212> TYPE: DNA
<213> ORGANISM: Artificial Sequence
<220> FEATURE:
<223> OTHER INFORMATION: Reverse primer

<400> SEQUENCE: 41
cccggaattc taatacgact cactataggg agac 34

<210> SEQ ID NO 42

```
<211> LENGTH: 58
<212> TYPE: DNA
<213> ORGANISM: Artificial Sequence
<220> FEATURE:
<223> OTHER INFORMATION: Forward primer

<400> SEQUENCE: 42
cttgaagacg aaagggcctc gtgatacgcc gtccatccta aagccaacac ctaaagcc         58

<210> SEQ ID NO 43
<211> LENGTH: 30
<212> TYPE: DNA
<213> ORGANISM: Artificial Sequence
<220> FEATURE:
<223> OTHER INFORMATION: Reverse primer

<400> SEQUENCE: 43
attacgcgat gacagtagac aacctttccg                                         30

<210> SEQ ID NO 44
<211> LENGTH: 30
<212> TYPE: DNA
<213> ORGANISM: Artificial Sequence
<220> FEATURE:
<223> OTHER INFORMATION: Forward primer

<400> SEQUENCE: 44
tgcagcaata ccggaaaggt tgtctactgt                                         30

<210> SEQ ID NO 45
<211> LENGTH: 30
<212> TYPE: DNA
<213> ORGANISM: Artificial Sequence
<220> FEATURE:
<223> OTHER INFORMATION: Reverse primer

<400> SEQUENCE: 45
atatgtctcc tcatagatgt gcctatgtgg                                         30

<210> SEQ ID NO 46
<211> LENGTH: 30
<212> TYPE: DNA
<213> ORGANISM: Artificial Sequence
<220> FEATURE:
<223> OTHER INFORMATION: Forward primer

<400> SEQUENCE: 46
acttgtgact ccacataggc acatctatga                                         30

<210> SEQ ID NO 47
<211> LENGTH: 30
<212> TYPE: DNA
<213> ORGANISM: Artificial Sequence
<220> FEATURE:
<223> OTHER INFORMATION: Reverse primer

<400> SEQUENCE: 47
gaataacctg agggtcaata ccctgcttgt                                         30

<210> SEQ ID NO 48
<211> LENGTH: 30
<212> TYPE: DNA
<213> ORGANISM: Artificial Sequence
<220> FEATURE:
<223> OTHER INFORMATION: Forward primer

<400> SEQUENCE: 48
```

```
gacatgatgg acaagcaggg tattgaccct                                        30

<210> SEQ ID NO 49
<211> LENGTH: 58
<212> TYPE: DNA
<213> ORGANISM: Artificial Sequence
<220> FEATURE:
<223> OTHER INFORMATION: Reverse primer

<400> SEQUENCE: 49
cataatagaa acgacacgaa attacaaaat tgcataaatc accactcaat gaaagacg        58

<210> SEQ ID NO 50
<211> LENGTH: 38932
<212> TYPE: DNA
<213> ORGANISM: Artificial Sequence
<220> FEATURE:
<223> OTHER INFORMATION: Phage genome with PAC sites deletion

<400> SEQUENCE: 50
gtccatccta aagccaacac ctaaagccta cacctaaaga cccatcaagt caacgcctat        60
cttaaagttt aaacataaag accagaccta aagaccagac ctaaagacac tacataaaga       120
ccagacctaa agacgccttg ttgttagcca taaagtgata acctttaatc attgtcttta       180
ttaatacaac tcactataag gagagacaac ttaaagagac ttaaaagatt aatttaaaat       240
ttatcaaaaa gagtattgac ttaaagtcta acctatagga tacttacagc catcgagagg       300
gacacggcga atagccatcc caatcgacac cggggtcaac cggataagta dacagcctga       360
taagtcgcac gaaaaacagg tattgacaac atgaagtaac atgcagtaag atacaaatcg       420
ctaggtaaca ctagcagcgt caaccgggcg cacagtgcct tctaggtgac ttaagcgcac       480
cacggcacat aaggtgaaac aaaacggttg acaacatgaa gtaaacacgg tacgatgtac       540
cacatgaaac gacagtgagt caccacactg aaaggtgatg cggtctaacg aaacctgacc       600
taagacgctc tttaacaatc tggtaaatag ctcttgagtg catgactagc ggataactca       660
agggtatcgc aaggtgccct ttatgatatt cactaataac tgcacgaggt aacacaagat       720
ggctatgtct aacatgactt acaacaacgt tttcgaccac gcttacgaaa tgctgaaaga       780
aaacatccgt tatgatgaca tccgtgacac tgatgacctg cacgatgcta ttcacatggc       840
tgccgataat gcagttccgc actactacgc tgacatcttt agcgtaatgg caagtgaggg       900
cattgacctt gagttcgaag actctggtct gatgcctgac accaaggacg taatccgcat       960
cctgcaagcg cgtatctatg agcaattaac gattgacctc tgggaagacg cagaagactt      1020
gctcaatgaa tacttggagg aagtcgagga gtacgaggag gatgaagagt aatgtctact      1080
accaacgtgc aatacggtct gaccgctcaa actgtacttt tctatagcga catggtgcgc      1140
tgtggcttta actggtcact cgcaatggca cagctcaaag aactgtacga aaacaacaag      1200
gcaatagctt tagaatctgc tgagtgatag actcaaggtc gctcctagcg agtggccttt      1260
atgattatca ctttacttat gagggagtaa tgtatatgct tactatcggt ctactcaccg      1320
ctctaggtct agctgtaggt gcatcctttg ggaaggcttt aggtgtagct gtaggttcct      1380
actttaccgc ttgcatcatc ataggaatca tcaaggggc actacgcaaa tgatgaagca      1440
ctacgttatg ccaatccaca cgtccaacgg ggcaaccgta tgtacacctg atgggttcgc      1500
aatgaaacaa cgaatcgaac gccttaagcg tgaactccgc attaaccgca agattaacaa      1560
gataggttcc ggctatgaca gaacgcactg atggcttaaa gaaaggttat atgcccaatg      1620
```

```
gcacactata cgctgcaaat cggcgaatag tgagaacttg gcgagagaac aacctcgaac   1680
gccgcaagga caagagaggg cggcgtggca tagacgaaag gaaaaggtta aagccaagaa   1740
actcgccgca cttgaacagg cactagccaa cacactgaac gctatctcat aacgaacata   1800
aaggacacaa tgcaatgaac attaccgaca tcatgaacgc tatcgacgca atcaaagcac   1860
tgccaatctg tgaacttgac aagcgtcaag gtatgcttat cgacttactg gtcgagatgg   1920
tcaacagcga gacgtgtgat ggcgagctaa ccgaactaaa tcaggcactt gagcatcaag   1980
attggtggac taccttgaag tgtctcacgg ctgacgcagg gttcaagatg ctcggtaatg   2040
gtcacttctc ggctgcttat agtcacccgc tgctacctaa cagagtgatt aaggtgggct   2100
ttaagaaaga ggattcaggc gcagcctata ccgcattctg ccgcatgtat cagggtcgtc   2160
ctggtatccc taacgtctac gatgtacagc gccacgctgg atgctatacg gtggtacttg   2220
acgcacttaa ggattgcgag cgtttcaaca atgatgccca ttataaatac gctgagattg   2280
caagcgacat cattgattgc aattcggatg agcatgatga gttaactgga tgggatggtg   2340
agtttgttga aacttgtaaa ctaatccgca agttctttga gggcatcgcc tcattcgaca   2400
tgcatagcgg gaacatcatg ttctcaaatg gagacgtacc atacatcacc gacccggtat   2460
cattctcgca gaagaaagac ggtggcgcat tcagcatcga ccctgaggaa ctcatcaagg   2520
aagtcgagga agtcgcacga cagaaagaaa ttgaccgcgc taaggcccgt aaagaacgtc   2580
acgaggggcg cttagaggca cgcagattca aacgtcgcaa ccgcaaggca cgtaaagcac   2640
acaaagctaa gcgcgaaaga atgcttgctg cgtggcgatg ggctgaacgt caagaacggc   2700
gtaaccatga ggtagctgta gatgtactag gaagaaccaa taacgctatg ctctgggtca   2760
acatgttctc tggggacttt aaggcgcttg aggaacgaat cgcgctgcac tggcgtaatg   2820
ctgaccggat ggctatcgct aatggtctta cgctcaacat tgataagcaa cttgacgcaa   2880
tgttaatggg ctgatagtct tatcttacag gtcatctgcg ggtggcctga ataggtacga   2940
tttactaact ggaagaggca ctaaatgaac acgattaaca tcgctaagaa cgacttctct   3000
gacatcgaac tggctgctat cccgttcaac actctggctg accattacgg tgagcgttta   3060
gctcgcgaac agttggccct tgagcatgag tcttacgaga tgggtgaagc acgcttccgc   3120
aagatgtttg agcgtcaact taaagctggt gaggttgcgg ataacgctgc cgccaagcct   3180
ctcatcacta ccctactccc taagatgatt gcacgcatca cgactggttt tgaggaagtg   3240
aaagctaagc gcggcaagcg cccgacagcc ttccagttcc tgcaagaaat caagccggaa   3300
gccgtagcgt acatcaccat taagaccact ctggcttgcc taaccagtgc tgacaataca   3360
accgttcagg ctgtagcaag cgcaatcggt cgggccattg aggacgaggc tcgcttcggt   3420
cgtatccgtg accttgaagc taagcacttc aagaaaaacg ttgaggaaca actcaacaag   3480
cgcgtagggc acgtctacaa gaaagcattt atgcaagttg tcgaggctga catgctctct   3540
aagggtctac tcggtggcga ggcgtggtct tcgtggcata aggaagactc tattcatgta   3600
ggagtacgct gcatcgagat gctcattgag tcaaccggaa tggttagctt acaccgccaa   3660
aatgctggcg tagtaggtca agactctgag actatcgaac tcgcacctga atacgctgag   3720
gctatcgcaa cccgtgcagg tgcgctggct ggcatctctc cgatgttcca accttgcgta   3780
gttcctccta agccgtggac tggcattact ggtggtggct attgggctaa cggtcgtcgt   3840
cctctggcgc tggtgcgtac tcacagtaag aaagcactga tgcgctacga agacgtttac   3900
atgcctgagg tgtacaaagc gattaacatt gcgcaaaaca ccgcatgaa atcaacaag   3960 aaagtcctag cggtcgccaa cgtaatcacc aagtggaagc attgtccggt cgaggacatc   4020
```

```
cctgcgattg agcgtgaaga actcccgatg aaaccggaag acatcgacat gaatcctgag    4080
gctctcaccg cgtggaaacg tgctgccgct gctgtgtacc gcaaggacaa ggctcgcaag    4140
tctcgccgta tcagccttga gttcatgctt gagcaagcca ataagtttgc taaccataag    4200
gccatctggt tcccttacaa catggactgg cgcggtcgtg tttacgctgt gtcaatgttc    4260
aacccgcaag gtaacgatat gaccaaagga ctgcttacgc tggcgaaagg taaaccaatc    4320
ggtaaggaag gttactactg gctgaaaatc cacggtgcaa actgtgcggg tgtcgataag    4380
gttccgttcc ctgagcgcat caagttcatt gaggaaaacc acgagaacat catggcttgc    4440
gctaagtctc cactggagaa cacttggtgg gctgagcaag attctccgtt ctgcttcctt    4500
gcgttctgct ttgagtacgc tggggtacag caccacggcc tgagctataa ctgctccctt    4560
ccgctggcgt ttgacgggtc ttgctctggc atccagcact tctccgcgat gctccgagat    4620
gaggtaggtg gtcgcgcggt taacttgctt cctagtgaaa ccgttcagga catctacggg    4680
attgttgcta agaaagtcaa cgagattcta caagcagacg caatcaatgg gaccgataac    4740
gaagtagtta ccgtgaccga tgagaacact ggtgaaatct ctgagaaagt caagctgggc    4800
actaaggcac tggctggtca atggctggct tacggtgtta ctcgcagtgt gactaagcgt    4860
tcagtcatga cgctggctta cgggtccaaa gagttcggct tccgtcaaca agtgctggaa    4920
gataccattc agccagctat tgattccggc aagggtctga tgttcactca gccgaatcag    4980
gctgctggat acatggctaa gctgatttgg gaatctgtga gcgtgacggt ggtagctgcg    5040
gttgaagcaa tgaactggct taagtctgct gctaagctgc tggctgctga ggtcaaagat    5100
aagaagactg gagagattct tcgcaagcgt tgcgctgtgc attgggtaac tcctgatggt    5160
ttccctgtgt ggcaggaata caagaagcct attcagacgc gcttgaacct gatgttcctc    5220
ggtcagttcc gcttacagcc taccattaac accaacaaag atagcgagat tgatgcacac    5280
aaacaggagt ctggtatcgc tcctaacttt gtacacagcc aagacggtag ccaccttcgt    5340
aagactgtag tgtgggcaca cgagaagtac ggaatcgaat cttttgcact gattcacgac    5400
tccttcggta ccattccggc tgacgctgcg aacctgttca agcagtgcg cgaaactatg    5460
gttgacacat atgagtcttg tgatgtactg gctgatttct acgaccagtt cgctgaccag    5520
ttgcacgagt ctcaattgga caaaatgcca gcacttccgg ctaaaggtaa cttgaacctc    5580
cgtgacatct tagagtcgga cttcgcgttc gcgtaacgcc aaatcaatac gactcactat    5640
agagggacaa actcaaggtc attcgcaaga gtggcctta tgattgacct tcttccggtt    5700
aatacgactc actataggag aaccttaagg tttaacttta agaccctta gtgttaatta    5760
gagatttaaa ttaaagaatt actaagagag gactttaagt atgcgtaact tcgaaaagat    5820
gaccaaacgt tctaaccgta atgctcgtga cttcgaggca accaaggtc gcaagttgaa    5880
taagactaag cgtgaccgct ctcacaagcg tagctgggag ggtcagtaag atgggacgtt    5940
tatatagtgg taatctggca gcattcaagg cagcaacaaa caagctgttc cagttagact    6000
tagcggtcat ttatgatgac tggtatgatg cctatacaag aaaagattgc atacggttac    6060
gtattgagga caggagtgga aacctgattg atactagcac cttctaccac cacgacgagg    6120
acgttctgtt caatatgtgt actgattggt tgaaccatat gtatgaccag ttgaaggact    6180
ggaagtaata cgactcagta tagggacaat gcttaaggtc gctctctagg agtggcctta    6240
gtcatttaac caataggaga taaacattat gatgaacatt aagactaacc cgtttaaagc    6300
cgtgtctttc gtagagtctg ccattaagaa ggctctggat aacgctgggt atcttatcgc    6360
```

```
tgaaatcaag tacgatggtg tacgcgggaa catctgcgta gacaatactg ctaacagtta    6420
ctggctctct cgtgtatcta aaacgattcc ggcactggag cacttaaacg ggtttgatgt    6480
tcgctggaag cgtctactga acgatgaccg ttgcttctac aaagatggct ttatgcttga    6540
tggggaactc atggtcaagg gcgtagactt aacacaggg tccggcctac tgcgtaccaa     6600
atggactgac acgaagaacc aagagttcca tgaagagtta ttcgttgaac caatccgtaa    6660
gaaagataaa gttccctta agctgcacac tggacacctt cacataaaac tgtacgctat     6720
cctcccgctg cacatcgtgg agtctggaga agactgtgat gtcatgacgt tgctcatgca    6780
ggaacacgtt aagaacatgc tgcctctgct acaggaatac ttccctgaaa tcgaatggca    6840
agcggctgaa tcttacgagg tctacgatat ggtagaacta cagcaactgt acgagcagaa    6900
gcgagcagaa ggccatgagg gtctcattgt gaaagaccg atgtgtatct ataagcgcgg     6960
taagaaatct ggctggtgga aaatgaaacc tgagaacgaa gctgacggta tcattcaggg    7020
tctggtatgg ggtacaaaag gtctggctaa tgaaggtaaa gtgattggtt ttgaggtgct    7080
tcttgagagt ggtcgtttag ttaacgccac gaatatctct cgcgccttaa tggatgagtt    7140
cactgagaca gtaaaagagg ccaccctaag tcaatgggga ttcttttagcc catacggtat    7200
tggcgacaac gatgcttgta ctattaaccc ttacgatggc tgggcgtgtc aaattagcta    7260
catggaggaa acacctgatg gctctttgcg gcacccatcg ttcgtaatgt tccgtggcac    7320
cgaggacaac cctcaagaga aaatgtaatc acactggctc accttcgggt gggccttttct   7380
gcgtttataa ggagacactt tatgtttaag aaggttggta aattccttgc ggctttggca    7440
gctatcctga cgcttgcgta tattcttgcg gtataccctc aagtagcact agtagtagtt    7500
ggcgcttgtt acttagcggc agtgtgtgct tgcgtgtgga gtatagttaa ctggtaatac    7560
gactcactaa aggaggtaca caccatgatg tacttaatgc cattactcat cgtcattgta    7620
ggatgccttg cgctccactg tagcgatgat gatatgccag atggtcacgc ttaatacgac    7680
tcactaaagg agacactata tgtttcgact tcattacaac aaaagcgtta agaatttcac    7740
ggttcgccgt gctgaccgtt caatcgtatg tgcgagcgag cgccgagcta agatacctct    7800
tattggtaac acagttcctt tggcaccgag cgtccacatc attatcaccc gtggtgactt    7860
tgagaaagca atagacaaga aacgtccggt tcttagtgtg gcagtgaccc gcttcccgtt    7920
cgtccgtctg ttactcaaac gaatcaagga ggtgttctga tgggactgtt agatggtgaa    7980
gcctgggaaa aagaaaaccc gccagtacaa gcaactgggt gtatagcttg cttagagaaa    8040
gatgaccgtt atccacacac ctgtaacaaa ggagctaacg atatgaccga acgtgaacaa    8100
gagatgatca ttaagttgat agacaataat gaaggtcgcc cagatgattt gaatggctgc    8160
ggtattctct gctccaatgt cccttgccac ctctgccccg caaataacga tcaaaagata    8220
accttaggtg aaatccgagc gatggaccca cgtaaaccac atctgaataa acctgaggta    8280
actcctacag atgaccagcc ttccgctgag acaatcgaag gtgtcactaa gccttcccac    8340
tacatgctgt ttgacgacat tgaggctatc gaagtgattg ctcgttcaat gaccgttgag    8400
cagttcaagg gatactgctt cggtaacatc ttaaagtaca gactacgtgc tggtaagaag    8460
tcagagttag cgtacttaga gaaagaccta gcgaaagcag acttctataa agaactcttt    8520
gagaaacata aggataaatg ttatgcataa cttcaagtca accccacctg ccgacagcct    8580
atctgatgac ttcacatctt gctcagagtg gtgccgaaag atgtgggaag agacattcga    8640
cgatgcgtac atcaagctgt atgaactttg gaaatcgaga ggtcaatgac tatgtcaaac    8700
gtaaatacag gttcacttag tgtggacaat aagaagtttt gggctaccgt agagtcctcg    8760
```

```
gagcattcct tcgaggttcc aatctacgct gagaccctag acgaagctct ggagttagcc   8820
gaatggcaat acgttccggc tggctttgag gttactcgtg tgcgtccttg tgtagcaccg   8880
aagtaatacg actcactatt agggaagact ccctctgaga aaccaaacga aacctaaagg   8940
agattaacat tatggctaag aagattttca cctctgcgct gggtaccgct gaaccttacg   9000
cttacatcgc caagccggac tacggcaacg aagagcgtgg ctttgggaac cctcgtggtg   9060
tctataaagt tgacctgact attcccaaca agacccgcg ctgccagcgt atggtcgatg    9120
aaatcgtgaa gtgtcacgaa gaggcttatg ctgctgccgt tgaggaatac gaagctaatc   9180
cacctgctgt agctcgtggt aagaaaccgc tgaaaccgta tgagggtgac atgccgttct   9240
tcgataacgg tgacggtacg actaccttta agttcaaatg ctacgcgtct ttccaagaca   9300
agaagaccaa agagaccaag cacatcaatc tggttgtggt tgactcaaaa ggtaagaaga   9360
tggaagacgt tccgattatc ggtggtggct ctaagctgaa agttaaatat tctctggttc   9420
catacaagtg gaacactgct gtaggtgcga gcgttaagct gcaactggaa tccgtgatgc   9480
tggtcgaact ggctaccttt ggtggcggtg aagacgattg ggctgacgaa gttgaagaga   9540
acggctatgt tgcctctggt tctgccaaag cgagcaaacc acgcgacgaa gaaagctggg   9600
acgaagacga cgaagagtcc gaggaagcag acgaagacgg agacttctaa gtggaactgc   9660
gggagaaaat ccttgagcga atcaaggtga cttcctctgg gtgttgggag tggcagggcg   9720
ctacgaacaa taaagggtac gggcaggtgt ggtgcagcaa taccggaaag gttgtctact   9780
gtcatcgcgt aatgtctaat gctccgaaag gttctaccgt cctgcactcc tgtgataatc   9840
cattatgttg taaccctgaa cacctatcca taggaactcc aaaagagaac tccactgaca   9900
tggtaaataa gggtcgctca cacaaggggt ataaactttc agacgaagac gtaatggcaa   9960
tcatggagtc cagcgagtcc aatgtatcct tagctcgcac ctatggtgtc tcccaacaga  10020
ctatttgtga tatacgcaaa gggaggcgac atggcaggtt acggcgctaa aggaatccga  10080
aaggttggag cgtttcgctc tggcctagag gacaaggttt caaagcagtt ggaatcaaaa  10140
ggtattaaat tcgagtatga agagtggaaa gtgccttatg taattccggc gagcaatcac  10200
acttacactc cagacttctt acttccaaac ggtatattcg ttgagacaaa gggtctgtgg  10260
gaaagcgatg atagaaagaa gcacttatta attagggagc agcaccccga gctagacatc  10320
cgtattgtct tctcaagctc acgtactaag ttatacaaag gttctccaac gtcttatgga  10380
gagttctgcg aaaagcatgg tattaagttc gctgataaac tgatacctgc tgagtggata  10440
aaggaaccca agaaggaggt ccccttttgat agattaaaaa ggaaaggagg aaagaaataa  10500
tggctcgtgt acagttttaaa caacgtgaat ctactgacgc aatctttgtt cactgctcgg  10560
ctaccaagcc aagtcagaat gttggtgtcc gtgagattcg ccagtggcac aaagagcagg  10620
gttggctcga tgtgggatac cactttatca tcaagcgaga cggtactgtg gaggcaggac  10680
gagatgagat ggctgtaggc tctcacgcta agggttacaa ccacaactct atcggcgtct  10740
gccttgttgg tggtatcgac gataaaggta agttcgacgc taactttacg ccagcccaaa  10800
tgcaatccct tcgctcactg cttgtcacac tgctggctaa gtacgaaggc gctgtgcttc  10860
gcgcccatca tgaggtggcg ccgaaggctt gcccttcgtt cgaccttaag cgttggtggg  10920
agaagaacga actggtcact tctgaccgtg gataattaat tgaactcact aaagggagac  10980
cacagcggtt tcccttttgtt cgcattggag gtcaaataat gcgcaagtct tataaacaat  11040
tctataaggc tccgaggagg catatccaag tgtgggaggc agccaatggg cctataccaa  11100
```

```
aaggttatta tatagaccac attgacggca atccactcaa cgacgcctta gacaatctcc   11160
gtctggctct cccaaaagaa aactcatgga acatgaagac tccaaagagc aatacctcag   11220
gactaaaggg actgagttgg agcaaggaaa gggagatgtg gagaggcact gtaacagctg   11280
agggtaaaca gcataacttt cgtagtagag atctattgga agtcgttgcg tggatttata   11340
gaactaggag ggaattgcat ggacaattcg cacgattccg atagtgtatt tctttaccac   11400
attccttgtg acaactgtgg gagtagtgat gggaactcgc tgttctctga cggacacacg   11460
ttctgctacg tatgcgagaa gtggactgct ggtaatgaag acactaaaga gagggcttca   11520
aaacggaaac cctcaggagg taaaccaatg acttacaacg tgtggaactt cggggaatcc   11580
aatggacgct actccgcgtt aactgcgaga ggaatctcca aggaaacctg tcagaaggct   11640
ggctactgga ttgccaaagt agacggtgtg atgtaccaag tggctgacta tcgggaccag   11700
aacggcaaca ttgtgagtca aaggttcga gataaagata agaactttaa gaccactggt   11760
agtcacaaga gtgacgctct gttcgggaag cacttgtgga atggtggtaa gaagattgtc   11820
gttacagaag gtgaaatcga catgcttacc gtgatgaac ttcaagactg taagtatcct   11880
gtagtgtcgt tgggtcacgg tgcctctgcc gctaagaaga catgcgctgc caactacgaa   11940
tactttgacc agttcgaaca gattatctta atgttcgata tggacgaagc agggcgcaaa   12000
gcagtcgaag aggctgcaca ggttctacct gctggtaagg tacgagtggc agttcttccg   12060
tgtaaggatg caaacgagtg tcacctaaat ggtcacgacc gtgaaatcat ggagcaagtg   12120
tggaatgctg gtccttggat tctgatggt gtggtatcgg ctctttcgtt acgtgaacga   12180
atccgtgagc acctatcgtc cgaggaatca gtaggttac ttttcagtgg ctgcactggt   12240
atcaacgata agaccttagg tgcccgtggt ggtgaagtca ttatggtcac ttccggttcc   12300
ggtatgggta agtcaacgtt cgtccgtcaa caagctctac aatggggcac agcgatgggc   12360
aagaaggtag gcttagcgat gcttgaggag tccgttgagg agaccgctga ggaccttata   12420
ggtctacaca accgtgtccg actgagacaa tccgactcac taaagagaga gattattgag   12480
aacggtaagt tcgaccaatg gttcgatgaa ctgttcggca acgatacgtt ccatctatat   12540
gactcattcg ccgaggctga gacggataga ctgctcgcta agctggccta catgcgctca   12600
ggcttgggct gtgacgtaat cattctagac cacatctcaa tcgtcgtatc cgcttctggt   12660
gaatccgatg agcgtaagat gattgacaac ctgatgacca agctcaaagg gttcgctaag   12720
tcaactgggg tggtgctggt cgtaatttgt caccttaaga acccagacaa aggtaaagca   12780
catgaggaag gtcgcccccgt ttctattact gacctacgtg gttctggcgc actacgccaa   12840
ctatctgata ctattattgc ccttgagcgt aatcagcaag gcgatatgcc taaccttgtc   12900
ctcgttcgta ttctcaagtg ccgctttact ggtgatactg gtatcgctgg ctacatggaa   12960
tacaacaagg aaaccggatg gcttgaacca tcaagttact caggggaaga agagtcacac   13020
tcagagtcaa cagactggtc caacgacact gacttctgac aggattcttg atgactttcc   13080
agacgactac gagaagtttc gctggagagt cccattctaa tacgactcac taaaggagac   13140
acaccatgtt caaactgatt aagaagttag gccaactgct ggttcgtatg tacaacgtgg   13200
aagccaagcg actgaacgat gaggctcgta agaggccac acagtcacgc gctctggcga   13260
ttcgctccaa cgaactggct gacagtgcat ccactaaagt taccgaggct gcccgtgtgg   13320
caaaccaagc tcaacagctt tccaaattct ttgagtaatc aaacaggaga aaccattatg   13380
tctaacgtag ctgaaactat ccgtctatcc gatacagctg accagtggaa ccgtcgagtc   13440
cacatcaacg ttcgcaacgg taaggcgact atggtttacc gctggaagga ctctaagtcc   13500
```

```
tctaagaatc acactcagcg tatgacgttg acagatgagc aagcactgcg tctggtcaat   13560
gcgcttacca aagctgccgt gacagcaatt catgaagctg gtcgcgtcaa tgaagctatg   13620
gctatcctcg acaagattga taactaagag tggtatcctc aaggtcgcca aagtggtggc   13680
cttcatgaat actattcgac tcactatagg agatattacc atgcgtgacc ctaaagttat   13740
ccaagcagaa atcgctaaac tggaagctga actggaggac gttaagtacc atgaagctaa   13800
gactcgctcc gctgttcaca tcttgaagaa cttaggctgg acttggacaa gacagactgg   13860
ctggaagaaa ccagaagtta ccaagctgag tcataaggtg ttcgataagg acactatgac   13920
ccacatcaag gctggtgatt gggttaaggt tgacatggga gttgttggtg gatacggcta   13980
cgtccgctca gttagtggca aatatgcaca agtgtcatac atcacaggtg ttactccacg   14040
cggtgcaatc gttgccgata agaccaacat gattcacaca ggtttcttga cagttgtttc   14100
atatgaagag attgttaagt cacgataatc aataggagaa atcaatatga tcgtttctga   14160
catcgaagct aacgccctct tagagagcgt cactaagttc cactgcgggg ttatctacga   14220
ctactccacc gctgagtacg taagctaccg tccgagtgac ttcggtgcgt atctggatgc   14280
gctggaagcc gaggttgcac gaggcggtct tattgtgttc cacaacggtc acaagtatga   14340
cgttcctgca ttgaccaaac tggcaaagtt gcaattgaac cgagagttcc accttcctcg   14400
tgagaactgt attgacaccc ttgtgttgtc acgtttgatt cattccaacc tcaaggacac   14460
cgatatgggt cttctgcgtt ccggcaagtt gcccggaaaa cgctttgggt ctcacgcttt   14520
ggaggcgtgg ggttatcgct taggcgagat gaagggtgaa tacaaagacg actttaagcg   14580
tatgcttgaa gagcagggtg aagaatacgt tgacggaatg gagtggtgga acttcaacga   14640
agagatgatg gactataacg ttcaggacgt tgtggtaact aaagctctcc ttgagaagct   14700
actctctgac aaacattact tccctcctga gattgacttt acggacgtag atacactac   14760 gttctggtca gaatcccttg aggccgttga cattgaacat cgtgctgcat ggctgctcgc   14820
taaacaagag cgcaacgggt tcccgtttga cacaaaagca atcgaagagt tgtacgtaga   14880
gttagctgct cgccgctctg agttgctccg taaattgacc gaaacgttcg gctcgtggta   14940
tcagcctaaa ggtggcactg agatgttctg ccatccgcga acaggtaagc cactacctaa   15000
ataccctcgc attaagacac ctaaagttgg tggtatcttt aagaagccta agaacaaggc   15060
acagcgagaa ggccgtgagc cttgcgaact tgatacccgc gagtacgttg ctggtgctcc   15120
ttacacccca gttgaacatg ttgtgtttaa cccttcgtct cgtgaccaca ttcagaagaa   15180
actccaagag gctgggtggg tcccgaccaa gtacaccgat aagggtgctc ctgtggtgga   15240
cgatgaggta ctcgaaggag tacgtgtaga tgaccctgag aagcaagccg ctatcgacct   15300
cattaaagag tacttgatga ttcagaagcg aatcggacag tctgctgagg gagacaaagc   15360
atggcttcgt tatgttgctg aggatggtaa gattcatggt tctgttaacc ctaatggagc   15420
agttacgggt cgtgcgaccc atgcgttccc aaaccttgcg caaattccgg tgtacgttc   15480 tccttatgga gagcagtgtc gcgctgcttt tggcgctgag caccatttgg atgggataac   15540
tggtaagcct tgggttcagg ctggcatcga cgcatccggt cttgagctac gctgcttggc   15600
tcacttcatg gctcgctttg ataacggcga gtacgctcac gagattctta acggcgacat   15660
ccacactaag aaccagatag ctgctgaact acctacccga gataacgcta agacgttcat   15720
ctatgggttc ctctatggtg ctggtgatga gaagattgga cagattgttg gtgctggtaa   15780
agagcgcggt aaggaactca agaagaaatt ccttgagaac accccgcga ttgcagcact   15840
```

```
ccgcgagtct atccaacaga cacttgtcga gtcctctcaa tgggtagctg gtgagcaaca   15900
agtcaagtgg aaacgccgct ggattaaagg tctggatggt cgtaaggtac acgttcgtag   15960
tcctcacgct gccttgaata ccctactgca atctgctggt gctctcatct gcaaactgtg   16020
gattatcaag accgaagaga tgctcgtaga gaaaggcttg aagcatggct gggatgggga   16080
ctttgcgtac atggcatggg tacatgatga atccaagta ggctgccgta ccgaagagat   16140
tgctcaggtg gtcattgaga ccgcacaaga agcgatgcgc tgggttggag accactggaa   16200
cttccggtgt cttctggata ccgaaggtaa gatgggtcct aattgggcga tttgccactg   16260
atacaggagg ctactcatga acgaaagaca cttaacaggt gctgcttctg aaatgctagt   16320
agcctacaaa tttaccaaag ctgggtacac tgtctattac cctatgctga ctcagagtaa   16380
agaggacttg gttgtatgta aggatggtaa atttagtaag gttcaggtta aaacagccac   16440
aacggttcaa accaacacag gagatgccaa gcaggttagg ctaggtggat gcggtaggtc   16500
cgaatataag gatggagact ttgacattct tgcggttgtg gttgacgaag atgtgcttat   16560
tttcacatgg gacgaagtaa aaggtaagac atccatgtgt gtcggcaaga gaaacaaagg   16620
cataaaacta taggagaaat tattatggct atgacaaaga aatttaaagt gtccttcgac   16680
gttaccgcaa agatgtcgtc tgacgttcag gcaatcttag agaaagatat gctgcatcta   16740
tgtaagcagg tcggctcagg tgcgattgtc cccaatggta aacagaagga aatgattgtc   16800
cagttcctga cacacggtat ggaaggattg atgacattcg tagtacgtac atcatttcgt   16860
gaggccatta aggacatgca cgaagagtat gcagataagg actctttcaa acaatctcct   16920
gcaacagtac gggaggtgtt ctgatgtctg actacctgaa agtgctgcaa gcaatcaaaa   16980
gttgccctaa gactttccag tccaactatg tacggaacaa tgcgagcctc gtagcggagg   17040
ccgcttcccg tggtcacatc tcgtgcctga ctactagtgg acgtaacggt ggcgcttggg   17100
aaatcactgc ttccggtact cgctttctga acgaatggg aggatgtgtc taatgtctcg   17160
tgaccttgtg actattccac gcgatgtgtg gaacgatata cagggctaca tcgactctct   17220
ggaacgtgag aacgatagcc ttaagaatca actaatggaa gctgacgaat acgtagcgga   17280
actagaggag aaacttaatg gcacttcttg accttaaaca attctatgag ttacgtgaag   17340
gctgcgacga caagggtatc cttgtgatgg acggcgactg gctggtcttc caagctatga   17400
gtgctgctga gtttgatgcc tcttgggagg aagagatttg gcaccgatgc tgtgaccacg   17460
ctaaggcccg tcagattctt gaggattcca ttaagtccta cgagacccgt aagaaggctt   17520
gggcaggtgc tccaattgtc cttgcgttca ccgatagtgt taactggcgt aaagaactgg   17580
ttgacccgaa ctataaggct aaccgtaagg ccgtgaagaa acctgtaggg tactttgagt   17640
tccttgatgc tctctttgag cgcgaagagt tctattgcat ccgtgagcct atgcttgagg   17700
gtgatgacgt tatgggagtt attgcttcca atccgtctgc cttcggtgct cgtaaggctg   17760
taatcatctc ttgcgataag gactttaaga ccatccctaa ctgtgacttc ctgtggtgta   17820
ccactggtaa catcctgact cagaccgaag agtccgctga ctggtggcac ctcttccaga   17880
ccatcaaggg tgacatcact gatggttact cagggattgc tggatggggt gataccgccg   17940
aggacttctt gaataacccg ttcataaccg agcctaaaac gtctgtgctt aagtccgta   18000 agaacaaagg ccaagaggtt actaaatggg ttaaacgcga ccctgagcct catgagacgc   18060
tttgggactg cattaagtcc attggcgcga aggctggtat gaccgaagag gatattatca   18120
agcagggcca aatggctcga atcctacggt tcaacgagta caactttatt gacaaggaga   18180
tttacctgtg gagaccgtag cgtatattgg tctgggtctt tgtgttctcg gagtgtgcct   18240
```

```
catttcgtgg ggcctttggg acttagccag aataatcaag tcgttacacg acactaagtg   18300
ataaactcaa ggtccctaaa ttaatacgac tcactatagg gagatagggg cctttacgat   18360
tattacttta agatttaact ctaagaggaa tctttattat gttaacacct attaaccaat   18420
tacttaagaa ccctaacgat attccagatg tacctcgtgc aaccgctgag tatctacagg   18480
ttcgattcaa ctatgcgtac ctcgaagcgt ctggtcatat aggacttatg cgtgctaatg   18540
gttgtagtga ggcccacatc ttgggtttca ttcagggcct acagtatgcc tctaacgtca   18600
ttgacgagat tgagttacgc aaggaacaac taagagatga tggggaggat tgacactatg   18660
tgtttctcac cgaaaattaa aactccgaag atggatacca atcagattcg agccgttgag   18720
ccagcgcctc tgacccaaga agtgtcaagc gtggagttcg gtgggtcttc tgatgagacg   18780
gataccgagg gcaccgaagt gtctggacgc aaaggcctca aggtcgaacg tgatgattcc   18840
gtagcgaagt ctaaagccag cggcaatggc tccgctcgta tgaaatcttc catccgtaag   18900
tccgcatttg gaggtaagaa gtgatgtctg agttcacatg tgtggaggct aagagtcgct   18960
tccgtgcaat ccggtggact gtggaacacc ttgggttgcc taaaggattc gaaggacact   19020
ttgtgggcta cagcctctac gtagacgaag tgatggacat gtctggttgc cgtgaagagt   19080
acattctgga ctctaccgga aaacatgtag cgtacttcgc gtggtgcgta agctgtgaca   19140
ttcaccacaa aggagacatt ctggatgtaa cgtccgttgt cattaatcct gaggcagact   19200
ctaagggctt acagcgattc ctagcgaaac gctttaagta ccttgcggaa ctccacgatt   19260
gcgattgggt gtctcgttgt aagcatgaag gcgagacaat gcgtgtatac tttaaggagg   19320
tataagttat gggtaagaaa gttaagaagg ccgtgaagaa agtcaccaag tccgttaaga   19380
aagtcgttaa ggaaggggct cgtccggtta acaggttgc tggcggtcta gctggtctgg   19440
ctggtggtac tggtgaagca cagatggtgg aagtaccaca agctgccgca cagattgttg   19500
acgtacctga aaagaggtt tccactgagg acgaagcaca gacagaaagc ggacgcaaga   19560
aagctcgtgc tggcggtaag aaatccttga gtgtagcccg tagctccggt ggcggtatca   19620
acatttaatc aggaggttat cgtggaagac tgcattgaat ggaccggagg tgtcaactct   19680
aagggttatg gtcgtaagtg ggttaatggt aaacttgtga ctccacatag gcacatctat   19740
gaggagacat atggtccagt tccaacagga attgtggtga tgcatatctg cgataaccct   19800
aggtgctata acataaagca ccttacgctt ggaactccaa aggataattc cgaggacatg   19860
gttaccaaag gtagacaggc taaaggagag gaactaagca agaaacttac agagtcagac   19920
gttctcgcta tacgctcttc aaccttaagc caccgctcct taggagaact gtatggagtc   19980
agtcaatcaa ccataacgcg aatactacag cgtaagacat ggagacacat ttaatggctg   20040
agaaacgaac aggacttgcg gaggatggcg caaagtctgt ctatgagcgt ttaaagaacg   20100
accgtgctcc ctatgagaca cgcgctcaga attgcgctca atataccatc ccatcattgt   20160
tccctaagga ctccgataac gcctctacag attatcaaac tccgtggcaa gccgtgggcg   20220
ctcgtggtct gaacaatcta gcctctaagc tcatgctggc tctattccct atgcagactt   20280
ggatgcgact tactatatct gaatatgaag caaagcagtt actgagcgac cccgatggac   20340
tcgctaaggt cgatgagggc ctctcgatgg tagagcgtat catcatgaac tacattgagt   20400
ctaacagtta ccgcgtgact ctctttgagg ctctcaaaca gttagtcgta gctggtaacg   20460
tcctgctgta cctaccggaa ccggaagggt caaactataa tcccatgaag ctgtaccgat   20520
tgtcttctta tgtggtccaa cgagacgcat tcggcaacgt tctgcaaatg gtgactcgtg   20580
```

```
accagatagc tttttggtgct ctccctgagg acatccgtaa ggctgtagaa ggtcaaggtg    20640
gtgagaagaa agctgatgag acaatcgacg tgtacactca catctatctg gatgaggact    20700
caggtgaata cctccgatac gaagaggtcg agggtatgga agtccaaggc tccgatggga    20760
cttatcctaa agaggcttgc ccatacatcc cgattcggat ggtcagacta gatggtgaat    20820
cctacggtcg ttcgtacatt gaggaatact taggtgactt acggtccctt gaaaatctcc    20880
aagaggctat cgtcaagatg tccatgatta gctctaaggt tatcggctta gtgaatcctg    20940
ctggtatcac ccagccacgc cgactgacca aagctcagac tggtgacttc gttactggtc    21000
gtccagaaga catctcgttc ctccaactgg agaagcaagc agactttact gtagctaaag    21060
ccgtaagtga cgctatcgag gctcgccttt cgtttgcctt tatgttgaac tctgcggttc    21120
agcgtacagg tgaacgtgtg accgccgaag agattcggta tgtagcttct gaacttgaag    21180
atactttagg tggtgtctac tctatccttt ctcaagaatt acaattgcct ctggtacgag    21240
tgctcttgaa gcaactacaa gccacgcaac agattcctga gttacctaag gaagccgtag    21300
agccaaccat tagtacaggt ctggaagcaa ttggtcgagg acaagacctt gataagctgg    21360
agcggtgtgt cactgcgtgg gctgcactgg cacctatgcg ggacgaccct gatattaacc    21420
ttgcgatgat taagttacgt attgccaacg ctatcggtat tgacacttct ggtattctac    21480
tcaccgaaga acagaagcaa cagaagatgg cccaacagtc tatgcaaatg ggtatggata    21540
atggtgctgc tgcgctggct caaggtatgg ctgcacaagc tacagcttca cctgaggcta    21600
tggctgctgc cgctgattcc gtaggtttac agccgggaat ttaatacgac tcactatagg    21660
gagacctcat ctttgaaatg agcgatgaca agaggttgga gtcctcggtc ttcctgtagt    21720
tcaactttaa ggagacaata ataatggctg aatctaatgc agacgtatat gcatcttttg    21780
gcgtgaactc cgctgtgatg tctggtggtt ccgttgagga acatgagcag aacatgctgg    21840
ctcttgatgt tgctgcccgt gatggcgatg atgcaatcga gttagcgtca gacgaagtgg    21900
aaacagaacg tgacctgtat gacaactctg acccgttcgg tcaagaggat gacgaaggcc    21960
gcattcaggt tcgtatcggt gatggctctg agccgaccga tgtggacact ggagaagaag    22020
gcgttgaggg caccgaaggt tccgaagagt ttaccccact gggcgagact ccagaagaac    22080
tggtagctgc ctctgagcaa cttggtgagc acgaagaggg cttccaagag atgattaaca    22140
ttgctgctga gcgtggcatg agtgtcgaga ccattgaggc tatccagcgt gagtacgagg    22200
agaacgaaga gttgtccgcc gagtcctacg ctaagctggc tgaaattggc tacacgaagg    22260
ctttcattga ctcgtatatc cgtggtcaag aagctctggt ggagcagtac gtaaacagtg    22320
tcattgagta cgctggtggt cgtgaacgtt ttgatgcact gtataaccac cttgagacgc    22380
acaaccctga ggctgcacag tcgctggata atgcgttgac caatcgtgac ttagcgaccg    22440
ttaaggctat catcaacttg gctggtgagt ctcgcgctaa ggcgttcggt cgtaagccaa    22500
ctcgtagtgt gactaatcgt gctattccgg ctaaacctca ggctaccaag cgtgaaggct    22560
ttgcggaccg tagcgagatg attaaagcta tgagtgaccc tcggtatcgc acagatgcca    22620
actatcgtcg tcaagtcgaa cagaaagtaa tcgattcgaa cttctgatag acttcgaaat    22680
taatacgact cactataggg agaccacaac ggtttccctc tagaaataat tttgtttaac    22740
tttaagaagg agatatacat atggctagca tgactggtgg acagcaaatg ggtactaacc    22800
aaggtaaagg tgtagttgct gctggagata aactggcgtt gttcttgaag gtatttggcg    22860
gtgaagtcct gactgcgttc gctcgtacct ccgtgaccac ttctcgccac atggtacgtt    22920
ccatctccag cggtaaatcc gctcagttcc ctgttctggg tcgcactcag gcagcgtatc    22980
```

```
tggctccggg cgagaacctc gacgataaac gtaaggacat caaacacacc gagaaggtaa   23040
tcaccattga cggtctcctg acggctgacg ttctgattta tgatattgag gacgcgatga   23100
accactacga cgttcgctct gagtatacct ctcagttggg tgaatctctg gcgatggctg   23160
cggatggtgc ggttctggct gagattgccg gtctgtgtaa cgtggaaagc aaatataatg   23220
agaacatcga gggcttaggt actgctaccg taattgagac cactcagaac aaggccgcac   23280
ttaccgacca agttgcgctg ggtaaggaga ttattgcggc tctgactaag gctcgtgcgg   23340
ctctgaccaa gaactatgtt ccggctgctg accgtgtgtt ctactgtgac ccagatagct   23400
actctgcgat tctggcagca ctgatgccga acgcagcaaa ctacgctgct ctgattgacc   23460
ctgagaaggg ttctatccgc aacgttatgg gctttgaggt tgtagaagtt ccgcacctca   23520
ccgctggtgg tgctggtacc gctcgtgagg gcactactgg tcagaagcac gtcttccctg   23580
ccaataaagg tgagggtaat gtcaaggttg ctaaggacaa cgttatcggc ctgttcatgc   23640
accgctctgc ggtaggtact gttaagctgc gtgacttggc tctggagcgc gctcgccgtg   23700
ctaacttcca agcggaccag attatcgcta agtacgcaat gggccacggt ggtcttcgcc   23760
cagaagctgc tggtgcagtg gttttcaaag tggagtaatg ctgggggtgg cctcaacggt   23820
cgctgctagt cccgaagagg cgagtgttac ttcaacagaa gaaaccttaa cgccagcaca   23880
ggaggccgca cgcaccccgc gctgctaaca agcccgaaag gaagctgagt tggctgctgc   23940
caccgctgag caataactag cataacccct tggggcctct aaacgggtct tgagggtttt   24000
tttgctgaaa ggaggaacta tatgcgctca tacgatatga acgttgagac tgccgctgag   24060
ttatcagctg tgaacgacat tctggcgtct atcggtgaac ctccggtatc aacgctggaa   24120
ggtgacgcta acgcagatgc agcgaacgct cggcgtattc tcaacaagat taaccgacag   24180
attcaatctc gtggatggac gttcaacatt gaggaaggca taacgctact acctgatgtt   24240
tactccaacc tgattgtata cagtgacgac tatttatccc taatgtctac ttccggtcaa   24300
tccatctacg ttaaccgagg tggctatgtg tatgaccgaa cgagtcaatc agaccgcttt   24360
gactctggta ttactgtgaa cattattcgt ctccgcgact acgatgagat gcctgagtgc   24420
ttccgttact ggattgtcac caaggcttcc cgtcagttca caaccgatt ctttggggca   24480 ccggaagtag agggtgtact ccaagaagag gaagatgagg ctagacgtct ctgcatggag   24540
tatgagatgg actacggtgg gtacaatatg ctggatgag atgcgttcac ttctggtcta   24600
ctgactcgct aacattaata aataaggagg ctctaatggc actcattagc caatcaatca   24660
agaacttgaa gggtggtatc agccaacagc ctgacatcct tcgttatcca gaccaagggt   24720
cacgccaagt taacggttgg tcttcggaga ccgagggcct ccaaaagcgt ccacctcttg   24780
ttttcttaaa tacacttgga gacaacggtg cgttaggtca agctccgtac atccacctga   24840
ttaaccgaga tgagcacgaa cagtattacg ctgtgttcac tggtagcgga atccgagtgt   24900
tcgacctttc tggtaacgag aagcaagtta ggtatcctaa cggttccaac tacatcaaga   24960
ccgctaatcc acgtaacgac ctgcgaatgg ttactgtagc agactatacg ttcatcgtta   25020
accgtaacgt tgttgcacag aagaacacaa agtctgtcaa cttaccgaat tacaacccta   25080
atcaagacgg attgattaac gttcgtggtg gtcagtatgg tagggaacta attgtacaca   25140
ttaacggtaa agacgttgcg aagtataaga taccagatgg tagtcaacct gaacacgtaa   25200
acaatacgga tgcccaatgg ttagctgaag agttagccaa gcagatgcgc actaacttgt   25260
ctgattggac tgtaaatgta gggcaagggt tcatccatgt gaccgcacct agtggtcaac   25320
```

```
agattgactc cttcacgact aaagatggct acgcagacca gttgattaac cctgtgaccc    25380
actacgctca gtcgttctct aagctgccac ctaatgctcc taacggctac atggtgaaaa    25440
tcgtagggga cgcctctaag tctgccgacc agtattacgt tcggtatgac gctgagcgga    25500
aagtttggac tgagactta ggttggaaca ctgaggacca agttctatgg gaaaccatgc     25560
cacacgctct tgtgcgagcc gctgacggta atttcgactt caagtggctt gagtggtctc    25620
ctaagtcttg tggtgacgtt gacaccaacc cttggccttc ttttgttggt tcaagtatta    25680
acgatgtgtt cttcttccgt aaccgcttag gattccttag tggggagaac atcatattga    25740
gtcgtacagc caaatacttc aacttctacc ctgcgtccat tgcgaacctt agtgatgacg    25800
accctataga cgtagctgtg agtaccaacc gaatagcaat ccttaagtac gccgttccgt    25860
tctcagaaga gttactcatc tggtccgatg aagcacaatt cgtcctgact gcctcgggta    25920
ctctcacatc taagtcggtt gagttgaacc taacgaccca gtttgacgta caggaccgag    25980
cgagaccttt tgggattggg cgtaatgtct actttgctag tccgaggtcc agcttcacgt    26040
ccatccacag gtactacgct gtgcaggatg tcagttccgt taagaatgct gaggacatta    26100
catcacacgt tcctaactac atccctaatg gtgtgttcag tatttgcgga agtggtacgg    26160
aaaacttctg ttcggtacta tctcacgggg accctagtaa aatcttcatg tacaaattcc    26220
tgtacctgaa cgaagagtta aggcaacagt cgtggtctca ttgggactt ggggaaaacg      26280 tacaggttct agcttgtcag agtatcagct cagatatgta tgtgattctt cgcaatgagt    26340
tcaatacgtt cctagctaga atctctttca ctaagaacgc cattgactta cagggagaac    26400
cctatcgtgc ctttatggac atgaagattc gatacacgat tcctagtgga acatacaacg    26460
atgacacatt cactacctct attcatattc caacaattta tggtgcaaac ttcgggaggg    26520
gcaaaatcac tgtattggag cctgatggta agataaccgt gtttgagcaa cctacggctg    26580
ggtggaatag cgacccttgg ctgagactca gcggtaactt ggagggacgc atggtgtaca    26640
ttgggttcaa cattaacttc gtatatgagt tctctaagtt cctcatcaag cagactgccg    26700
acgacgggtc tacctccacg gaagacattg gccgcttaca gttacgccga gcgtgggtta    26760
actacgagaa ctctggtacg tttgacattt atgttgagaa ccaatcgtct aactggaagt    26820
acacaatggc tggtgcccga ttaggctcta acactctgag ggctgggaga ctgaacttag    26880
ggaccggaca atatcgattc cctgtggttg gtaacgccaa gttcaacact gtatacatct    26940
tgtcagatga gactacccct ctgaacatca ttgggtgtgg ctgggaaggt aactacttac    27000
ggagaagttc cggtatttaa ttaaatattc tccctgtggt ggctcgaaat taatacgact    27060
cactataggg agaacaatac gactacggga gggttttctt atgatgacta taagacctac    27120
taaaagtaca gactttgagg tattcactcc ggctcaccat gacattcttg aagctaaggc    27180
tgctggtatt gagccgagtt ccctgatgc ttccgagtgt gtcacgttga gcctctatgg     27240
gttccctcta gctatcggtg gtaactgcgg ggaccagtgc tggttcgtta cgagcgacca    27300
agtgtggcga cttagtggaa aggctaagcg aaagttccgt aagttaatca tggagtatcg    27360
cgataagatg cttgagaagt atgatactct ttggaattac gtatgggtag caatacgtc     27420 ccacattcgt ttcctcaaga ctatcggtgc ggtattccat gaagagtaca cacgagatgc    27480
tcaatttcag ttatttacaa tcacgaaagg aggataacca tatgtgttgg gcagccgcaa    27540
tacctatcgc tatatctggc gctcaggcta tcagtggtca gaacgctcag gccaaaatga    27600
ttgccgctca gaccgctgct ggtcgtcgtc aagctatgga aatcatgagg cagacgaaca    27660
tccagaatgc tgacctatcg ttgcaagctc gaagtaaaact tgaggaagcg tccgccgagt   27720
```

```
tgacctcaca gaacatgcag aaggtccaag ctattgggtc tatccgagcg gctatcggag   27780
agagtatgct tgaaggttcc tcaatggacc gcattaagcg agtcacagaa ggacagttca   27840
ttcgggaagc caatatggta actgagaact atcgccgtga ctaccaagca atcttcgcac   27900
agcaacttgg tggtactcaa agtgctgcaa gtcagattga cgaaatctat aagagcgaac   27960
agaaacagaa gagtaagcta cagatggttc tggacccact ggctatcatg gggtcttccg   28020
ctgcgagtgc ttacgcatcc ggtgcgttcg actctaagtc cacaactaag gcacctattg   28080
ttgccgctaa aggaaccaag acggggaggt aatgagctat gagtaaaatt gaatctgccc   28140
ttcaagcggc acaaccggga ctctctcggt tacgtggtgg tgctggaggt atgggctatc   28200
gtgcagcaac cactcaggcc gaacagccaa ggtcaagcct attggacacc attggtcggt   28260
tcgctaaggc tggtgccgat atgtataccg ctaaggaaca acgagcacga gacctagctg   28320
atgaacgctc taacgagatt atccgtaagc tgaccgctga gcaacgtcga gaagctctca   28380
acaacgggac ccttctgtat caggatgacc catacgctat ggaagcactc cgagtcaaga   28440
ctggtcgtaa cgctgcgtat cttgtggacg atgacgttat gcagaagata aagagggtg    28500 tcttccgtac tcgcgaagag atggaagagt atcgccatag tcgccttcaa gagggcgcta   28560
aggtatacgc tgagcagttc ggcatcgacc ctgaggacgt tgattatcag cgtggtttca   28620
acggggacat taccgagcgt aacatctcgc tgtatggtgc gcatgataac ttcttgagcc   28680
agcaagctca gaagggcgct atcatgaaca gccgagtgga actcaacggt gtccttcaag   28740
accctgatat gctgcgtcgt ccagactctg ctgacttctt tgagaagtat atcgacaacg   28800
gtctggttac tggcgcaatc ccatctgatg ctcaagccac acagcttata agccaagcgt   28860
tcagtgacgc ttctagccgt gctggtggtg ctgacttcct gatgcgagtc ggtgacaaga   28920
aggtaacact taacggagcc actacgactt accgagagtt gattggtgag gaacagtgga   28980
acgctctcat ggtcacagca caacgttctc agtttgagac tgacgcgaag ctgaacgagc   29040
agtatcgctt gaagattaac tctgcgctga accaagagga cccaaggaca gcttgggaga   29100
tgcttcaagg tatcaaggct gaactagata aggtccaacc tgatgagcag atgacaccac   29160
aacgtgagtg gctaatctcc gcacaggaac aagttcagaa tcagatgaac gcatggacga   29220
aagctcaggc caaggctctg gacgattcca tgaagtcaat gaacaaactt gacgtaatcg   29280
acaagcaatt ccagaagcga atcaacggtg agtgggtctc aacggatttt aaggatatgc   29340
cagtcaacga gaacactggt gagttcaagc atagcgatat ggttaactac gccaataaga   29400
agctcgctga gattgacagt atggacattc cagacggtgc caaggatgct atgaagttga   29460
agtaccttca agcggactct aaggacggag cattccgtac agccatcgga accatggtca   29520
ctgacgctgg tcaagagtgg tctgccgctg tgattaacgg taagttacca gaacgaaccc   29580
cagctatgga tgctctgcgc agaatccgca atgctgaccc tcagttgatt gctgcgctat   29640
acccagacca agctgagcta ttcctgacga tggacatgat ggacaagcag ggtattgacc   29700
ctcaggttat tcttgatgcc gaccgactga ctgttaagcg gtccaaagag caacgctttg   29760
aggatgataa agcattcgag tctgcactga atgcatctaa ggctcctgag attgcccgta   29820
tgccagcgtc actgcgcgaa tctgcacgta agatttatga ctccgttaag tatcgctcgg   29880
ggaacgaaag catggctatg gagcagatga ccaagttcct taaggaatct acctacacgt   29940
tcactggtga tgatgttgac ggtgataccg ttggtgtgat tcctaagaat atgatgcagg   30000
ttaactctga cccgaaatca tgggagcaag gtcgggatat tctggaggaa gcacgtaagg   30060
```

```
gaatcattgc gagcaaccct tggataacca ataagcaact gaccatgtat tctcaaggtg   30120
actccattta ccttatggac accacaggtc aagtcagagt ccgatacgac aaagagttac   30180
tctcgaaggt ctggagtgag aaccagaaga aactcgaaga gaaagctcgt gagaaggctc   30240
tggctgatgt gaacaagcga gcacctatag ttgccgctac gaaggcccgt gaagctgctg   30300
ctaaacgagt ccgagagaaa cgtaaacaga ctcctaagtt catctacgga cgtaaggagt   30360
aactaaaggc tacataagga ggccctaaat ggataagtac gataagaacg taccaagtga   30420
ttatgatggt ctgttccaaa aggctgctga tgccaacggg gtctcttatg acctttacg    30480
taaagtcgct tggacagaat cacgatttgt gcctacagca aaatctaaga ctggaccatt   30540
aggcatgatg caatttacca aggcaaccgc taaggccctc ggtctgcgag ttaccgatgg   30600
tccagacgac gaccgactga accctgagtt agctattaat gctgccgcta agcaacttgc   30660
aggtctggta gggaagtttg atggcgatga actcaaagct gcccttgcgt acaaccaagg   30720
cgagggacgc ttgggtaatc cacaacttga ggcgtactct aagggagact tcgcatcaat   30780
ctctgaggag ggacgtaact acatgcgtaa ccttctggat gttgctaagt cacctatggc   30840
tggacagttg gaaacttttg gtggcataac cccaaagggt aaaggcattc cggctgaggt   30900
aggattggct ggaattggtc acaagcagaa agtaacacag gaacttcctg agtccacaag   30960
ttttgacgtt aagggtatcg aacaggaggc tacggcgaaa ccattcgcca aggactttg    31020
ggagacccac ggagaaacac ttgacgagta caacagtcgt tcaaccttct tcggattcaa   31080
aaatgctgcc gaagctgaac tctccaactc agtcgctggg atggctttcc gtgctggtcg   31140
tctcgataat ggttttgatg tgtttaaaga caccattacg ccgactcgct ggaactctca   31200
catctggact ccagaggagt tagagaagat tcgaacagag gttaagaacc ctgcgtacat   31260
caacgttgta actggtggtt cccctgagaa cctcgatgac ctcattaaat tggctaacga   31320
gaactttgag aatgactccc gcgctgccga ggctggccta ggtgccaaac tgagtgctgg   31380
tattattggt gctggtgtgg acccgcttag ctatgttcct atggtcggtg tcactggtaa   31440
gggctttaag ttaatcaata aggctcttgt agttggtgcc gaaagtgctg ctctgaacgt   31500
tgcatccgaa ggtctccgta cctccgtagc tggtggtgac gcagactatg cgggtgctgc   31560
cttaggtggc tttgtgtttg gcgcaggcat gtctgcaatc agtgacgctg tagctgctgg   31620
actgaaacgc agtaaaccag aagctgagtt cgacaatgag ttcatcggtc ctatgatgcg   31680
attggaagcc cgtgagacag cacgaaacgc caactctgcg gacctctctc ggatgaacac   31740
tgagaacatg aagtttgaag gtgaacataa tggtgtccct tatgaggact taccaacaga   31800
gagaggtgcc gtggtgttac atgatggctc cgttctaagt gcaagcaacc caatcaaccc   31860
taagactcta aaagagttct ccgaggttga ccctgagaag gctgcgcgag gaatcaaact   31920
ggctgggttc accgagattg gcttgaagac cttggggtct gacgatgctg acatccgtag   31980
agtggctatc gacctcgttc gctctcctac tggtatgcag tctggtgcct caggtaagtt   32040
cggtgcaaca gcttctgaca tccatgagag acttcatggt actgaccagc gtacttataa   32100
tgacttgtac aaagcaatgt ctgacgctat gaaagaccct gagttctcta ctggcggcgc   32160
taagatgtcc cgtgaagaaa ctcgatacac tatctaccgt agagcggcac tagctattga   32220
gcgtccagaa ctacagaagg cactcactcc gtctgagaga atcgttatgg acatcattaa   32280
gcgtcacttt gacaccaagc gtgaacttat ggaaaaccca gcaatattcg gtaacacaaa   32340
ggctgtgagt atcttccctg agagtcgcca caaaggtact tacgttcctc acgtatatga   32400
ccgtcatgcc aaggcgctga tgattcaacg ctacggtgcc gaaggtttgc aggaagggat   32460
```

```
tgcccgctca tggatgaaca gctacgtctc cagacctgag gtcaaggcca gagtcgatga   32520
gatgcttaag gaattacacg gggtgaagga agtaacacca gagatggtag agaagtacgc   32580
tatggataag gcttatggta tctcccactc agaccagttc accaacagtt ccataataga   32640
agagaacatt gagggcttag taggtatcga gaataactca ttccttgagg cacgtaactt   32700
gtttgattcg gacctatcca tcactatgcc agacggacag caattctcag tgaatgacct   32760
aagggacttc gatatgttcc gcatcatgcc agcgtatgac cgccgtgtca atggtgacat   32820
cgccatcatg gggtctactg gtaaaaccac taaggaactt aaggatgaga ttttggctct   32880
caaagcgaaa gctgagggag acggtaagaa gactggcgag gtacatgctt taatggatac   32940
cgttaagatt cttactggtc gtgctagacg caatcaggac actgtgtggg aaacctcact   33000
gcgtgccatc aatgacctag ggttcttcgc taagaacgcc tacatgggtg ctcagaacat   33060
tacggagatt gctgggatga ttgtcactgg taacgttcgt gctctagggc atggtatccc   33120
aattctgcgt gatacactct acaagtctaa accagtttca gctaaggaac tcaaggaact   33180
ccatgcgtct ctgttcggga aggaggtgga ccagttgatt cggcctaaac gtgctgacat   33240
tgtgcagcgc ctaagggaag caactgatac cggacctgcc gtggcgaaca tcgtagggac   33300
cttgaagtat tcaacacagg aactggctgc tcgctctccg tggactaagc tactgaacgg   33360
aaccactaac taccttctgg atgctgcgcg tcaaggtatg cttggggatg ttattagtgc   33420
caccctaaca ggtaagacta cccgctggga gaaagaaggc ttccttcgtg gtgcctccgt   33480
aactcctgag cagatggctg gcatcaagtc tctcatcaag gaacatatgg tacgcggtga   33540
ggacgggaag tttaccgtta aggacaagca agcgttctct atggacccac gggctatgga   33600
cttatggaga ctggctgaca aggtagctga tgaggcaatg ctgcgtccac ataaggtgtc   33660
cttacaggat tcccatgcgt tcggagcact aggtaagatg gttatgcagt ttaagtcttt   33720
cactatcaag tcccttaact ctaagttcct gcgaaccttc tatgatggat acaagaacaa   33780
ccgagcgatt gacgctgcgc tgagcatcat cacctctatg ggtctcgctg gtggtttcta   33840
tgctatggct gcacacgtca aagcatacgc tctgcctaag gagaaacgta aggagtactt   33900
ggagcgtgca ctggacccaa ccatgattgc ccacgctgcg ttatctcgta gttctcaatt   33960
gggtgctcct ttggctatgg ttgacctagt tggtggtgtt ttagggttcg agtcctccaa   34020
gatggctcgc tctacgattc tacctaagga caccgtgaag gaacgtgacc caaacaaacc   34080
gtacacctct agagaggtaa tgggcgctat gggttcaaac cttctggaac agatgccttc   34140
ggctggcttt gtggctaacg tagggctac cttaatgaat gctgctggcg tggtcaactc   34200
acctaataaa gcaaccgagc aggacttcat gactggtctt atgaactcca caaaagagtt   34260
agtaccgaac gacccattga ctcaacagct tgtgttgaag atttatgagg cgaacggtgt   34320
taacttgagg gagcgtagga ataatacgca ctcactatag ggagaggcga ataatcttc   34380 tccctgtagt ctcttagatt tactttaagg aggtcaaatg gctaacgtaa ttaaaaccgt   34440
tttgacttac cagttagatg gctccaatcg tgatttaat atcccgtttg agtatctagc   34500
ccgtaagttc gtagtggtaa ctcttattgg tgtagaccga aaggtcctta cgattaatac   34560
agactatcgc tttgctacac gtactactat ctctctgaca aaggcttggg gtccagccga   34620
tggctacacg accatcgagt tacgtcgagt aacctccact accgaccgat tggttgactt   34680
tacggatggt tcaatcctcc gcgcgtatga ccttaacgtc gctcagattc aaacgatgca   34740
cgtagcggaa gaggcccgtg acctcactac ggatactatc ggtgtcaata acgatggtca   34800
```

```
cttggatgct cgtggtcgtc gaattgtgaa cctagcgaac gccgtggatg accgcgatgc   34860
tgttccgttt ggtcaactaa agaccatgaa ccagaactca tggcaagcac gtaatgaagc   34920
cttacagttc cgtaatgagg ctgagacttt cagaaaccaa gcggagggct ttaagaacga   34980
gtccagtacc aacgctacga acacaaagca gtggcgcgat gagaccaagg gtttccgaga   35040
cgaagccaag cggttcaaga atacggctgg tcaatacgct acatctgctg ggaactctgc   35100
ttccgctgcg catcaatctg aggtaaacgc tgagaactct gccacagcat ccgctaactc   35160
tgctcatttg gcagaacagc aagcagaccg tgcggaacgt gaggcagaca agctggaaaa   35220
ttacaatgga ttggctggtg caattgataa ggtagatgga accaatgtgt actgaaaagg   35280
aaatattcac gctaacgggc gcctttacat gaccacaaac ggttttgact gtggccagta   35340
tcaacagttc tttggtggtg tcactaatcg ttactctgtc atggagtggg gagatgagaa   35400
cggatggctg atgtatgttc aacgtagaga gtggacaaca gcgataggcg gtaacatcca   35460
gttagtagta aacggacaga tcatcaccca aggtggagcc atgaccggtc agctaaaatt   35520
gcagaatggg catgttcttc aattagagtc cgcatccgac aaggcgcact atattctatc   35580
taaagatggt aacaggaata actggtacat tggtagaggg tcagataaca acaatgactg   35640
taccttccac tcctatgtac atggtacgac cttaacactc aagcaggact atgcagtagt   35700
taacaaacac ttccacgtag gtcaggccgt tgtggccact gatggtaata ttcaaggtac   35760
taagtgggga ggtaaatggc tggatgctta cctacgtgac agcttcgttg cgaagtccaa   35820
ggcgtggact caggtgtggt ctggtagtgc tggcggtggg gtaagtgtga ctgtttcaca   35880
ggatctccgc ttccgcaata tctggattaa gtgtgccaac aactcttgga acttcttccg   35940
tactggcccc gatggaatct acttcatagc ctctgatggt ggatggttac gattccaaat   36000
acactccaac ggtctcggat tcaagaatat tgcagacagt cgttcagtac ctaatgcaat   36060
catggtggag aacgagtaat tggtaaatca caaggaaaga cgtgtagtcc acggatggac   36120
tctcaaggag gtacaaggtg ctatcattag acttttaacaa cgaattgatt aaggctgctc   36180
caattgttgg gacgggtgta gcagatgtta gtgctcgact gttctttggg ttaagcctta   36240
acgaatggtt ctacgttgct gctatcgcct acacagtggt tcagattggt gccaaggtag   36300
tcgataagat gattgactgg aagaaagcca ataaggagtg atatgtatgg aaaaggataa   36360 gagcctatt acattcttag agatgttgga cactgcgatg gctcagcgta tgcttgcgga   36420
cctttcggac catgagcgtc gctctccgca actctataat gctattaaca aactgttaga   36480
ccgccacaag ttccagattg gtaagttgca gccggatgtt cacatcttag gtggccttgc   36540
tggtgctctt gaagagtaca aagagaaagt cggtgataac ggtcttacgg atgatgatat   36600
ttacacatta cagtgatata ctcaaggcca ctacagatag tggtctttat ggatgtcatt   36660
gtctatacga gatgctccta cgtgaaatct gaaagttaac gggaggcatt atgctagaat   36720
ttttacgtaa gctaatccct tgggttctcg ctgggatgct attcgggtta ggatggcatc   36780
tagggtcaga ctcaatggac gctaaatgga aacaggaggt acacaatgag tacgttaaga   36840
gagttgaggc tgcgaagagc actcaaagag caatcgatgc ggtatctgct aagtatcaag   36900
aagaccttgc cgcgctggaa gggagcactg ataggattat ttctgatttg cgtagcgaca   36960
ataagcggtt gcgcgtcaga gtcaaaacta ccggaaccct cgatggtcag tgtggattcg   37020
agcctgatgg tcgagccgaa cttgacgacc gagatgctaa acgtattctc gcagtgaccc   37080
agaagggtga cgcatggatt cgtgcgttac aggatactat tcgtgaactg caacgtaagt   37140
aggaaatcaa gtaaggaggc aatgtgtcta ctcaatccaa tcgtaatgcg ctcgtagtgg   37200
```

```
cgcaactgaa aggagacttc gtggcgttcc tattcgtctt atggaaggcg ctaaacctac    37260
cggtgcccac taagtgtcag attgacatgg ctaaggtgct ggcgaatgga gacaacaaga    37320
agttcatctt acaggctttc cgtggtatcg gtaagtcgtt catcacatgt gcgttcgttg    37380
tgtggtcctt atggagagac cctcagttga agatacttat cgtatcagcc tctaaggagc    37440
gtgcagacgc taactccatc tttattaaga acatcattga cctgctgcca ttcctatctg    37500
agttaaagcc aagacccgga cagcgtgact cggtaatcag ctttgatgta ggcccagcca    37560
atcctgacca ctctcctagt gtgaaatcag taggtatcac tggtcagtta actggtagcc    37620
gtgctgacat tatcattgcg gatgacgttg agattccgtc taacagcgca actatgggtg    37680
cccgtgagaa gctatggact ctggttcagg agttcgctgc gttacttaaa ccgctgcctt    37740
cctctcgcgt tatctacctt ggtacacctc agacagagat gactctctat aaggaacttg    37800
aggataaccg tgggtacaca accattatct ggcctgctct gtacccaagg acacgtgaag    37860
agaacctcta ttactcacag cgtcttgctc ctatgttacg cgctgagtac gatgagaacc    37920
ctgaggcact tgctgggact ccaacagacc cagtgcgctt tgaccgtgat gacctgcgcg    37980
agcgtgagtt ggaatacggt aaggctggct ttacgctaca gttcatgctt aaccctaacc    38040
ttagtgatgc cgagaagtac ccgctgaggc ttcgtgacgc tatcgtagcg gccttagact    38100
tagagaaggc cccaatgcat taccagtggc ttccgaaccg tcagaacatc attgaggacc    38160
ttcctaacgt tggccttaag ggtgatgacc tgcatacgta ccacgattgt tccaacaact    38220
caggtcagta ccaacagaag attctggtca ttgaccctag tggtcgcggt aaggacgaaa    38280
caggttacgc tgtgctgtac acactgaacg gttacatcta ccttatggaa gctggaggtt    38340
tccgtgatgg ctactccgat aagacccttg agttactcgc taagaaggca aagcaatggg    38400
gagtccagac ggttgtctac gagagtaact tcggtgacgg tatgttcggt aaggtattca    38460
gtcctatcct tcttaaacac cacaactgtg cgatggaaga gattcgtgcc cgtggtatga    38520
aagagatgcg tatttgcgat acccttgagc cagtcatgca gactcaccgc cttgtaattc    38580
gtgatgaggt cattagggcc gactaccagt ccgctcgtga cgtagacggt aagcatgacg    38640
ttaagtactc gttgttctac cagatgaccc gtatcactcg tgagaaaggc gctctggctc    38700
atgatgaccg attggatgcc cttgcgttag gcattgagta tctccgtgag tccatgcagt    38760
tggattccgt taaggtcgag ggtgaagtac ttgctgactt ccttgaggaa cacatgatgc    38820
gtcctacggt tgctgctacg catatcattg agatgtctgt gggaggagtt gatgtgtact    38880
ctgaggacga tgagggttac ggtacgtctt tcattgagtg gtgatttatg ca            38932
```

HOST BACTERIUM SPECIFIC NANOPARTICLE

TECHNICAL FIELD

The present invention relates to the use of a bacteriophage (hereinafter, sometimes abbreviated as "phage" according to convention) which is a virus that infects bacteria. More specifically, the present invention relates to a host bacterium-specific nanoparticle consisting of a recombinant phage and its use. The present application claims priority based on Japanese Patent Application No. 2018-244789 filed on Dec. 27, 2018, the contents of which are incorporated herein by reference in its entirety.

BACKGROUND ART

Drug-resistant bacteria have become widespread worldwide, while the development of novel antibacterial drugs is stagnant. Under such circumstances, "phage therapy" is attracting attention (see, for example, PTL 1 and NPLs 1 and 2 for phage therapy). Phages are natural enemy viruses that infect bacteria. They have a series of life cycle: (1) adhesion to bacteria, (2) injection of phage genomes, (3) proliferation in bacteria, (4) bacteriolysis, (5) release of progeny phages, and (6) re-infection to bacteria. The treatment of bacterial infections with phages is phage therapy. Phages have extremely high host specificity, and thus do not kill bacteria indiscriminately like antibacterial agents, but can kill almost only target bacteria. Therefore, the phages have the merit of being able to treat the bacterial infections without disturbing the originally constructed bacterial flora.

CITATION LIST

Patent Literature

[PTL 1] WO 2016/071503

Non Patent Literature

[NPL 1] Front Microbiol. 2012; 3: 238.
[NPL 2] Curr Opin Investig Drugs. 2009 August; 10(8): 766-74.

SUMMARY OF INVENTION

Technical Problem

Phages are viruses and will continue to proliferate as long as the target bacterium (host) is present. The possibilities that they may acquire mutations in the process of proliferation to acquire unintended side effects such as infectivity to humans, that they may cause transfer of harmful genes of target bacteria (horizontal transfer), and that they may infect good bacteria possessed by humans, etc. cannot be eliminated. Therefore, it is a challenge of the present invention to provide a recombinant phage (host bacterium-specific nanoparticle) having high safety and excellent practicality/usefulness. More specifically, it is a challenge of the present invention is to create a recombinant phage that is deprived of its proliferative capacity and can infect the host bacterium only once. The recombinant phage, which has the characteristic of being able to infect the host bacterium only once, not only can be used in phage therapy but also is useful as a genetic engineering tool for genetic modification/genome editing of the target bacterium.

Solution to Problem

Two types of strategies were devised to solve the above problems. As a first strategy, a phage was modified so as to be complete in phenotype and incomplete in genotype. Specifically, a phage genome lacking a part of a virion constituent gene (a gene for a protein constituting a phage particle) (virion constituent gene-deleted phage genome) was introduced into the host bacterium carrying a plasmid encoding the deleted gene. It was expected that a recombinant phage complete in phenotype but incomplete in genotype (a part of the virion constituent genes were deleted), in which proteins other than the virion constituent protein encoded by the deleted gene were expressed from the deleted phage genome, and the virion constituent protein encoded by the deleted gene was expressed from the plasmid, would be formed in the host bacterium after the introduction operation. When a tail gene was adopted as an example of the gene to be deleted to perform a verification experiment, the generated recombinant phage had its original function (lytic activity against the target bacterium), but could not re-infect the target bacterium. On the other hand, as a second strategy, a phage genome lacking a packaging site (PAC site) necessary for phage packaging, i.e., storage of the phage genome in the head (PAC site-deleted phage genome) was introduced into the host bacterium having the PAC site on a plasmid. It was expected that a recombinant phage available as a plasmid carrier (that is, a gene introduction tool), in which various proteins required for phage formation were expressed from the PAC site-deleted phage genome, and a plasmid having the PAC site was packaged, would be obtained in the host bacterium after the introduction operation. As a result of verifying the effectiveness of the strategies, the formation of recombinant phages showing the expected properties was confirmed. In this way, the effectiveness of the two types of strategies was confirmed. It should be noted that 100% biological containment was successfully attained in both of the strategies.

The following invention is based on the above results.

[1] A method for preparing a host bacterium-specific nanoparticle, including the following steps (1) and (2):
  (1) a step of providing a recombinant vector ligated with a bacteriophage genome in which a part of a virion constituent gene is deleted; and
  (2) a step of causing a packaging reaction in the coexistence of the recombinant vector and a plasmid encoding the deleted virion constituent gene.

[2] The preparation method according to [1], wherein the bacteriophage genome is provided as a plurality of fragments, and the recombinant vector is prepared by a seamless cloning method using the plurality of fragments and a linear vector.

[3] The preparation method according to [2], wherein the seamless cloning method is gap-repair cloning or Gibson Assembly utilizing homologous recombination in yeast cells.

[4] The preparation method according to any one of [1] to [3], wherein the deleted virion constituent gene is a head gene or a tail gene.

[5] The preparation method according to any one of [1] to [3], wherein the deleted virion constituent gene is a tail gene.

[6] The preparation method according to any one of [1] to [5], wherein the bacteriophage genome is a genome of T7 phage.

[7] The preparation method according to any one of [1] to [6], wherein step (2) consists of the following steps (2-1) and (2-2):
(2-1) a step of introducing the recombinant vector into a host bacterium carrying a plasmid that encodes the deleted virion constituent gene; and
(2-2) a step of culturing the host bacterium after the introduction operation.

[8] The method according to any one of [1] to [7], further including the following step (3):
(3) a step of recovering a bacteriophage generated by the packaging reaction.

[9] A host bacterium-specific nanoparticle, consisting of a recombinant bacteriophage that includes a head and a tail, and has an ability to infect but no ability to re-infect a host bacterium,
the head having stored therein a bacteriophage genome in which a part of a virion constituent gene is deleted.

[10] The host bacterium-specific nanoparticle according to [9], wherein the deleted virion constituent gene is a head gene or a tail gene.

[11] The host bacterium-specific nanoparticle according to [9], wherein the deleted virion constituent gene is a tail gene.

[12] The host bacterium-specific nanoparticle according to any one of [9] to [11], wherein the bacteriophage genome is a genome of T7 phage.

[13] An antibacterial agent containing the host bacterium-specific nanoparticle according to any one of [9] to [12] as an active ingredient.

[14] A composition containing the antibacterial agent according to [13].

[15] The composition according to [14], which is a pharmaceutical, disinfectant, cleaning agent or oral composition against bacterial infections.

[16] A method for preparing a host bacterium-specific nanoparticle, including the following steps (1) and (2):
(1) a step of providing a recombinant vector ligated with a bacteriophage genome in which a packaging site is deleted; and
(2) a step of causing a packaging reaction in the coexistence of the recombinant vector and a plasmid having the deleted packaging site and encoding a target gene.

[17] The preparation method according to [16], wherein the bacteriophage genome is provided as a plurality of fragments, and the recombinant vector is prepared by a seamless cloning method using the plurality of fragments and a linear vector.

[18] The preparation method according to [17], wherein the seamless cloning method is gap-repair cloning utilizing homologous recombination in yeast cells.

[19] The preparation method according to any one of [16] to [18], wherein the bacteriophage genome is a genome of T7 phage.

[20] The preparation method according to any one of [16] to [19], wherein the target gene is one or more genes selected from the group consisting of a marker gene, a reporter gene, an enzyme gene, a gene for genome editing, a gene encoding an antibacterial peptide, an antibacterial gene, and a group of genes constituting a synthetic gene circuit.

[21] The method according to any one of [16] to [20], wherein step (2) consists of the following steps (2-1) and (2-2):

(2-1) a step of introducing the recombinant vector into a host bacterium carrying a plasmid that has the deleted packaging site and encodes the target gene; and
(2-2) a step of culturing the host bacterium after the introduction operation and then lysing the host bacterium.

[22] The method according to any one of [16] to [21], further including the following step (3):
(3) a step of recovering a bacteriophage generated by the packaging reaction.

[23] A host bacterium-specific nanoparticle, consisting of a recombinant bacteriophage that includes a head and a tail, and has an ability to infect but no ability to re-infect a host bacterium,
the head having stored therein a plasmid having a packaging site and encoding the target gene.

[24] The host bacterium-specific nanoparticle according to [23], wherein the bacteriophage genome is a genome of T7 phage.

[25] The host bacterium-specific nanoparticle according to [23] or [24], wherein the target gene is one or more genes selected from the group consisting of a marker gene, a reporter gene, an enzyme gene, a gene for genome editing, a gene encoding an antibacterial peptide, an antibacterial gene, and a group of genes constituting a synthetic gene circuit.

[26] A composition for transduction, containing the host bacterium-specific nanoparticle according to any one of [23] to [25] as an active ingredient.

DESCRIPTION OF EMBODIMENTS

Figure 1:
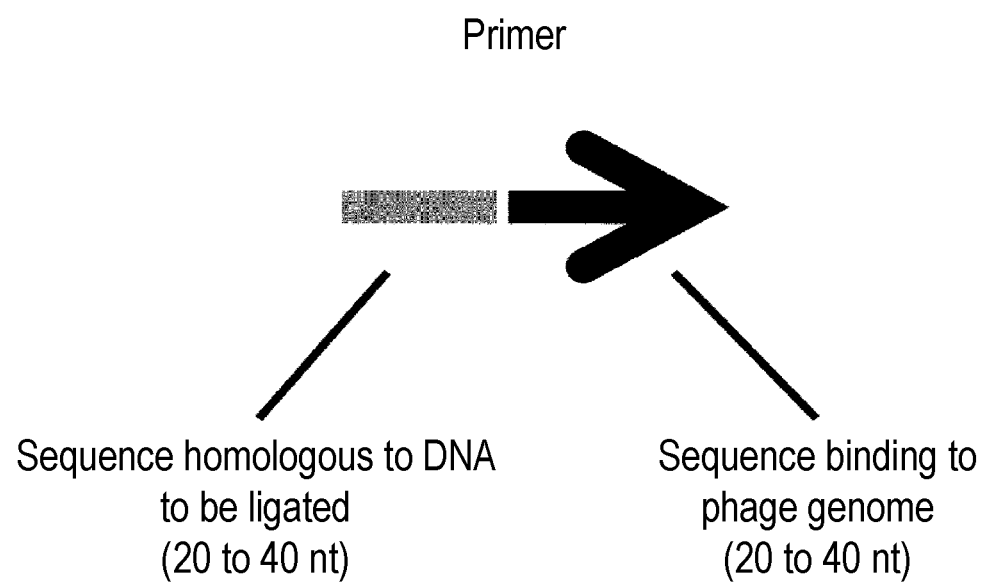
FIG. 1 Primer for preparing a DNA fragment for reconstruction of a designer phage genome.

1. Host Bacterium-Specific Nanoparticle Consisting of Virion Constituent Gene-Deleted Recombinant Phage A first aspect of the present invention is directed to a recombinant phage in which a part of a virion constituent gene is deleted. Since the recombinant phage of this aspect can be used as an active ingredient of an antibacterial agent (details will be described later) and has a nano-order size, it is sometimes referred to as "antibacterial nanoparticle of the present invention", for convenience of explanation.

The structure of the phage is roughly divided into a head and a tail. A phage genome is stored in the head. The tail is important for infection to the host bacterium, and is composed of tail (part) fibers, a base plate, a spike, and the like while the construction thereof differs depending on the type of phage. The phage genome constituting the antibacterial nanoparticle of the present invention lacks a part of the virion constituent genes. That is, an incomplete phage genome in which a part of the virion constituent genes are deleted is stored in the head. Due to this structural feature, it has an ability to infect but no ability to re-infect the host bacterium. Thus, the antibacterial nanoparticle of the present invention exhibits a phenotype required for infection to the host bacterium, but is incomplete in genotype and can infect the host bacterium only once.

The phage exhibits host bacterial specificity. In the present invention, the host bacterium is not particularly limited, and the shape (in general, roughly classified into spherical, rod-shaped and spiral), Gram-stainability (Gram-positive or Gram-negative), oxygen requirement (aerobic, anaerobic, or facultative anaerobic), pathogenicity, mode of existence, and the like do not matter. Examples of the host bacterium include *Escherichia coli*, bacteria of the genus *Shigella* (*S. dysenteriae*, *S. frexneri*, *S. sonnei*, etc.), bacteria of the genus *Salmonella* (*S. typh*, *S. paratyphi*-A, *S. schottmuelleri*, *S. typhimurium*, *S. enteritidis*, etc.), bacteria of the genus *Enterobacter* (*E. aerogenes*, *E. cloacae*, etc.), bacteria of the genus *Klebsiella* (*K. pneumoniae*, *K. oxytoca*, etc.), bacteria of the genus *Proteus* (*P. mirabilis*, *P. vulgaris*, etc.), bacteria of the genus *Yersinia* (*Y. pestis*, *Y. enterocolitica*, etc.), bacteria of the genus *Vibrio* (*V. cholerae*, *V. parahaemolyticus*, etc.), bacteria of the genus *Haemophilus* (*H. influenzae*, *H. parainfluenzae*, *H. ducreyi*, etc.), bacteria of the genus *Pseudomonas* (*P. aeruginosa*, *P. cepacia*, *P. putida*, etc.), bacteria of the genus *Acinetobacter* (*A. calcoaceticus*, *A. baumannii*, *A. lwoffii*, etc.), bacteria of the genus *Legionella* (*L. pneumophila*, etc.), bacteria of the genus *Bordetella* (*B. pertussis*, *B. parapertussis*, *B. bronchiseptica*, etc.), bacteria of the genus *Brucella* (*B. melitensis*, *B. abortus*, *B. suis*, etc.), *Francisella tularensis*, bacteria of the genus *Bacteroides* (*B. fragilis*, *B. melaninogenicus*, etc.), bacteria of the genus *Neisseria* (*N. gonorrhoeae*, *N. meningitidis*, etc.), bacteria of the genus *Staphylococcus* (*S. aureus*, *S. epidermidis*, *S. saprophyticus*, etc.), bacteria of the genus *Streptococcus* (*S. pyogenes*, *S. agalactiae*, *S. viridans*, *S. pneumoniae*, etc.), bacteria of the genus *Enterococcus* (*E. faecalis*, *E. faecium*, *E. avium*, etc.), bacteria of the genus *Bacillus* (*B. subtilis*, *B. anthracis*, *B. cereus*, etc.), bacteria of the genus *Clostridium* (*C. difficile*, *C. botulinum*, *C. perfringens*, *C. tetani*, etc.), bacteria of the genus *Corynebacterium* (*C. diphtheriae*, etc.), bacteria of the genus *Mycobacterium* (*M. tuberculosis*, *M. bovis*, *M. leprae*, *M. avium*, *M. intracellulare*, *M. kansasii*, *M. ulcerans*, etc.), *Mycoplasma*, bacteria of the genus *Borrelia* (*B. recurrentis*, *B. burgdoferi*, etc.), *Treponema palidum*, bacteria of the genus *Campylobacter* (*C. coli*, *C. jejuni*, *C. fetus*, etc.), bacteria of the genus *Helicobacter* (*Helicobacter*) (*H. pylori*, *H. heilmannii*, etc.), bacteria of the genus *Rickettsia* (*R. prowazekil*, *R. mooseri*, *R. tsutsugamushi*, etc.), bacteria of the genus

*Chlamydia* (*C. trachomatis, C. psittaci*, etc.), and bacteria of the genus *Listeria* (*L. monocytogenes*, etc.).

Hereinafter, the method for preparing the antibacterial nanoparticle of the present invention will be described.

<Method for Preparing Antibacterial Nanoparticle>

The preparation method of the present invention includes the following steps (1) and (2):

(1) a step of providing a recombinant vector ligated with a bacteriophage genome in which a part of a virion constituent gene is deleted; and (2) a step of causing a packaging reaction in the coexistence of the recombinant vector and a plasmid encoding the deleted virion constituent gene.

In the preparation method of the present invention, first, a recombinant vector ligated with a bacteriophage genome in which a part of a virion constituent gene is deleted is provided (step (1)). The bacteriophage genome in which a part of a virion constituent gene is deleted, that is, incomplete bacteriophage genome that does not have a complete set of virion constituent genes is referred to as "virion constituent gene-deleted phage genome" herein.

As long as the deletion gives crucial impairment to the structure required for infection to the host bacterium and the re-infection ability of the phage is lost, the virion constituent gene to be deleted (hereinafter, referred to as "deleted virion gene") is not particularly limited. Therefore, the head gene (gene encoding a part or all of the head) or the tail gene (gene encoding a part or all of the tail) may be deleted. The virion constituent gene-deleted phage genome is prepared by a genetic engineering technique. Therefore, in the virion constituent gene-deleted phage genome, a part of the virion constituent genes are deleted as a result of artificial manipulation. As specific examples of the deleted virion gene, the sequence of a gene (gene 10AB) encoding the head of T7 phage (formed of gene 10A in the genome sequence registered as "DEFINITION: Genome of bacteriophage T7. ACCESSION: V01146 J02518 X00411. VERSION: V01146.1" in NCBI GenBank and gene 10B formed by frame shifting during translation of gene 10A) is shown in SEQ ID NO: 1; the sequence of tail gene, gene 11, is shown in SEQ ID NO: 2 (positions 24228 to 24818 of the genome sequence registered as "DEFINITION: Genome of bacteriophage T7. ACCESSION: V01146 J02518 X00411. VERSION: V01146.1" in NCBI GenBank); the sequence of tail gene, gene 12, is shown in SEQ ID NO: 3 (positions 24842 to 27226 thereof); and the sequence of tail fiber gene, gene 17, is shown in SEQ ID NO: 4 (positions 34624 to 36285 thereof), respectively.

The phage from which the virion constituent gene-deleted phage genome is derived is not particularly limited, and may be either a virulent phage or a temperate phage. The virulent phage proliferates in the host bacterium after infection and eventually lyses and kills the host bacterium (lytic cycle). The temperate phage proliferates through the lytic or lysogenic cycle. In the lysogenic cycle, the phage is incorporated into the genomic DNA of the host bacterium. The phage in this state is referred to as prophage, and the host bacterium carrying the prophage is referred to as lysogen.

Examples of the phage include Myoviridae phages (T4-like virus, P1-like virus, P2-like virus, Mu-like virus, SPO1-like virus, and phiH-like virus), Siphoviridae phages (λ-like virus, γ-like virus, T1-like virus, T5-like virus, c2-like virus, L5-like virus, PsiM1-like virus, phiC31-like virus, and N15-like virus), Podoviridae phages (T7-like virus, phi29-like virus, P22-like virus, and N4-like virus), Tectiviridae phages (Tectivirus), Corticoviridae phages (Corticovirus), Lipothrixviridae phages (Alphalipothrixvirus, Betalipothrixvirus, Gammalipothrixvirus, and Deltalipothrixvirus), Plasmaviridae phages (Plasmavirus), Rudiviridae phages (Rudivirus), Fuselloviridae phages (Fusellovirus), Inoviridae phages (Inoviridae) (Inovirus, Plectrovirus, M13-like virus, and fd-like virus), Microviridae phages (Microvirus, Spiromicrovirus, Bdellomicrovirus, and Chlamydiamicrovirus), Leviviridae phages (Levivirus and Allolevivirus), Cystoviridae phages (Cystovirus), Ampullaviridae phages, Bicaudaviridae phages, Clavaviridae phages, Globuloviridae phages, and Guttavirus phages. The antibacterial nanoparticle of the present invention typically has the function of killing the host bacterium by bacteriolysis. Virulent phages (e.g., T-based phage, SP6 phage, and gh-1 phage) are preferred for this function. Information on the genomic DNA of T7 phage, which is one of particularly preferable phages, is registered in a public database (for example, NCBI GenBank, DEFINITION: Genome of bacteriophage T7. ACCESSION: V01146 J02518 X00411. VERSION: V01146.1), and can be used for the design and preparation of the virion constituent gene-deleted phage genome in the present invention. The same applies to the design and preparation of virion constituent gene-deleted phage genomes corresponding to phages other than the T7 phage, and known sequence information may be used.

A seamless cloning method can be used to prepare the virion constituent gene-deleted phage genome. In the seamless cloning method, a target DNA sequence is provided as a plurality of fragments, and the plurality of fragments are simultaneously cloned into a linearly prepared vector. Seamless cloning methods such as gap-repair cloning (Gap-repairing) (see, e.g., Ando et al., Cell Systems: 1 (3), 2015), Gibson Assembly (e.g., systems and kits (Gibson Assembly Cloning Kit) provided by New England Biolab Japan Ltd. can be used), and In-Fusion cloning (for example, systems and kits (In-Fusion (registered trademark) HD Cloning Kit) provided by Takara Bio Co., Ltd. can be used) have been developed. In a preferred embodiment, gap-repair cloning is employed to reconstruct the virion constituent gene-deleted phage genome in yeast cells. In this case, the virion constituent gene-deleted phage genome is divided into, for example, 2 to 20 (preferably 2 to 8) fragments, each of which is amplified by a nucleic acid amplification reaction represented by the PCR (Polymerase chain reaction) method. On the other hand, a vector having a yeast replication origin is formed in a linear shape and introduced into yeast cells together with an amplified DNA fragment. The vector can be formed in a linear shape by a conventional method such as restriction enzyme treatment. To confirm the success or failure of cloning in yeast, vectors are usually loaded with a selective marker gene such as an auxotrophic marker (e.g., URA3 gene or LEU2 gene) or a drug resistance marker (e.g., ampicillin resistant gene, kanamycin resistant gene, or chloramphenicol resistant gene). Details of the method for preparing the virion constituent gene-deleted phage genome by gap-repair cloning will be described in the Examples below. Gap-repair cloning is used to prepare (reconstruct) a modified phage genome (designer phage genome) (see, for example, U.S. Pat. No. 9,617,522).

In step (2) following step (1), the packaging reaction is carried out in the coexistence of the recombinant vector provided in step (1), that is, the recombinant vector ligated with the reconstituted virion constituent gene-deleted phage genome (hereinafter, referred to as "deleted phage genome vector") and a plasmid encoding the deleted virion constituent gene (that is, the deleted virion gene). Various host bacteria such as *E. coli, Pseudomonas aeruginosa*, and *Staphylococcus aureus* can be used in the packaging reaction. The host bacterium does not have to be the original host (the host of the phage from which the virion constituent gene-deleted phage genome is derived) as long as the phage formed by packaging can lyse the host bacteria. In the case of in vitro packaging using the host bacterium, usually, a host bacterium carrying a plasmid encoding the deleted virion gene is provided in advance, and the deleted phage genome vector is introduced into the host bacterium. In addition to the replication origin of the host bacterium, the plasmid encoding the deleted virion gene is usually loaded with a selective marker gene (e.g., an auxotrophic marker or a drug resistance marker) to confirm its presence. When the deleted virion gene does not contain a promoter, the promoter may be introduced when constructing the plasmid, or a plasmid vector having the promoter may be used. In the former case, for example, a promoter sequence is provided on the primer used to amplify the deleted virion gene by PCR so that an amplification product in which the primer is arranged immediately upstream of the gene can be obtained. For the construction of the plasmid encoding the deleted virion gene, for example, cloning using Gibson Assembly, a restriction enzyme and a ligase can be used. In addition, the plasmid may be introduced into the host bacterium by a conventional method such as a competent cell method or an electroporation method. On the other hand, the method for introducing the deleted phage genome vector into the host bacterium is also not particularly limited, and for example, electroporation can be used.

As described above, when the deleted phage genome vector is introduced into the host bacterium carrying the plasmid encoding the deleted virion gene, all but the virion constituent proteins encoded by the deleted virion gene are expressed from the deleted phage genome vector, and the virion protein encoded by the deleted virion gene is expressed from the plasmid, respectively, in the host bacterium, and a recombinant phage, which is complete in phenotype but incomplete in genotype (a part of the virion constituent genes are deleted), is formed. When the host bacterium is cultured under appropriate conditions, it is finally lysed, and the recombinant phage is released. The released recombinant phage can be recovered by a conventional method. Either a solid medium or a liquid medium may be used for culturing the host bacterium, but from the viewpoint of recovery efficiency of recombinant phage and convenience of recovery operation, it is preferable to use a liquid medium, that is, to adopt liquid culture. In the case of liquid culture, for example, culture is carried out until the bacterium is completely lysed, and then the culture solution is subjected to treatment such as purification and sterilization as necessary to obtain a recombinant phage solution. Preferably, the remaining host bacterium is killed by chloroform treatment or the like before the operation of recovering the culture solution.

<Use of Antibacterial Nanoparticle>

Due to its characteristic structure, the antibacterial nanoparticle of the present invention shows the property of having an ability to infect but no ability to re-infect the host bacterium, and exhibits a host bacterium-specific bactericidal ability. Therefore, it is useful as an active ingredient of a bactericidal agent having high safety and excellent specificity. The "antibacterial agent" refers to an agent having an action/effect of suppressing the growth of bacteria (bacteriostatic) or an action/effect of killing bacteria (bactericidal). The antibacterial agent of the present invention is used for various purposes as a composition containing the same. Hereinafter, as typical uses, pharmaceuticals (therapeutic agents or preventive agents), disinfectants, cleaning agents and oral compositions using the composition of the present invention will be described.

(i) Pharmaceutical

The pharmaceutical of the present invention is used for the treatment or prevention of bacterial infections. The pharmaceutical of the present invention may exert a therapeutic effect or a preventive effect (these two effects are collectively referred to as "pharmaceutical effect") against bacterial infections). The pharmaceutical effects here include (1) prevention of bacterial infections, (2) prevention, suppression or delay of the onset of bacterial infections, and (3) alleviation (mitigation) of symptoms characteristic of, or associated with, bacterial infections), and (4) prevention, suppression or delay of exacerbation of symptoms characteristic of, or associated with, bacterial infections. Since the therapeutic effect and the preventive effect are partially overlapping concepts, it may be difficult to clearly distinguish them, and the practical benefit of doing so is small.

Pharmaceutical formulation can be performed according to a conventional method. Preferably, a pharmaceutically acceptable medium is combined for formulation. A "pharmaceutically acceptable medium" refers to a substance that provides an advantage or benefit regarding the administration, storage, etc. of the pharmaceutical of the present invention without substantially affecting the efficacy (target bacterium-specific sterilization) of the active ingredient of the present invention. Examples of the "pharmaceutically acceptable medium" include deionized water, ultrapure water, physiological saline, phosphate buffered saline (PBS), and 5% dextrose aqueous solution. In addition, at the time of formulation, other components permitted in the formulation (for example, carriers, excipients, disintegrants, buffers, emulsifiers, suspension agents, soothing agents, stabilizers, preservatives, preservatives, physiological saline, etc.) can be incorporated. As the excipient, lactose, starch, sorbitol, D-mannitol, white sugar and the like can be used. As the disintegrant, starch, carboxymethyl cellulose, calcium carbonate and the like can be used. As the buffer, phosphate, citrate, acetate or the like can be used. As the emulsifier, gum arabic, sodium alginate, tragacanth and the like can be used. As the suspension agents glyceryl monostearate, aluminum monostearate, methyl cellulose, carboxymethyl cellulose, hydroxymethyl cellulose, sodium lauryl sulfate and the like can be used. As the soothing agent, benzyl alcohol, chlorobutanol, sorbitol and the like can be used. As the stabilizer, propylene glycol, ascorbic acid and the like can be used. As the preservative, phenol, benzalkonium chloride, benzyl alcohol, chlorobutanol, methylparaben and the like can be used. As the preservative, benzalkonium chloride, paraoxybenzoic acid, chlorobutanol and the like can be used.

The dosage form for formulation is also not particularly limited. Examples of dosage forms are tablets, powders, fine granules, granules, capsules, syrups, injections, external preparations (ointments, creams, lotions, liquids, gels, paps, plasters, tapes, aerosols, etc.), and suppositories. The pharmaceutical is orally or parenterally administered depending on its dosage form (local injection into the affected area, intravenous, intraarterial, subcutaneous, intradermal, intramuscular, or intraperitoneal injection, transdermal, nasal, transmucosal, etc.) to be applied to the subject. Systemic and topical administrations are also adapted depending on the subject. These routes of administration are not mutually exclusive, and two or more arbitrarily selected routes can be used in combination.

The pharmaceutical of the present invention contains an amount of the active ingredient necessary for obtaining the expected effect (that is, a therapeutically or prophylactically effective amount). The amount of the active ingredient in the pharmaceutical of the present invention generally varies depending on the dosage form, but the amount of the active ingredient is set in the range of, for example, about 0.001% by weight to about 80% by weight so that a desired dose can be achieved.

The dosage of the pharmaceutical of the present invention is set so as to obtain the expected effect. Symptoms, patient age, gender, weight, etc. are generally taken into account when setting the therapeutically or prophylactically effective dose. Those skilled in the art can set an appropriate dose in consideration of these matters. As an example of the dose, the dose can be set so that the amount of active ingredient (amount of antibacterial nanoparticle of the present invention) per day for an adult (body weight about: 60 kg) is $10^3$ pfu/mL to $10^{11}$ pfu/mL, preferably $10^7$ pfu/mL to $10^{11}$ pfu/mL. As the administration schedule, for example, once to several times a day, once every two days, or once every three days can be adopted. In preparation of the administration schedule, the patient's condition and the duration of the effect of the active ingredient can be taken into consideration.

In parallel with the treatment or prevention by the pharmaceutical of the present invention, treatment with other medicines, typically antibacterial agents (e.g., penicillin antibacterial agents, cephem antibacterial agents, carbapenem antibacterial agents, penem antibacterial agents, tetracycline antibacterial agents, β-lactamase inhibitors, phosphomycin, vancomycin, aminoglycoside antibacterial agents, and macrolide antibacterial agents) may be performed. The mechanism of action of the active ingredient of the present invention is different from that of existing antibacterial agents which are generally used. Therefore, if the pharmaceutical of the present invention is used in combination with an existing antibacterial agent, it is expected that a combined action/effect will be exhibited, and the therapeutic effect can be increased.

As is clear from the above description, the present application provides a method for treating or preventing various bacterial infections (so-called phage therapy), including administering a therapeutically or prophylactically effective amount of a pharmaceutical containing the antibacterial nanoparticle of the present invention to a subject suffering from or likely to suffer from a bacterial infection. The target for treatment or prevention is typically humans, but the treatment or prevention may be applied to non-human mammals (e.g., monkeys, cows, pigs, horses, goats, sheep, dogs, cats, rabbits, etc.) and birds (chickens, quails, turkeys, geese, ducks, ostriches, wild ducks, parakeets, Java sparrows, etc.), fish and shellfish, reptiles (lizards, snakes, iguanas, chameleons, turtles, geckos, etc.), amphibians (frogs, newts, salamanders, etc.), plants, etc.

(ii) Disinfectant, Cleaning Agents

The disinfectant or cleaning agent of the present invention is used, for example, for disinfecting or cleaning living rooms (including hospital rooms), cooking rooms, toilets, washrooms, bathrooms, etc., for disinfecting or cleaning tableware, cutleries (knives, forks, spoons, etc.), cooking utensils (kitchen knives, knives, pots, mixers, microwave ovens, ovens, etc.), for disinfecting or cleaning medical utensils and devices, and for disinfecting or cleaning hands, fingertips, oral cavity, etc. The disinfectant or cleaning agent of the present invention is composed of, for example, a liquid (for example, a spray, a lotion), a gel, or a solid (for example, a powder), and is applied by coating, spraying, spraying, or the like. The disinfectant or bactericidal agent of the present invention may be supported or adhered to a carrier made of natural fibers, synthetic fibers, or the like (for example, in the form of a sheet) to provide a product used for wiping, a mask for preventing infection, or the like.

Antibacterial or disinfectant component such as benzalkonium chloride, cetylpyridinium chloride, phenoxyethanol, isopropylmethylphenol, and chlorhexidine gluconate, pH adjusters, surfactants, adsorbents, carriers, etc. may be added to the disinfectant or cleaning agent of the present invention.

(iii) Oral Composition

The oral composition of the present invention can be used for maintaining the hygienic state of the oral cavity, improving the oral environment, and the like. In particular, it can be expected to be applied to the prevention or treatment of periodontal diseases or related diseases. The oral composition of the present invention can expected to provide a bactericidal effect specific to the target bacterium. Typical target bacteria are those that cause periodontal diseases, such as *Aggregatibacter actinomycetemcomitans, Porphyromonas gingivalis, Prevotella intermedia*, and *Treponema denticola*. The oral composition of the present invention can also be used as a dental bactericidal agent, and is expected to be used as a bactericidal agent after implant, or added to a mouthwash (mouthwash) or a toothpaste.

The oral composition of the present invention is provided in the form of, for example, a dentifrice, a liquid dentifrice, a dental gel, a gargle, a mouthwash, a candy, a troche or a chewing gum. In addition to the active ingredient (antibacterial nanoparticle) characteristic of the present invention, the oral composition of the present invention may contain a commonly used oral base, additives and the like. Examples of oral bases are dental calcium hydrogen phosphate, aluminum oxide, and sorbitol solution. Examples of the additive include a binder, a wetting agent, a foaming agent, a surfactant, a solvent, a solubilizing agent, a preservative, a sweetener, and a coloring agent.

2. Host Bacterium-Specific Nanoparticle for Transduction

A second aspect of the present invention relates to a recombinant phage that can be used for transduction into the host bacterium. For convenience of explanation, the recombinant phage of this aspect may be referred to as "transduction nanoparticle of the present invention". In the transduction nanoparticle of the present invention, a plasmid having a packaging site (sometimes abbreviated as "PAC site") and encoding a target gene is stored in the head. By storing a specific plasmid in the head, instead of the phage genome, it has an ability to infect but no ability to re-infect the host bacterium (can infect the host bacterium only once), and functions as a target bacterium-specific transduction tool. The PAC site retained by the plasmid stored in the head reflects the process of preparing the transduction nanoparticle of the present invention, which is characteristic of the present invention. Hereinafter, the method for preparing the transduction nanoparticle of the present invention will be described, but the description thereof will be omitted for the same matters as in the first aspect, and the above description will be incorporated.

<Method for Preparing Transduction Nanoparticle>

The preparation method of the present invention includes the following steps (1) and (2):

(1) a step of providing a recombinant vector ligated with a bacteriophage genome in which a packaging site is deleted; and (2) a step of causing a packaging reaction in the coexistence of the recombinant vector and a plasmid having the deleted packaging site and encoding the target gene.

In the preparation method of the present invention, first, a recombinant vector ligated with a bacteriophage genome in which a PAC site is deleted is provided (step (1)). The bacteriophage genome in which the PAC site is deleted, i.e., incomplete bacteriophage genome that has no PAC site and itself is not packaged, is referred to as "PAC site-deleted phage genome". The PAC site is a sequence required for packaging of the phage genome during the formation of phage in the host bacterium. Therefore, the PAC site-deleted phage genome is not packaged, resulting in the production of phage having no phage genome (the phage genome is missing).

Typically, a phage genome lacking only the PAC site is used. However, it is also possible to use a phage genome in which any other than the PAC site is deleted intentionally or due to the necessity of recombination operation or the like. In this case, if the additionally deleted portion is a gene required for phage formation (for example, a part of the virion constituent genes), a plasmid packaged due to the presence of the PAC site (see the description of step (2)) may also encode the gene, or another plasmid encoding the gene may be introduced into the host bacterium used for packaging. As an example of the PAC site, the sequence of the PAC site on the 5' end side of T7 phage is shown in SEQ ID NO: 5, and the sequence of the PAC site on the 3' end side thereof is shown in SEQ ID NO: 6.

The PAC site-deleted phage genome can be prepared by the seamless cloning method (preferably gap-repair cloning) as in the first aspect.

In step (2) following step (1), the packaging reaction is carried out in the coexistence of the recombinant vector provided in step (1), i.e., the recombinant vector ligated with the reconstituted PAC site-deleted phage genome (hereinafter, "PAC site-deleted phage genome") and a plasmid having the deleted PAC site and encoding the target gene (hereinafter referred to as "PAC site-carrying plasmid"). As in the first aspect, various host bacteria such as E. coli, Pseudomonas aeruginosa, Staphylococcus aureus and the like can be used in the packaging reaction. The procedures for introducing the PAC site-deleted phage genome vector and the PAC site-carrying plasmid into the host bacterium are the same as in the first aspect.

Typically, a host bacterium carrying a PAC site-carrying plasmid is prepared in advance, a PAC site-deleted phage genome vector is introduced into the host bacterium, and a state requiring a packaging reaction (i.e., condition that the PAC site-deleted phage genome vector and the PAC site-carrying plasmid coexist) is formed. The PAC site-carrying plasmid has a PAC site, and, additionally, encodes the target gene. The target gene is a gene that is introduced into the target bacterium by the transduction nanoparticle of the present invention and that is expressed in the target cell. Although one target gene is typically used, two or more target genes may be encoded by the PAC site-carrying plasmid. Various genes can be adopted as the target gene. Examples of the target gene include marker genes (drug-resistant genes such as neomycin resistant gene (neo), kanamycin resistant gene (npt), hyglomycin resistant gene (hph) and methotrexate resistant gene (dhfr), luminescent protein genes such as β-galactosidase gene (lacZ), β-glucuronidase (GUS) gene and luciferase gene (luc), and fluorescent protein genes such as GFP gene) and, reporter genes (luminescent protein genes such as luciferase gene (luc) and fluorescent protein genes such as GFP gene), (enzyme genes for genome editing such as enzyme gene (ZFN (Zinc Finger Nuclease), TALEN (Transcription Activator-Like Effector Nuclease) and CRISPR-Cas9, genes of sugar-related enzymes such as α-amylase, β-amylase, glucan 1,4-α-glucosidase, pullulanase, and isoamylase, genes of protein-related enzymes such as aminopeptidase, dipeptidyl peptidase, carboxypeptidase, trypsin, chymotrypsin, papain, bromelain, pepsin, and chymosin, lipid-related enzyme genes such as lipase and phospholipase, amino acid-related enzyme genes such as asparaginase and glutaminase, plant tissue-disintegrating enzyme genes such as cellulase, pectinase and hemicellulase, genes of nucleic acid-related enzymes such as endonucleases, exonucleases, DNA polymerases, helicases, DNA topoisomerases, RNA polymerases, and adenylate deaminase, genes of pharmaceutical enzymes such as amylase, lipase, cellulase, and galactosidase, genes for diagnostic enzymes such as glucose oxidase, mutarotase, peroxidase, glucose dehydrogenase, cholesterol esterase, cholesterol oxidase, cholesterol dehydrogenase, lipoprotein lipase, glycerol kinases, L-α-glycerophosphate oxidase, lactase dehydrogenase, uricase, D-3-hydroxybutyrate dehydrogenase, bilirubin oxidase, glutaminase, ascorbic acid oxidase), genes encoding antibacterial peptides (defensin, cathelicidin, dermcidin, drosomycin, etc.), antibacterial gene (lysozyme gene, endolysin, etc.), a group of genes constituting the synthetic gene circuit (riboregulator, recombinase gene, fluorescent protein gene, etc.), genes that bring about the target bacterium-specific killing ability of the bacteriophage (e.g., lytic enzyme genes of T7 phage), genes of substances used in pharmaceuticals and nutritional supplements (cytokines, hormones, neurotransmitters, fibrinogen, serum albumin, lactoferrin, etc.), genes useful for survival and maintenance of target cells, genes encoding proteins that enhance the functions inherent in target cells, and genes encoding proteins that do not act on target cells but are secreted from target cells and act on surrounding cells.

When the marker gene is used as the target gene, the target bacterium of the transduction nanoparticle can be detected using the expression of the gene as an index. Therefore, this aspect is useful for detection, tracking, and the like of the target bacterium, and as a specific application, for example, a test for contamination of food poisoning bacteria in foods can be assumed. Further, a marker gene may be used as a means for confirming that the transduction nanoparticle of the present invention has been introduced into the target bacterium, and in that case, a gene different from the marker gene (one or more genes for transduction into the target cell) is usually used together as the target gene.

If an enzyme gene is adopted as the target gene, a specific enzyme can be forcibly expressed and functioned in the target bacterium. For example, the transduction nanoparticle of the invention can be utilized for enhancing the functionality of bacteria and producing bacteria added with new functions. When a gene for genome editing is used as the target gene, among enzyme genes, the transduction nanoparticle of the present invention can be used for genome modification of the target bacterium. Examples of use forms when an enzyme gene is used as the target gene can include modification of drug sensitivity of drug-resistant bacteria (for example, disruption of drug-resistant gene and conversion thereof to drug-sensitive strain by genome editing), improvement of the productivity of industrial enzyme-producing bacteria, manufacture of foods/beverages (particularly fermented foods and fermented beverages) and pharmaceutical or industrial products (chemical products, etc.), production of bioenergy (e.g., bioethanol), and improvement of bacterial capacity to be used in bioremediation (processing capacity, manufacturing/production capacity, etc.).

The transduction nanoparticle of the present invention can be used as a target bacterium-specific antibacterial agent, by using a gene encoding an antibacterial peptide or a group of genes that bring about the target bacterium-specific killing ability of the bacteriophage as the target gene.

As described above, when the PAC site-deleted phage genome vector is introduced into the host bacterium carrying the PAC site-carrying plasmid, various proteins required for phage formation are expressed from the PAC site-deleted phage genome vector in the host bacterium, and the PAC site-carrying plasmid is packaged. That is, a recombinant phage in which the PAC site-carrying plasmid is stored in the head is formed. Since the formed recombinant phage lacks the phage genome, bacteriolysis usually does not occur. Therefore, the host bacterium is cultured under appropriate conditions to promote the formation of the recombinant phage, and then lysed by chloroform treatment or the like to recover the recombinant phage. The culture conditions, recovery operation, etc. are the same as in the first aspect.

<Use of Transduction Nanoparticle>

As described above, in the transduction nanoparticle of the present invention, the PAC site-carrying plasmid (having the PAC site and encoding the target gene) is stored in the head, instead of the phage genome. Due to this feature, it has an infection ability but no re-infection ability specific to the host bacterium (can infect the host bacterium only once), and functions as a target bacterium-specific transduction tool. Therefore, the present invention also provides a composition for transduction containing transduction nanoparticles as an active ingredient. As described above, since various target genes can be adopted, the composition for transduction of the present invention can be used in a wide range of uses (for example, production of industrial enzymes, manufacture of foods/beverages (particularly fermented foods/fermented beverages) and pharmaceutical and industrial products (chemical products, etc.), production of bioenergy (for example, bioethanol), and bioremediation), and its industrial utility value is extremely high. In addition, as described above, by using a gene encoding an antibacterial peptide or a group of genes that bring about the target bacterium-specific killing ability of the bacteriophage as the target gene, it will function as the target bacterium-specific antibacterial agent. As in the case of the above aspect, it can be used as a medicine (therapeutic agent or a preventive agent), a disinfectant, a cleaning agent, and an oral composition. The transduction nanoparticle of the present invention is also useful as a tool for research (experiment).

EXAMPLES

Focusing on the potential usefulness of the recombinant phage, it was aimed to develop two types of "host bacterium-specific nanoparticles" that can infect the host bacterium only once.

<Material/Operation>

1. Preparation and Confirmation of Virion Constituent Gene-Deleted Phage (Antibacterial Nanoparticle)

1-1. Design and Reconstruction of Designer Phage Genome (Modified Phage Genome)

All designer phage genomes are reconstituted from PCR fragments or artificially synthesized DNA fragments. At that time, 20 to 40 nt of sequences homologous to the ligated fragments are added to the 5' end and 3' end of each fragment. For example, when amplifying the fragment by PCR, a primer is designed as shown in FIG. 1.

Figure 2:
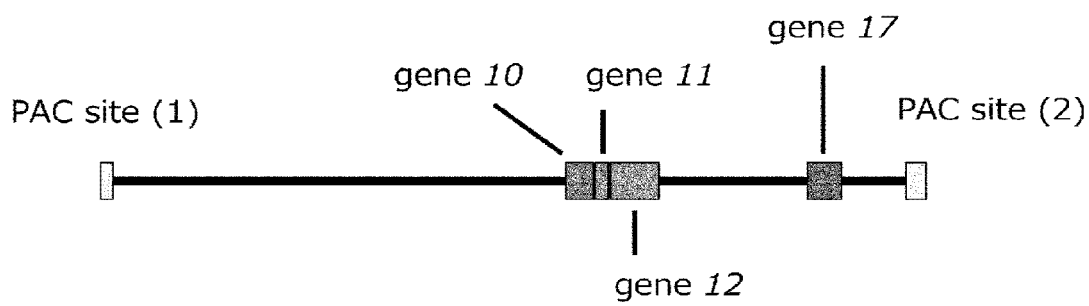
FIG. 2 Design and reconstruction of the designer phage genome (virion constituent gene-deleted phage genome). The phage genome and vector are amplified by PCR using primers designed so that the tail gene is not amplified, and ligated in yeast.
Figure 2:
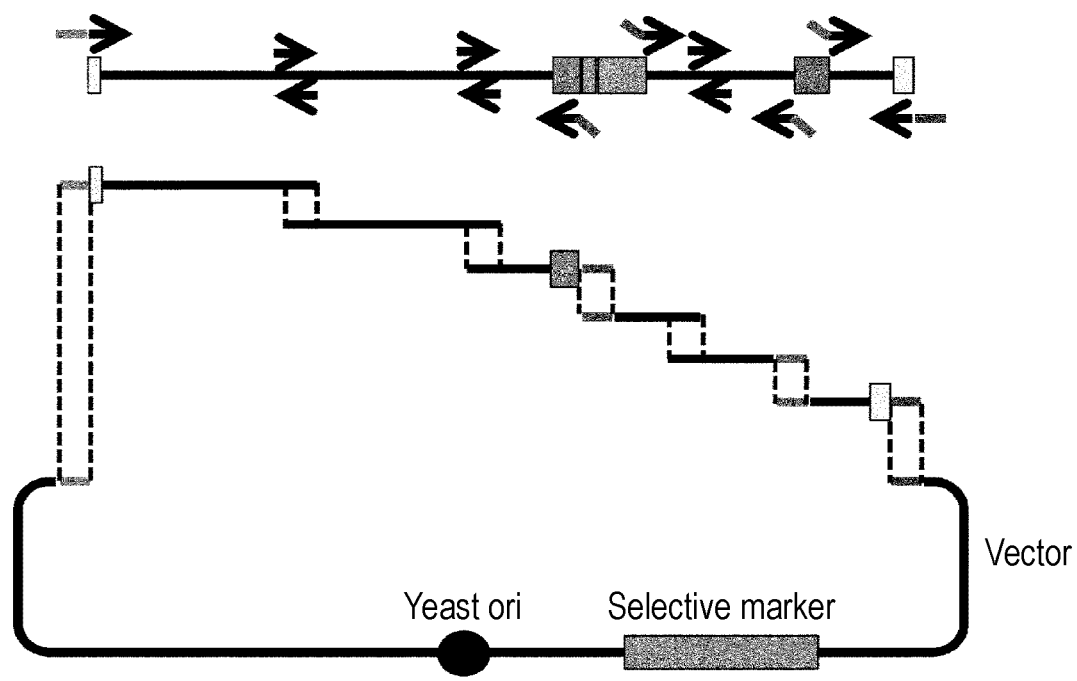

In this study, the tail gene or head gene was deleted among the virion constituent genes. When the tail gene was deleted, the phage genome (tail gene-deleted phage genome) (SEQ ID NO: 7) in which the tail genes, gene 11, gene 12 and gene 17, of the T7 phage were deleted was reconstituted. A primer is designed so that the tail genes (gene 11, gene 12 and gene 17) are not amplified (FIG. 2), and the phage genome and vector pTOW40836 (FIG. 3) are amplified by PCR. The vector is required to carry the phage genome in yeast. A sequence homologous to the vector is provided at the end of the phage genome (FIG. 2). In this study, the phage genome was divided into six parts so as not to contain the tail genes (gene 11, gene 12 and gene 17), and the six fragments (referred to as fragments 1, 2, 3, 4, 5 and 6 in order from the 5' end side to the 3' end side) were amplified by PCR. The sequences of the primers used to amplify the respective fragments are as follows.

(Fragment 1)
Forward primer sequence: CTTGAAGACGAAAGGGCCTCGTGATACGCCTCTCACAGTGTACGGACCTAAAGTTCCC CC (SEQ ID NO: 8)
Reverse primer sequence: ATTACGCGATGACAGTAGACAACCTTTCCG (SEQ ID NO: 9)

(Fragment 2)
Forward primer sequence: TGCAGCAATACCGGAAAGGTTGTCTACTGT (SEQ ID NO: 10)
Reverse primer sequence: ATATGTCTCCTCATAGATGTGCCTATGTGG (SEQ ID NO: 11)

(Fragment 3)
Forward primer sequence: ACTTGTGACTCCACATAGGCACATCTATGA (SEQ ID NO: 12)
Reverse primer sequence: AGGGAGAATATTTAAATAGTTCCTCCTTTCAGCAAAAAACCCCTC (SEQ ID NO: 13)

(Fragment 4)
Forward primer sequence: GAAAGGAGGAACTATTTAAATATTCTCCCTGTGGTGGCTCG (SEQ ID NO: 14)
Reverse primer sequence: GAATAACCTGAGGGTCAATACCCTGCTTGT (SEQ ID NO: 15)

(Fragment 5)
Forward primer sequence: GACATGATGGACAAGCAGGGTATTGACCCT (SEQ ID NO: 16)
Reverse primer sequence: CTTGTGATTTACCAATTGACCTCCTTAAAGTAAATCTAAGAGAC (SEQ ID NO: 17)

(Fragment 6)
Forward primer sequence: CTTTAAGGAGGTCAATTGGTAAATCACAAGGAAAGACGTGTAGTC (SEQ ID NO: 18)
Reverse primer sequence: CATAATAGAAACGACACGAAATTACAAAATAGGGACACAGAGAGACACTCAAGGTAA CAC (SEQ ID NO: 19)

The sequences of the primers used to amplify the vector fragment are as follows.
Forward primer sequence: ATTTTGTAATTCGTGTCGTTTCTATTATG (SEQ ID NO: 20)
Reverse primer sequence: GGCGTATCACGAGGCCCTTTCGTCTTCAAG (SEQ ID NO: 21)

Figure 4:
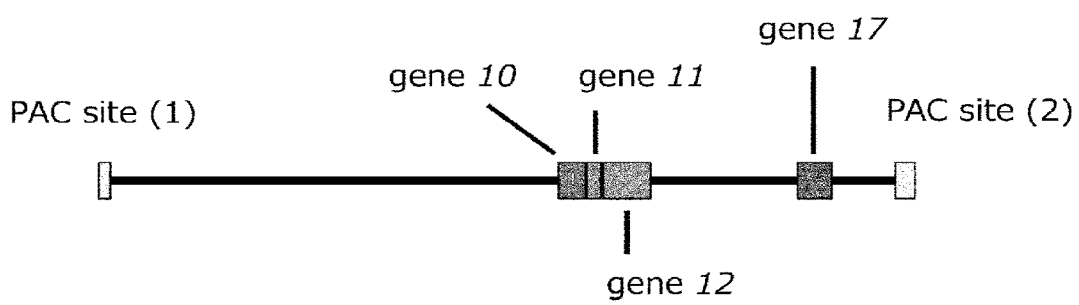
FIG. 4 Design and reconstruction of the designer phage genome (virion constituent gene-deleted phage genome). The phage genome and vector are amplified by PCR using primers designed so that the head gene is not amplified, and ligated in yeast.
Figure 4:
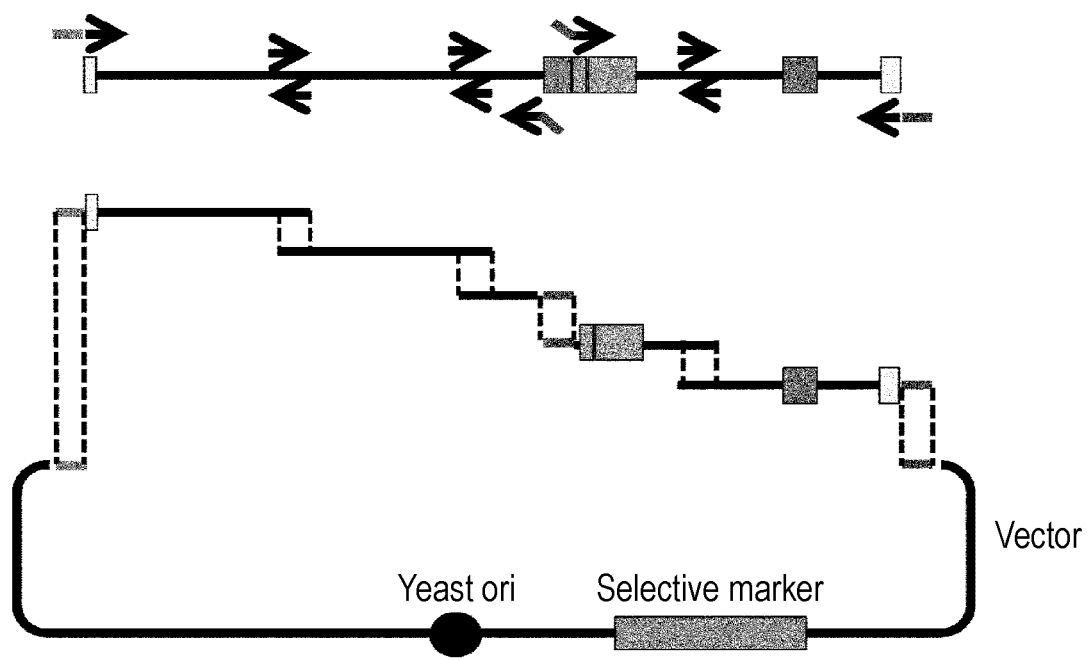

The phage genome lacking the head gene (head gene-deleted phage genome) (SEQ ID NO: 22) was reconstructed in the same manner (FIG. 4). In this case, the phage genome was divided into five parts so as not to contain the head gene (gene 10AB), and the five fragments (referred to as fragments 1', 2', 3', 4' and 5' in order from the 5' end side to the 3' end side) were amplified by PCR. The sequences of the primers used to amplify the respective fragments are as follows.

(Fragment 1')
Forward primer sequence: CTTGAAGACGAAAGGGCCTCGTGATACGCCTCTCACAGTGTACGGACCTAAAGTTCCC CC (SEQ ID NO: 23)
Reverse primer sequence: ATTACGCGATGACAGTAGACAACCTTTCCG (SEQ ID NO: 24)

(Fragment 2')
Forward primer sequence: TGCAGCAATACCGGAAAGGTTGTCTACTGT (SEQ ID NO: 25)
Reverse primer sequence: ATATGTCTCCTCATAGATGTGCCTATGTGG (SEQ ID NO: 26)

(Fragment 3')
Forward primer sequence: ACTTGTGACTCCACATAGGCACATCTATGA (SEQ ID NO: 27)
Reverse primer sequence: GCCCCAAGGGGTTATGCTAGATTTCGAAGTCTATCAGAAGTTCGAATCGATTAC (SEQ ID NO: 28)

(Fragment 4')
Forward primer sequence: CTTCTGATAGACTTCGAAATCTAGCATAACCCCTTGGGGCCTCTAAACGG (SEQ ID NO: 29)
Reverse primer sequence: GAATAACCTGAGGGTCAATACCCTGCTTGT (SEQ ID NO: 30)

(Fragment 5')
Forward primer sequence: GACATGATGGACAAGCAGGGTATTGACCCT (SEQ ID NO: 31)
Reverse primer sequence: CATAATAGAAACGACACGAAATTACAAAATAGGGACACAGAGAGACACTCAAGGTAA CAC (SEQ ID NO: 32)

The same primer set (SEQ ID NOs: 20 and 21) as for the tail genes was used to amplify the vector fragment.

1-2. Preparation of Yeast Competent Cells
(1) Culture yeast in 5 mL of YPD medium at 30° C. overnight.
(2) Add the entire amount of the yeast overnight culture solution to 45 mL of the YPD medium and culture it at 30° C. for 3 hours.
(3) Centrifuge the suspension at 8000 g and room temperature for 15 minutes.
(4) Discard the culture supernatant and suspend the culture in 25 mL of ultrapure water.
(5) Centrifuge the suspension at 8000 g and room temperature for 15 minutes.
(6) Discard the supernatant and suspend the culture in 1 mL of 100 mM LiAc.
(7) Centrifuge the suspension at 12000 g and room temperature for 1 minute.
(8) Discard the supernatant and suspend the culture in 400 µL of 100 mM LiAc. This is used as competent cells.

1-3. Yeast Transformation
(1) Centrifuge 50 µL of the competent cells at 12000 g and room temperature for 1 minute.
(2) Discard the supernatant and add the following reagents in order.
240 µL of PEG3350 (50% w/v)
36 µL of 1M LiAc
25 µL of ssDNA (placed at 100° C. for 5 minutes and on ice for 3 minutes or more)
50 µL of DNA sample (all fragments needed to constitute the designer genome. In the case of tail gene deletion, a combination of the fragments 1 to 6 and the vector DNA. In the case of head gene deletion, a combination of the fragment 1' to 5' and the vector DNA.)
(3) Gently mix the mixed solution by pipetting and let stand at 30° C. for 30 minutes.
(4) Let stand at 42° C. for 20 minutes.
(5) Centrifuge the solution at 12000 g and room temperature for 1 minute.
(6) Discard the supernatant and suspend the culture in 200 µL of an LB liquid medium.
(7) Apply to a selective agar medium.
(8) Let stand at 30° C. (colony can be visually recognized in about 3 days).

Figure 5:
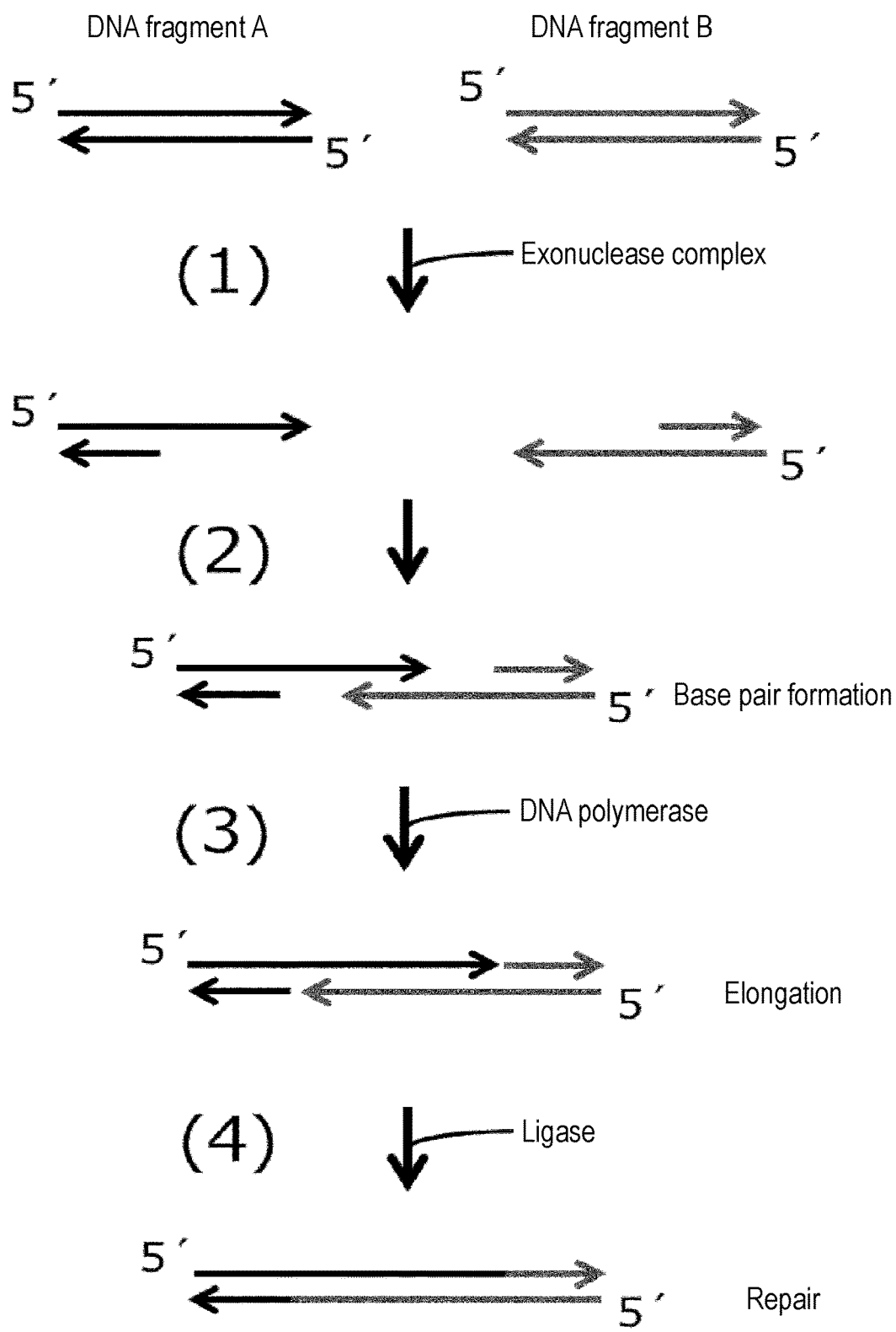
FIG. 5 Mechanism of Gap-repairing. (1) The 5' end of a DNA fragment is scraped by an exonuclease complex, so that the 3' end is exposed. (2) If there is a homologous sequence at the exposed 3' end, a base pair is formed. (3) DNA is elongated by DNA polymerase. (4) DNA is ligated by a ligase.

The yeast parent strain used is auxotrophic and cannot grow on the selective medium. When the designer genome is ligated with the vector in yeast, the parent strain can supply the necessary nutrient source and can grow on the selective medium. In this method, the designer genome is reconstructed by using gap-repair cloning (Gap-repairing). Gap-repairing is thought to be a part of the DNA repair mechanism. FIG. 5 shows an overview of the mechanism of Gap-repairing.

1-4. Extraction of Phage Genome from Yeast
(1) Plant yeast carrying the phage genome in a selective liquid medium and culture it at 30° C. overnight.
(2) Centrifuge 2 mL of the culture solution at 12000 g and room temperature for 2 minutes to recover yeast.
(3) Discard the culture supernatant and extract the phage genome using the Yeastier Genomic DNA Kit (Zymo Research).

1-5. Construction of Plasmid Encoding Virion Constituent Gene and Introduction of Plasmid into *E. coli*

Figure 6:
FIG. 6 Construction of a plasmid cloning the virion constituent gene.
Figure 7:
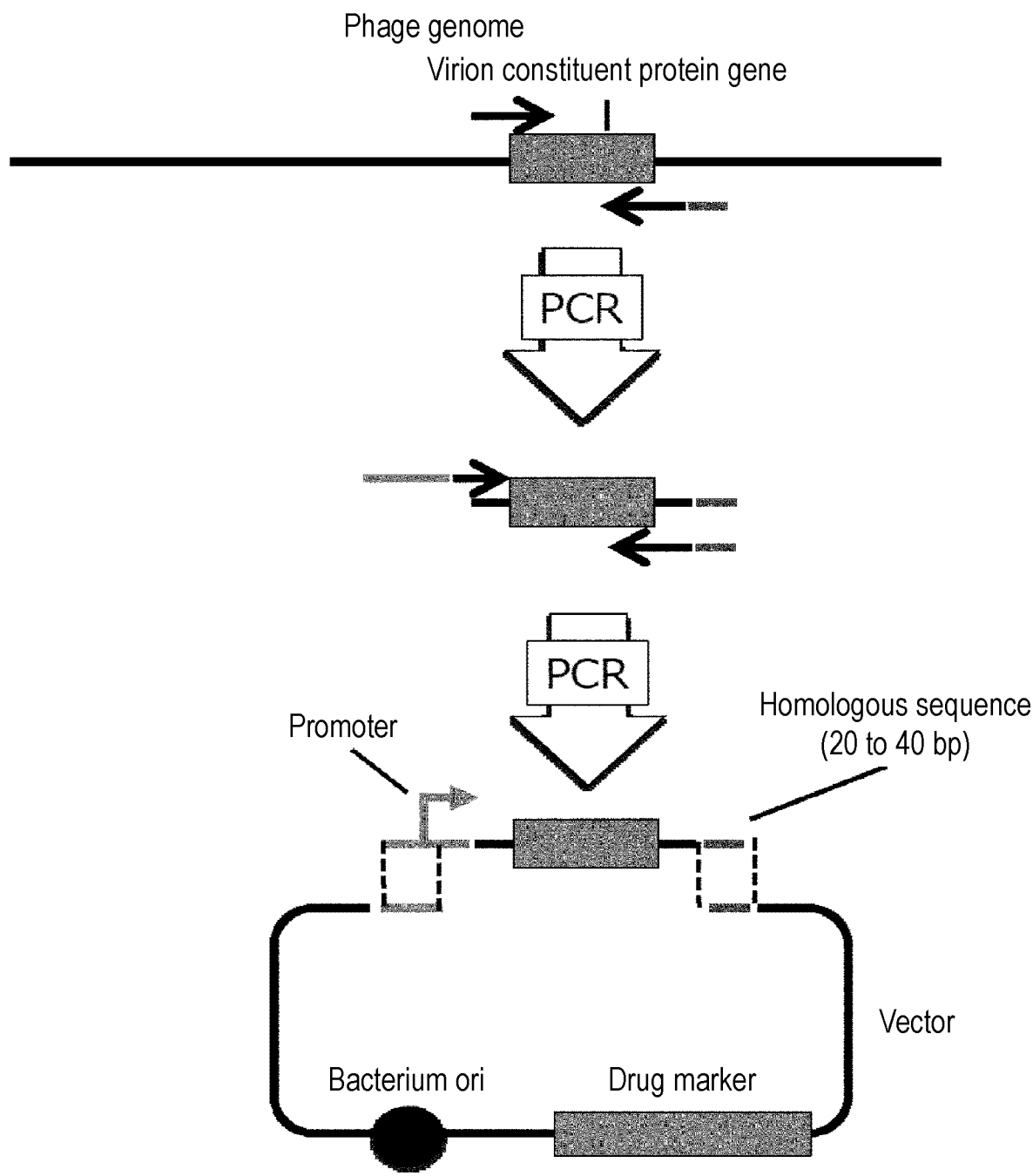
FIG. 7 Construction of a plasmid encoding the virion constituent gene. The virion constituent gene amplified by PCR is ligated to a plasmid vector.

After cloning the virion constituent gene (tail gene or head gene) removed during phage genome reconstruction into the plasmid vector pBR322 (FIG. 6), the plasmid vector was introduced into *E. coli* to prepare *E. coli* carrying the virion constituent gene on the plasmid. If there is no promoter immediately upstream of the virion constituent gene, a promoter sequence is provided on the primer when cloning into the plasmid vector by PCR (FIG. 7). The operation procedures (examples) in the case of the tail genes and the head gene will be described below.

<In Case of Tail Genes (Genes 11, 12 and 17)>
(1) The tail genes, gene 11, gene 12 and gene 17 are each amplified by the first-stage PCR, and each fragment is ligated by the second-stage PCR, and a promoter (TAATACGACTCACTATAGGG: SEQ ID NO: 33) is added. The sequences of primers used for the respective PCRs are shown below. A restriction enzyme site is provided at the end of the DNA fragment.

First-Stage PCR: Tail Gene Amplification
(Fragment 1)
Forward primer sequence: CCACAACGGTTTCCCTCTAGAAATAATTTTGTTTAACTTTAAGAAGGAGATATACCAAT GCGCTCATACGATATGAACG (SEQ ID NO: 34)
Reverse primer sequence: CGTTAGCCATTGGTATATCTCCTTCTTTTAAATACCGGAACTTCTCCG (SEQ ID NO: 35)

(Fragment 2)
Forward primer sequence: CCGGTATTTAAAAGAAGGAGATATAC-CAATGGCTAACGTAATTAAAACCG (SEQ ID NO: 36)
Reverse primer sequence: CCCGCGGATCCT-TACTCGTTCTCCACCATGATTG (SEQ ID NO: 37)

Second-stage PCR: fragment ligation and promoter addition
Forward primer sequence: CCCGGAATTCGAAAT-TAATACGACTCACTATAGGGAGAC-CACAACGGTTTCCCTCTAG (SEQ ID NO: 38)
Reverse primer sequence: CCCGCGGATCCT-TACTCGTTCTCCACCATGATTG (SEQ ID NO: 39)

(2) Treat the DNA fragment (tail gene) and the vector DNA with restriction enzymes for ligation (5 μL, in total).
(3) Mix 45 μL of *E. coli* chemical competent cells with the reaction product and let stand on ice for 30 minutes.
(4) Let stand at 42° C. for 1 minute.
(5) Add 1 mL of an LB liquid medium and let stand at 37° C. for 30 minutes.
(6) Apply to a drug-containing agar medium.

Since *E. coli* carrying the plasmid has acquired a drug (resistance) marker (drug-resistant gene), it can grow on a drug-containing agar medium.

<In Case of Head Gene (Gene 10AB)>
(1) Amplify the head gene (gene10AB) in a form containing a promoter. The sequences of primers used for PCR are shown below. A restriction enzyme site is provided at the end of the DNA fragment.
Forward primer sequence: CCCGCGGATCCTTAT-TGCTCAGCGGTGGCAG (SEQ ID NO: 40)
Reverse primer sequence: CCCGGAAT-TCTAATACGACTCACTATAGGGAGAC (SEQ ID NO: 41)
(2) Treat the DNA fragment (head gene) and the vector DNA with restriction enzymes for ligation (5 μL, in total).
(3) Mix 45 μL of *E. coli* chemical competent cells with the reaction product and let stand on ice for 30 minutes.
(4) Let stand at 42° C. for 1 minute.
(5) Add 1 mL of an LB liquid medium and let stand at 37° C. for 30 minutes.
(6) Apply to a drug-containing agar medium.

Since *E. coli* carrying the plasmid has acquired a drug (resistance) marker (drug-resistant gene), it can grow on a drug-containing agar medium.

1-6. Preparation of Competent Cells for Electroporation
(1) Plant bacteria having a virion constituent gene (tail gene or head gene) in a drug-containing LB liquid medium and culture them at 37° C. overnight.
(2) Add the culture solution to 20 mL of a drug-containing SOB liquid medium to attain 1/100 times the amount, and culture it at 37° C. until OD600=0.4.
(3) Centrifuge the culture solution at 800 g and 4° C. for 5 minutes.
(4) Discard the culture supernatant and suspend the culture in 10 mL of cold 10% glycerol.
(5) Centrifuge the suspension at 800 g and 4° C. for 5 minutes.
(6) Discard the supernatant and suspend the culture in 10 mL of cold 10% glycerol.
(7) Centrifuge the suspension at 800 g and 4° C. for 5 minutes.
(8) Discard the supernatant and suspend the culture in about 70 μL of cold 10% glycerol. This is used as competent cells for electroporation.

1-7. Activation of Virion Constituent Gene-Deleted Phage
(1) Mix 2 μL of the extracted virion constituent gene-deleted phage genome (tail gene-deleted phage genome or head gene-deleted phage genome) with 20 μL of competent cells for electroporation, and put them in a cuvette.
(2) Electroporation (2.5 kV, 10 μF, 600Ω).
(3) Add 500 μL of an LB liquid medium to the cuvette and recover.
(4) Mix the mixed solution with a soft agar medium and layer it on LB agar medium.
(5) Let stand at 37° C. until plaque (lytic spots) are formed.

1-8. Confirmation of Virion Constituent Gene-Deleted Phage
(1) Poke the plaque with a toothpick or tip and suspend it in 100 μL of a phage buffer.
(2) Mix bacteria expressing or not expressing the virion constituent gene (tail gene or head gene) with soft agar medium and layer it on an LB agar medium. Add dropwise 2.5 μL of the phage buffer in which plaque is suspended thereto, and dry.
(3) Let stand at 37° C. until plaque is formed.

Confirm that plaque is formed in the bacteria expressing the virion constituent gene (tail gene or head gene), and that no plaque is formed in the bacteria not expressing the gene.

1-9. Recovery of Virion Constituent Gene-Deleted Phage
(1) Plant bacteria expressing the virion constituent gene (tail gene or head gene) in a drug-containing LB liquid medium and culture them at 37° C. overnight.
(2) Add 1/100 amount of the bacterial culture solution to 50 mL of a drug-containing LB liquid medium.
(3) Culture it at 37° C. until OD600=0.4.
(4) Add the phage buffer in which phage is suspended and culture it until the bacteria are completely lysed.
(5) Add 1 mL of chloroform (completely kill the remaining bacteria).
(6) Centrifuge the solution at 12000 g and 4° C. for 5 minutes. This creates a layer of lytic solution and chloroform.
(7) The lytic solution is filtered and sterilized with a 0.22-μm filter to obtain a phage solution.

1-10. Killing Assay
(1) Plant bacteria in LB liquid medium and culture them at 37° C. overnight.
(2) Prepare 5 bottles of an LB liquid medium to which the bacterial culture solution is added so as to attain $1 \times 10^6$ cfu/ml, and add thereto an LB liquid medium or the phage solution so as to attain MOI=1, MOI=10, MOI=100, MOI=1000.
(3) Culture it at 37° C. and sample 1 mL every 2 hours.
(4) Centrifuge the sample at 5000 g and 4° C. for 5 minutes.
(5) Discard the culture supernatant and suspend the culture in 1 mL of PBS.
(6) Centrifuge the suspension at 5000 g and 4° C. for 5 minutes.
(7) Discard the supernatant and suspend the culture in 1 mL of PBS. This is used as a stock solution.
(8) Dilute the stock solution 10 times from $10^{-1}$ to $10^{-7}$ with PBS, add 2.5 μL each on LB agar medium, and dry.
(9) Let stand overnight at 37° C.
(10) Count the number of viable cells (number of colonies).

2. Preparation and Confirmation of Transduction Nanoparticle

Figure 3:
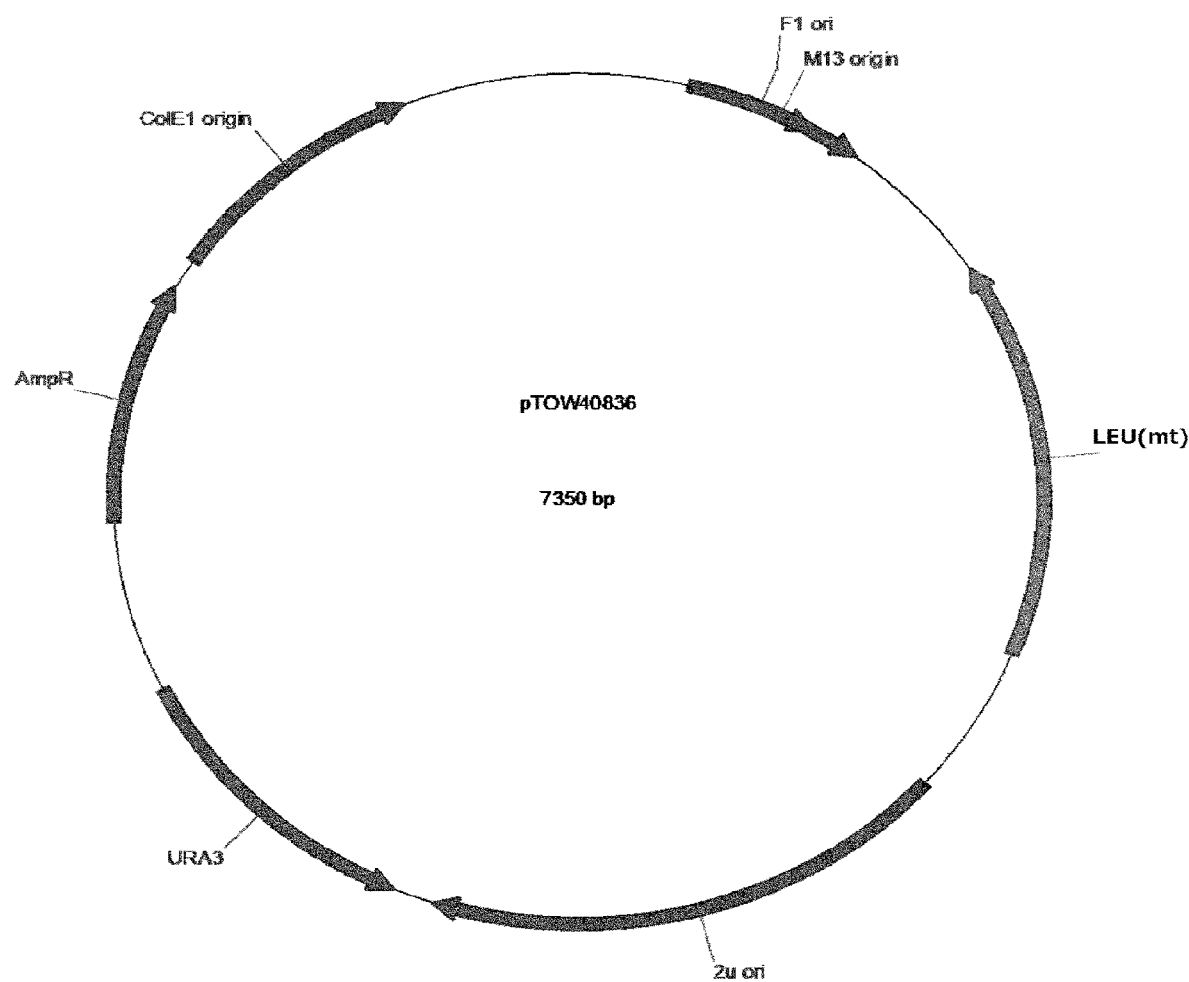
FIG. 3 Construction of a vector ligated with a virion constituent gene-deleted phage genome.

The design and reconstruction of the designer phage genomes, the preparation of yeast competent cells, the transformation of yeast, and the extraction of the phage genome from yeast are performed in the same manner as in the case of the virion gene-deleted phage. Phage DNA contains a sequence required to be packed in the phage head, called packaging (hereinafter, PAC) site. Primers are designed so as to eliminate that sequence and amplified by PCR while the vector pTOW40836 is amplified (FIG. 3). In this study, the phage genome excluding the PAC site was divided into four parts, and the four segments (referred to as fragment I, fragment II, fragment III, and fragment IV in order from the 5' end side to the 3' end side) were amplified by PCR. The sequences of the primers used to amplify the respective fragments are as follows.

(Fragment I)
  Forward primer sequence: CTTGAAGACGAAAGGGCCTCGTGATACGCCGTC-CATCCTAAAGCCAACACCTAAAGCC (SEQ ID NO: 42)
  Reverse primer sequence: ATTACGCGATGACAGTAGACAACCTTTCCG (SEQ ID NO: 43)
(Fragment II)
  Forward primer sequence: TGCAGCAATACCGGAAAGGTTGTCTACTGT (SEQ ID NO: 44)
  NO: 45)
  Reverse primer sequence: ATATGTCTCCTCATAGATGTGCCTATGTGG (SEQ ID (Fragment III) NO: 46)
  Forward primer sequence: ACTTGTGACTCCACATAGGCACATCTATGA (SEQ ID
  Reverse primer sequence: GAATAACCTGAGGGTCAATACCCTGCTTGT (SEQ ID NO: 47)
(Fragment IV)
  Forward primer sequence: GACATGATGGACAAGCAGGGTATTGACCCT (SEQ ID NO: 48)
  Reverse primer sequence: CATAATAGAAACGACACGAAATTACAAAATTGCATAAATCACCACTCAATGAAAGAC G (SEQ ID NO: 49)

The sequences of the primers used to amplify the vector fragment are as follows.
  Forward primer sequence: ATTTTGTAATTTCGTGTCGTTTCTATTATG (SEQ ID NO: 20)
  Reverse primer sequence: GGCGTATCACGAGGCCCTTTCGTCTTCAAG (SEQ ID NO: 21)

Figure 8:
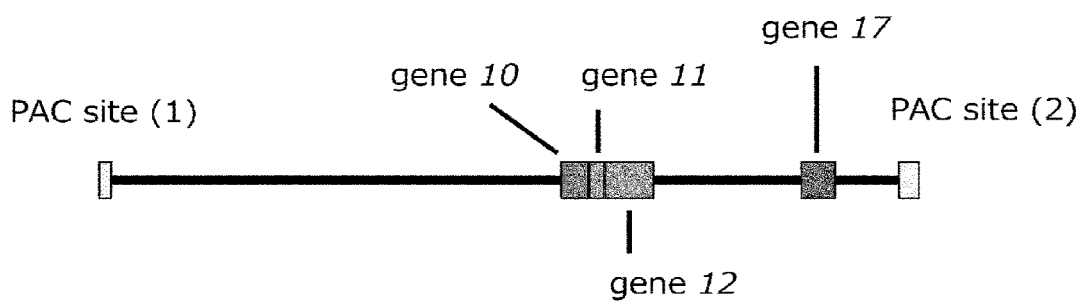
FIG. 8 Design and reconstruction of a PAC site-deleted phage genome. The phage genome and vector are amplified by PCR using primers designed so that the PAC site is not amplified, and ligated in yeast.
Figure 8:
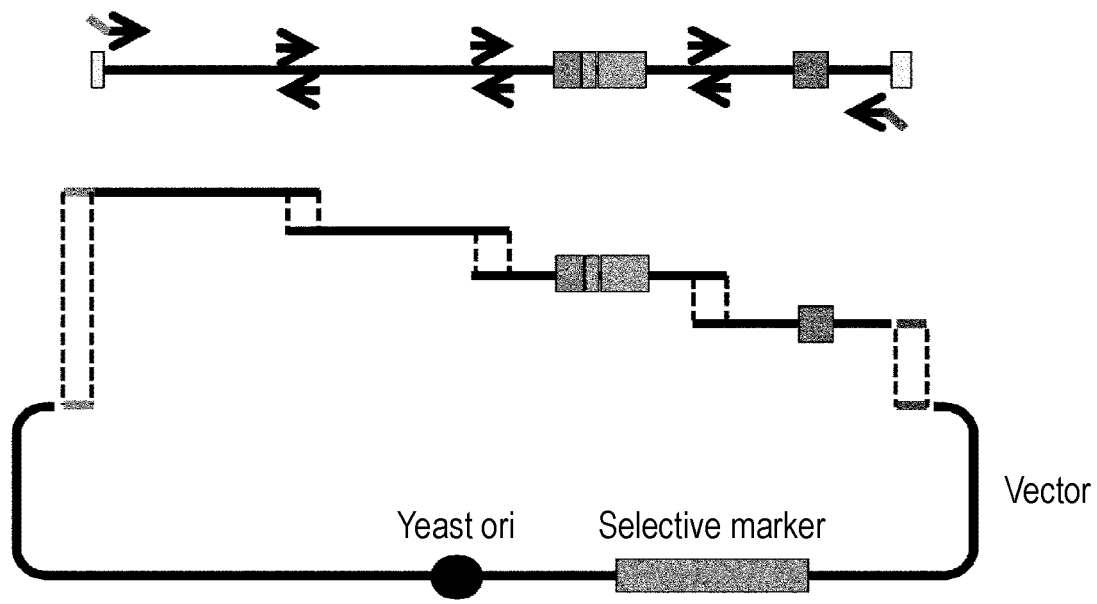

A DNA sample used for yeast transformation was prepared by diluting a mixture of phage genomic DNA fragments (fragments I to IV) and a vector fragment with ultrapure water to 50 μL in a measuring cylinder. Yeast is transformed to reconstitute the phage genome (SEQ ID NO: 50) lacking the PAC site (FIG. 8).

The plasmid having the PAC site is constructed by the same method as for the plasmid having the virion constituent gene (the PAC site site is cloned into the plasmid pBR322 instead of the virion constituent gene).

Competitive cells for electroporation of bacteria carrying a plasmid having a PAC site are prepared by the same method as for virion gene-deleted phage, and transduction nanoparticle are activated by the following method.
  (1) Mix 2 μL of the extracted PAC site-deleted phage genome and 20 μL of competent cells for electroporation and put them in a cuvette.
  (2) Electroporation (2.5 kV, 10 μF, 600Ω).
  (3) After electroporation, add 1 mL of an LB liquid medium to the cuvette containing the PAC site-deleted phage genome and the competent cells, and let stand at 37° C. for 2 hours.
  (4) Add 100 μL of chloroform to the mixed solution and mix them by tapping.
  (5) Centrifuge the solution at 12000 g and 4° C. for 5 minutes. This creates a layer of mixture and chloroform.
  (6) Filter and sterilize the mixed solution through a 0.22 μm filter.
  (7) Use the recovered solution as a transduction nanoparticle solution.
  (8) Mix the transduction nanoparticle solution and the bacterial culture solution and let stand at 37° C. for 30 minutes.
  (9) Apply to a drug-containing agar medium.

Since the plasmid has a drug marker, the bacterium infected with the transduction nanoparticle is injected with the plasmid to acquire the drug resistance. The bacterium injected with the plasmid (=in which the transduction nanoparticle functions) can grow on the drug-containing agar medium.

<Development of Tail Gene-Deleted Phage>
1. Method

Figure 9:
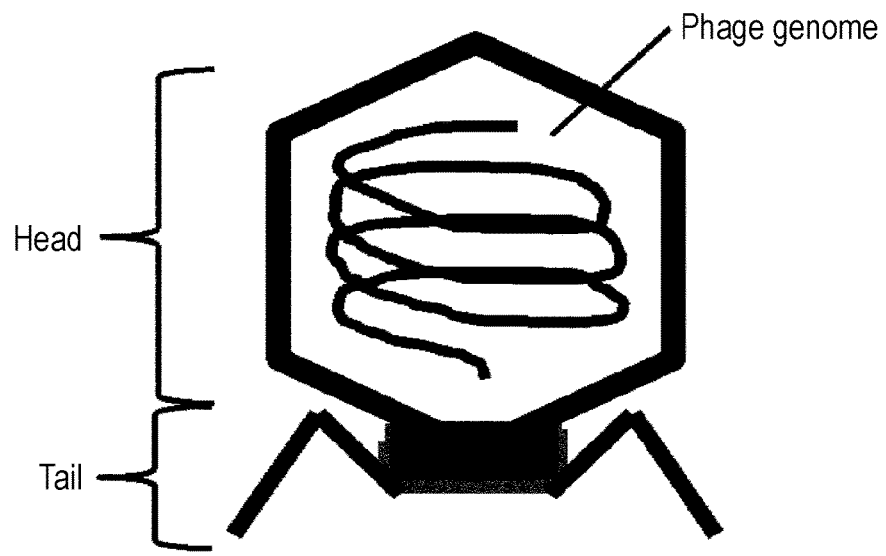
FIG. 9 Structure of a phage.
Figure 10:
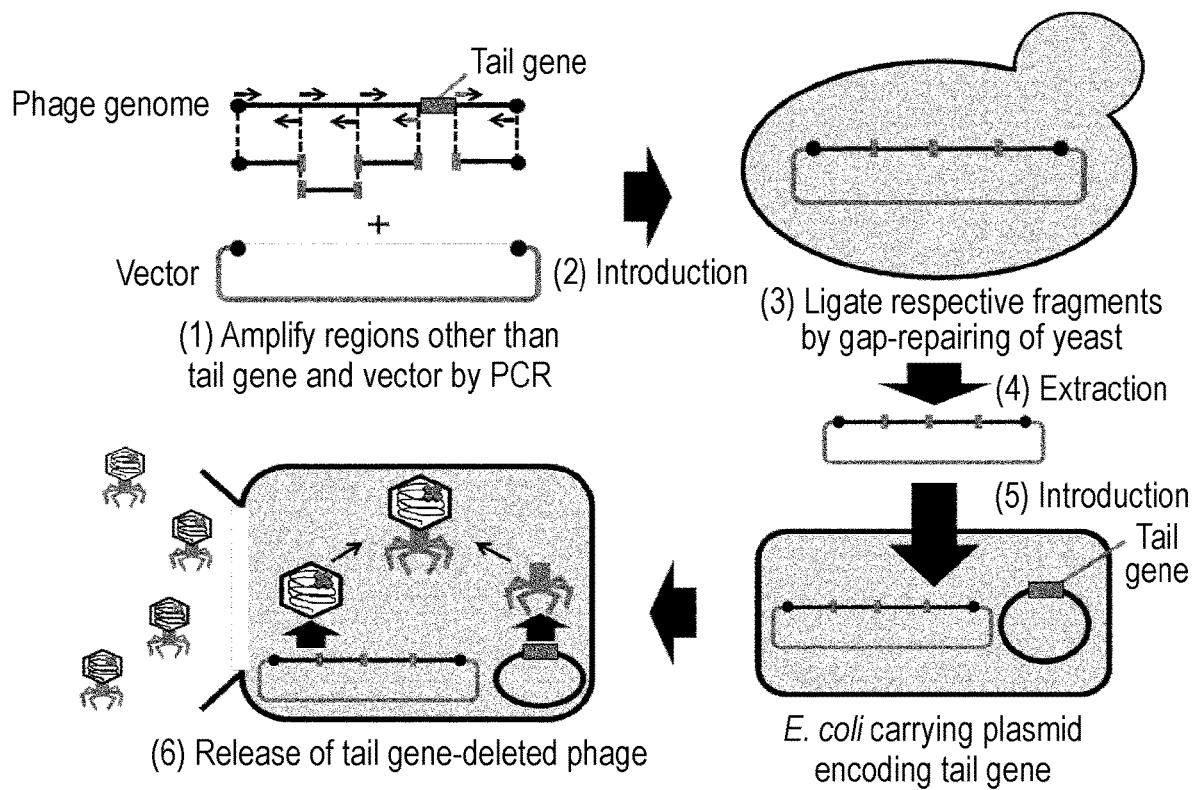
FIG. 10 Flow of producing tail gene-deleted phages.

The phage consists of a head in which the genome is stored and a tail required for adhesion to the bacterium (FIG. 9). It adheres to the bacterial surface via feet (tail fibers) at the tip of the tail. Regions other than the tail gene of the phage genome and vectors having homologous sequences to both ends of the phage genome were amplified by PCR, and these fragments were ligated in yeast to construct an artificial phage genome (SEQ ID NO: 7) (FIG. 10). In this experiment, an artificial phage genome was constructed using gap-repair cloning, but the Gibson Assembly also succeeded in constructing an artificial phage genome.

The phage genome was extracted from yeast, and the phage genome was introduced into $E.\ coli$ carrying the plasmid encoding the tail gene (FIG. 10). Phage constituent proteins other than the tail are expressed from the phage genome and the tail is expressed from the plasmid, and phages that "having a tail as a phenotype and having no tail as a genotype" are formed in $E.\ coli$. Eventually, $E.\ coli$ is lysed and phages lacking the tail gene are released (FIG. 10). Progeny phages produced from this phage do not have a tail and therefore cannot re-infect the host bacterium.

2. Results (Bactericidal Effect of Tail Gene-Deleted Phage)

Figure 11:
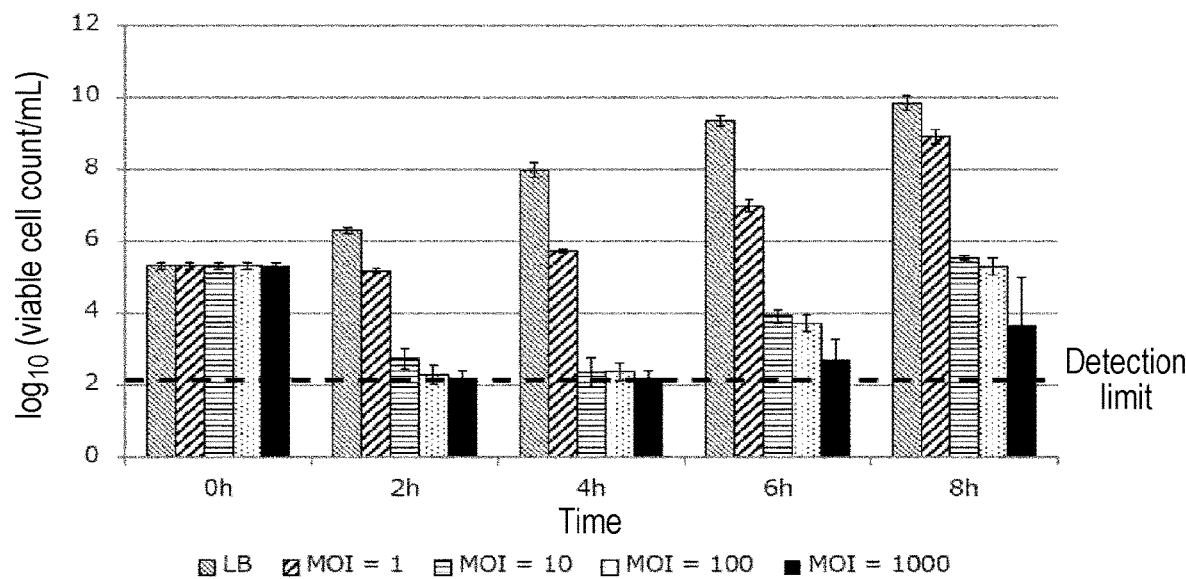
FIG. 11 Bactericidal effect of the tail gene-deleted phages. *E. coli* was infected with a predetermined number of the tail gene-deleted phages, and the viable cell count was measured over time. LB: Medium only (no tail gene-deleted phage), MOI=1: Infect *E. coli* with as many tail gene-deleted phages as *E. coli*, MOI=10: Infect *E. coli* with 10 times as many tail gene-deleted phages as *E. coli*, MOI=100: Infect *E. coli* with 100 times as many tail gene-deleted phages as *E. coli*, and MOI=1000: Infect *E. coli* with 1000 times as many tail gene-deleted phages as *E. coli*.
Figure 12:
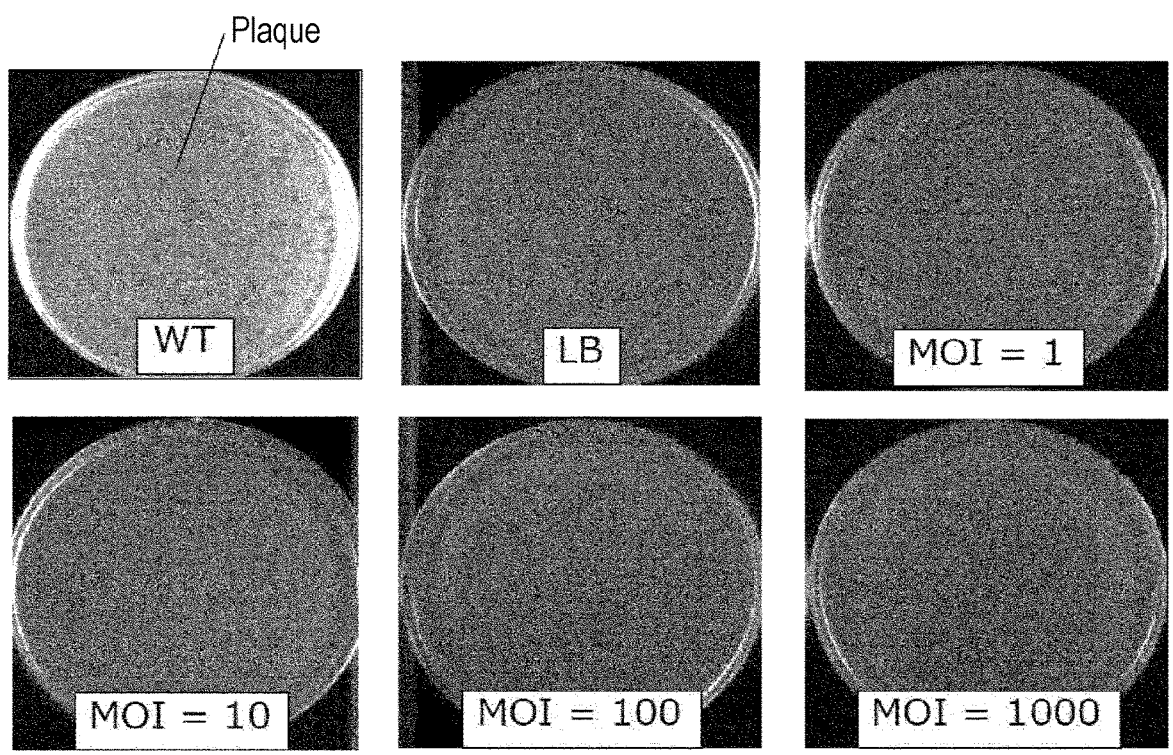
FIG. 12 Results of plaque formation assay. A sample after killing assay was continuously cultured to confirm whether plaque was formed. WT: Wild-type T7 phage (positive control); LB: Medium only (negative control); MOI=1: Mixture of *E. coli* with a culture supernatant after further 24-hour culture of a sample obtained by infecting *E. coli* with as many tail gene-deleted phages as *E. coli*; MOI=10: Mixture of *E. coli* with a culture supernatant after further 24-hour culture of a sample obtained by infecting *E. coli* with 10 times as many tail gene-deleted phages as *E. coli*; MOI=100: Mixture of *E. coli* with a culture supernatant after further 24-hour culture of a sample obtained by infecting *E. coli* with 100 times as many tail gene-deleted phages as *E. coli*; and MOI=1000: Mixture of *E. coli* with a culture supernatant after further 24-hour culture of a sample obtained by infecting *E. coli* with 1000 times as many tail gene-deleted phages as *E. coli*.

$E.\ coli$ was prepared to attain $1\times10^6$ per mL, and tail gene-deleted phages 1, 10, 100, or 1000 times (MOI=1, 10, 100, or 1000) as many as $E.\ coli$ were added, and the viable cell count of $E.\ coli$ was measured over time (Killing assay). Growth inhibition was observed by adding as many tail gene-deleted phages as $E.\ coli$ (MOI=1), and the viable cell count of $E.\ coli$ was significantly reduced at MOI=10, 100, and 1000 (FIG. 11). In addition, each sample was continuously cultured as it was, and it was confirmed whether new phages were produced from the samples (plaque formation assay). When $E.\ coli$ and phage are mixed with soft agar and layered on the agar medium and the culture is continued, transparent spots called lytic spots (plaques) are formed as shown in "WT" in FIG. 12. This occurs when the phage infects and lyses the bacterium. No lytic spots were observed even when each culture solution was mixed with $E.\ coli$. This strongly suggests the possibility that phage which can re-infect might not have been produced at least in this experimental system. A head gene-deleted phage was also prepared (see above for the preparation method), and similar experimental results were obtained.

<Development of Transduction Nanoparticle>

1. Method

Figure 13:
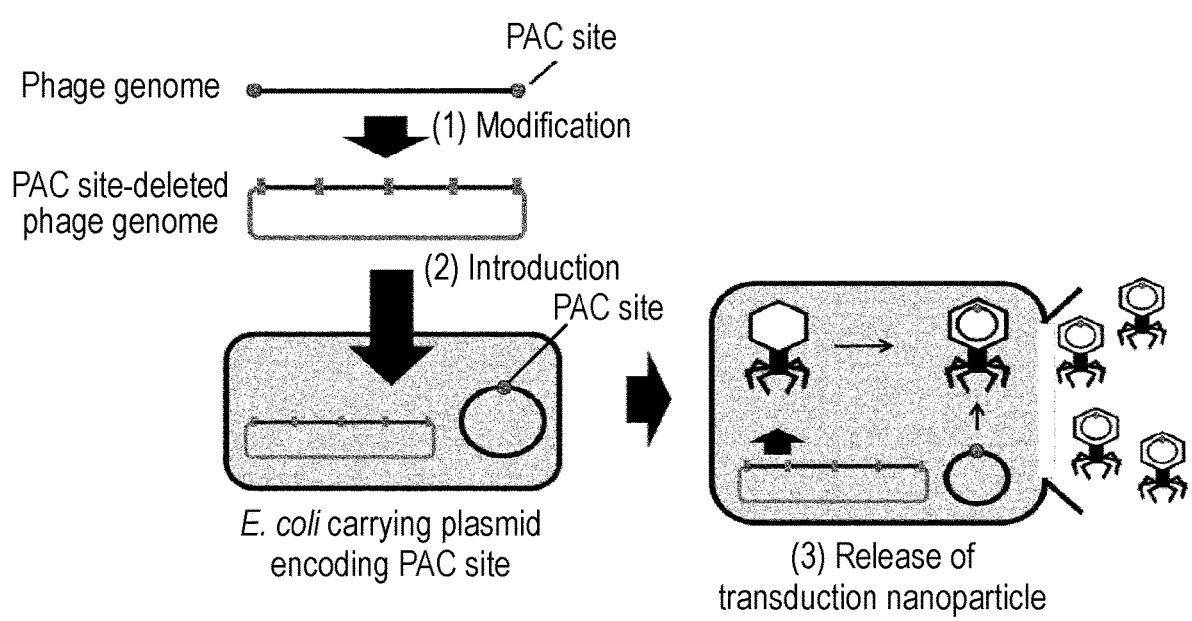
FIG. 13 Flow of producing transduction nanoparticles.

The storage of the phage genome in the head is referred to as packaging. There is a sequence called a packaging (PAC) site on the phage genome, and, when this is recognized, the phage genome is stored in the head. A transduction nanoparticle that can package an arbitrary plasmid in place of the phage genome was developed by deleting the PAC site on the phage genome and providing the PAC site on the plasmid. As in the above-mentioned method for developing the tail gene-deleted phage, a phage genome (SEQ ID NO: 50) in which the PAC site was deleted was constructed by amplifying regions other than the PAC site and a vector by PCR and ligating them in yeast. Next, a phage genome lacking the PAC site was extracted from yeast and introduced into E. coli carrying a plasmid having the PAC site. No PAC site is present in the phage genome during phage formation, and thus the phage genome is not packaged. Instead, a plasmid with the PAC site is packaged (FIG. 13). Even if this nanoparticle infects the bacterium, it merely introduces the plasmid and has no bactericidal effect. In addition, since it does not have a phage genome, no progeny phage is formed.

2. Results (Transduction Efficiency of Transduction Nanoparticle)

Figure 14:
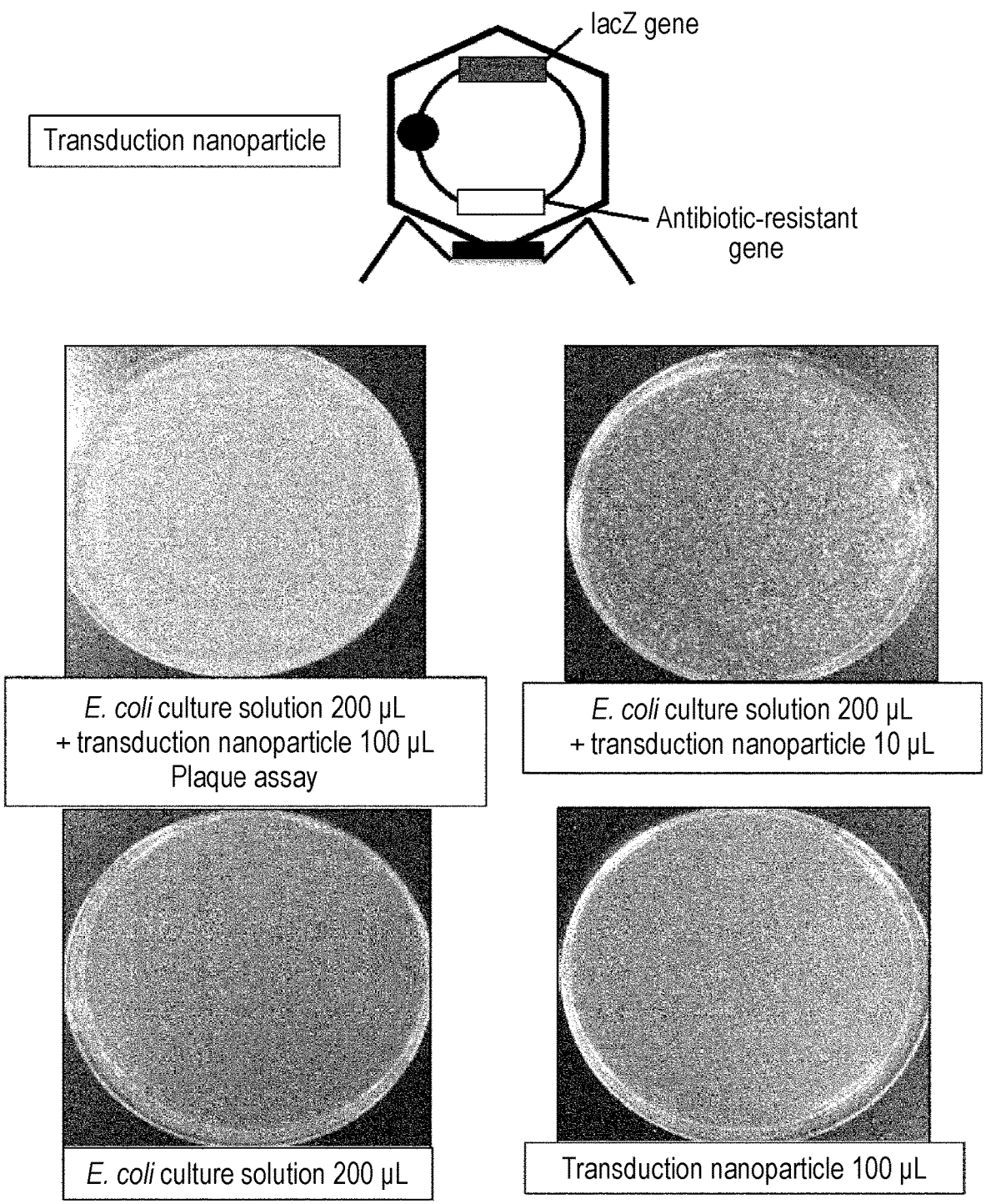
FIG. 14 Transduction efficiency of the transduction nanoparticles. *E. coli* was infected with a transduction nanoparticle (upper part) in which a PAC site-carrying plasmid in which an antibiotic-resistant gene and a lacZ gene encoding β-galactosidase were inserted was packaged, and colony formation was observed (upper right plate). Comparison was made with *E. coli* alone (lower left plate) and the transduction nanoparticles only (lower right plate). The upper left plate indicates the result of the plaque formation assay.

The antibiotic-resistant gene and the lacZ gene encoding β-galactosidase were inserted into the PAC site-carrying plasmid, which was packaged in the transduction nanoparticle. β-galactosidase is an enzyme that hydrolyzes β-galactoside to produce galactose. When bacteria carrying this enzyme are allowed to grow on a medium containing a reagent called X-gal, the colonies turn blue. As a result of mixing 10 μL of transduction nanoparticle with E. coli having no lacZ gene and applying the mixture on an agar medium containing an antibiotics and X-gal (FIG. 14), blue colonies were observed from a plate applied with E. coli infected with transduction nanoparticle (upper right plate). Even though only E. coli (lower left plate) or 100 μL of transduction nanoparticle (lower right plate) was applied on the agar medium, no colonies were formed, so blue E. coli found on the plate applied with E. coli infected with the transduction nanoparticle is considered to have acquired the antibiotic gene and the lacZ gene by the transduction nanoparticle. A plaque formation assay was performed considering the possibility of inclusion of wild-type phages, but no plaque was formed (upper left plate). When calculated from the number of colonies, the transduction efficiency was about $4.2 \times 10^5$/L.

CONCLUSION

Two types of "host bacterium-specific nanoparticles" have been developed. One functions as a nanoparticle having a bactericidal ability, and the other functions as a nanoparticle having a transduction ability. In principle, this technique should be applicable to all phages. It is expected to be used in phage therapy and bacterial flora editing, and as a tool for bacteria for which no genetic method has been established. The nanoparticle can infect the host bacterium only once, and 100% biological containment has been successfully attained in at the laboratory level.

<Verification of Biological Containment>

The biological containment of the virion constituent gene-deleted phage (head gene-deleted phage and tail gene-deleted phage) was verified.

1. Plaque Formation Assay

Figure 15:
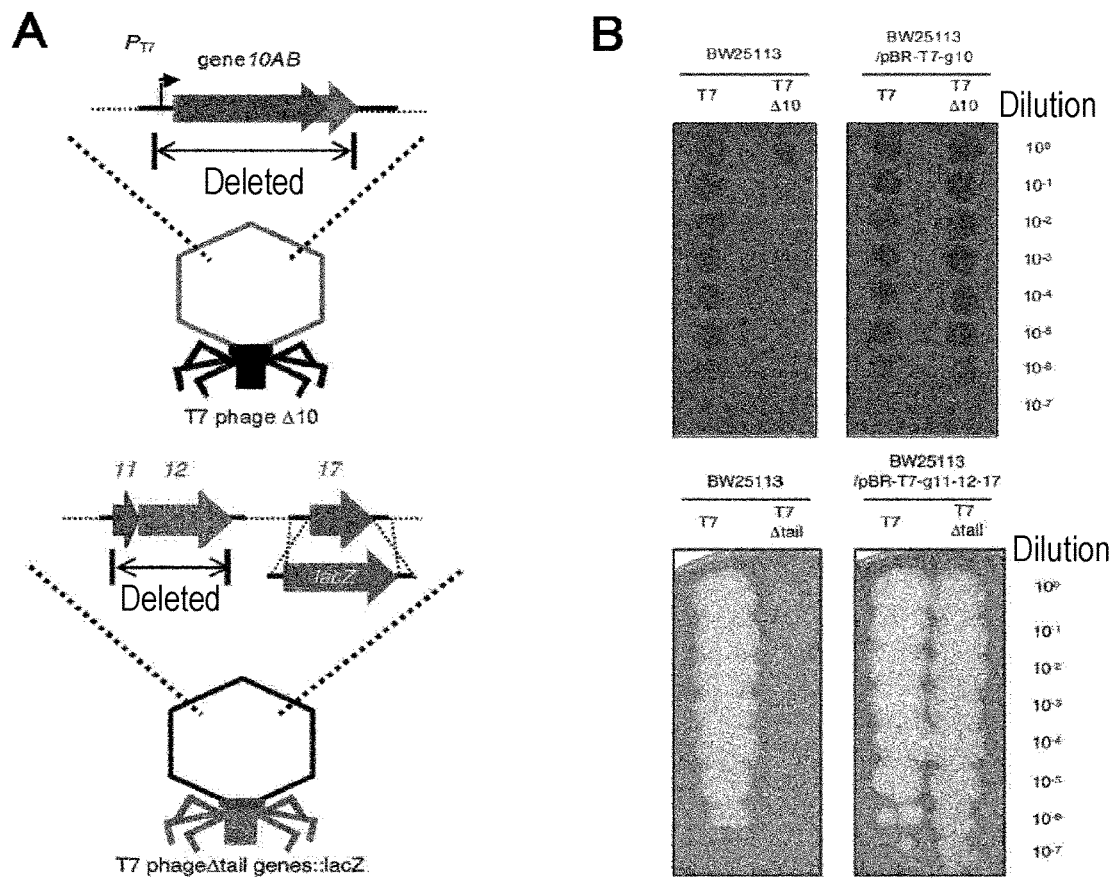
FIG. 15 Verification of biological containment by the plaque formation assay. A solution of the head gene-deleted phage (upper part in A) or tail gene-deleted phage (lower part in A) was added to *E. coli* to observe plaque formation (B).

After E. coli strain BW25113 was applied to an agar medium, a phage solution (containing a head gene-deleted phage (upper part in FIG. 15A) or a tail gene-deleted phage (lower part in FIG. 15A)) was added thereto and cultured. A phage solution of wild-type phage was used for control. In contrast to wild-type phage (T7 column on the left side of FIG. 15B (BW25113)), no plaque formation was observed in the case of the head gene-deleted phage (T7Δ10 column on the left side of FIG. 15B (BW25113)) and the tail gene-deleted phage (T7Δtail column on the left side of FIG. 15B (BW25113)), and containment was successful. When the head gene is expressed in the same E. coli strain (T7Δ10 column on the right side of FIG. 15B (BW25113/pBR-T7-g10)) or when the tail gene is expressed (T7Δtail column on the right side of FIG. 15B (BW25113/pBR-T7-g11-12-17), containment phages (head gene-deleted phage and tail gene-deleted phage) can also produce progeny phages and form plaques.

2. Lysis-from-without Phenomenon

Figure 16:
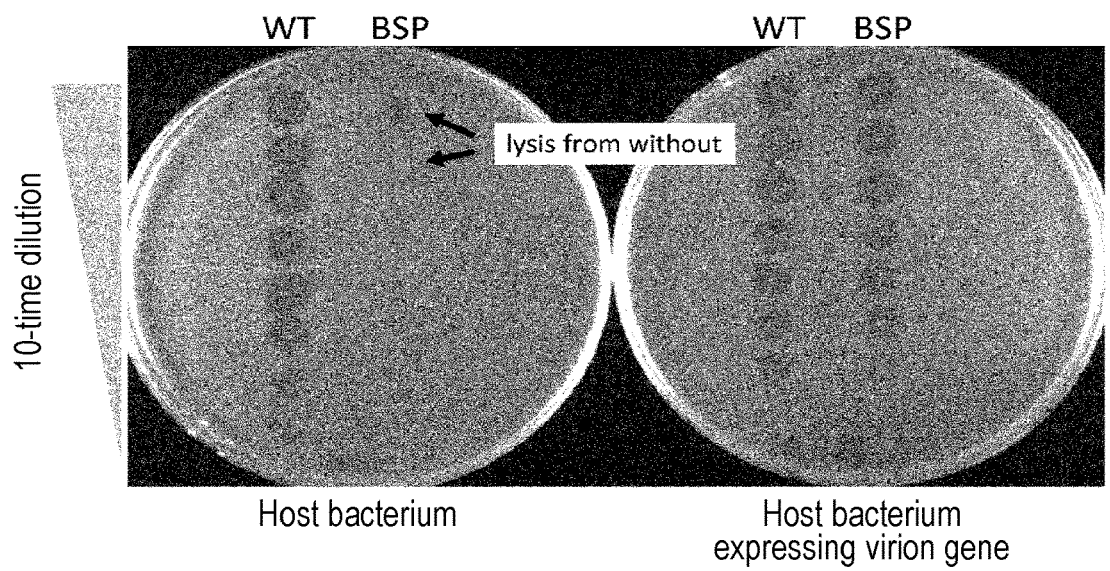
FIG. 16 Confirmation of a lysis-from-without phenomenon. Addition of the head gene-deleted phage caused the lysis-from-without phenomenon and no plaque formation (BSP on the left plate). When the head gene was expressed in *E. coli*, plaque was formed (BSP on the right plate). BSP: Bio-contained Synthetic Phage (host-specific nanoparticle)

Lysis-from-without is a phenomenon in which the host bacterium is killed regardless of the presence or absence of progeny phage production when a large excess amount of phage infects the host bacterium, and is characterized in that no individual plaque is observed. After E. coli strain BW25113 was applied to an agar medium, a phage solution (head gene-deleted phage) was added and cultured. A phage solution of wild-type phage was used for control. The head gene-deleted phage cannot produce progeny phage through containment and cannot form plaques (BSP column on the left plate in FIG. 16). When the head gene is expressed, the head gene-deleted phage can also produce progeny phage and form plaques (BSP column on the right plate in FIG. 16).

3. Bactericidal Actions of Head Gene-Deleted Phage and Tail Gene-Deleted Phage

Figure 17:
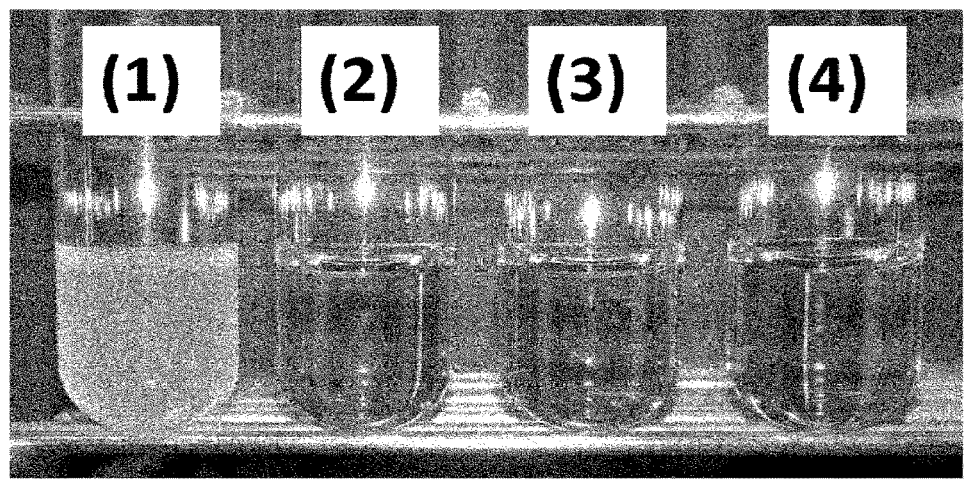
FIG. 17 Confirmation of bactericidal action. (1) *E. coli* BW25113, (2) BW25113+phage T7 (MOI=10), (3) BW25113+BSPAhead (head gene-deleted phage) (MOI=10), and (4) BW25113+BSPAtail (tail gene-deleted phage)) (MOI=10).

After addition of the head gene-deleted phage or the tail gene-deleted phage to the solution of E. coli BW25113, the phages were cultured for 6 hours to evaluate the bactericidal action. As is the case with the bactericidal wild-type phage (T7) ((2) in FIG. 17), the head gene-deleted phage and the tail gene-deleted phage showed bactericidal activity ((3) and (4) in FIG. 17).

4. Proliferating Property

Figure 18:
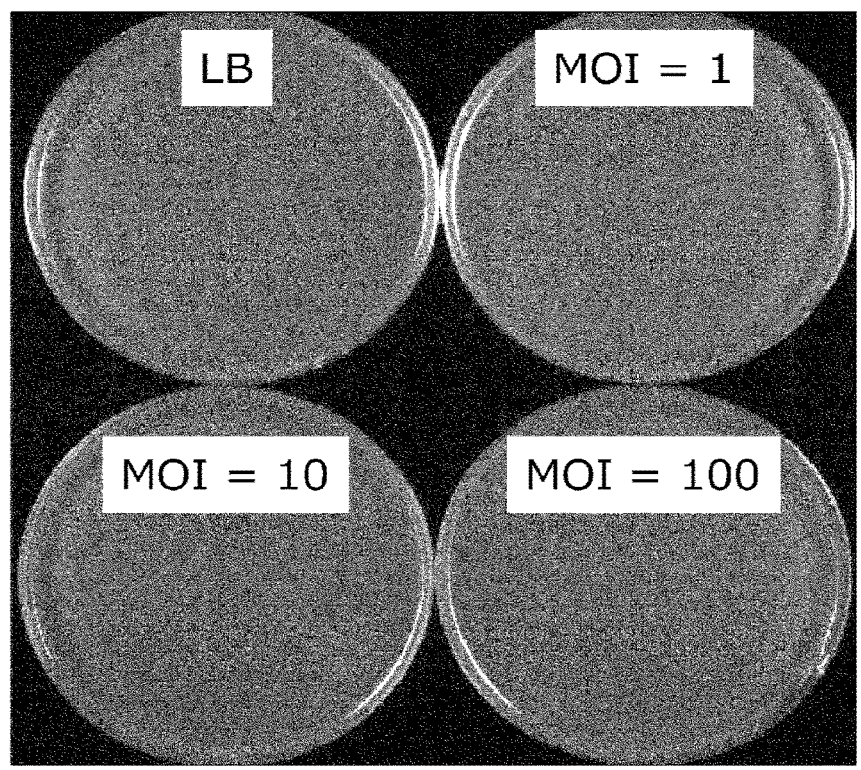
FIG. 18 Verification of biological containment by the plaque formation assay. Upper left (LB): Plate containing only the host bacterium, Upper right: Plate with the head gene-deleted phage added at MOI=1, Lower left: Plate with the head gene-deleted phage added at MOI=10, and Lower right: Plate with the head gene-deleted phage added at MOI=100.

After application of E. coli strain BW25113 to an agar medium, a phage solution (head gene-deleted phage) was added at each concentration. After the culture was continued for 24 hours, the presence or absence of plaque formation was observed. No plaque was observed even at MOI=100 (a large excess amount of phage added) (FIG. 18). That is, the containment-treated phage (head gene-deleted phage) has not acquired proliferating property and can infect only once (i.e., successful biological containment).

5. Verification of Effectiveness In Vivo

Figure 19:
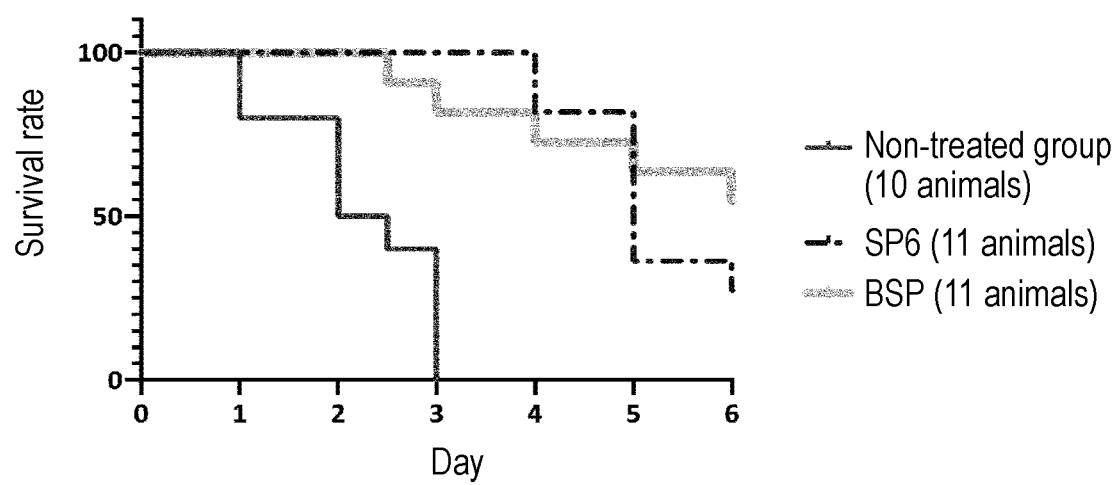
FIG. 19 Verification of effectiveness in vivo. Survival rates of *Salmonella* LT2-inoculated mice were compared among the non-treated group, which received neither SP6 nor head gene-deleted phage, the SP6-administered group (SP6), and the head gene-deleted phage-administered group (BSP).

After inoculation of mice BJ6 with Salmonella LT2 at 0.8 to $1.4 \times 10^5$ cfu, SP6 or head gene-deleted phage was administered thereto at 2.5 to $5.0 \times 10^7$ pfu, and the survival rates were compared and evaluated. Mice not administered with either SP6 or head gene-deleted phage were used as a control (non-treated group). The survival rate of the head gene-deleted phage-administered group (BSP) was significantly higher than that of the non-treated group, surpassing that of the SP6-administered group (SP6) (FIG. 19). On the other hand, no phage was detected in the blood and spleen of the mice in the head gene-deleted phage-administered group, and 100% biological containment was successfully attained.

INDUSTRIAL APPLICABILITY

The recombinant phage provided by the present invention is deprived of proliferative capacity and can infect only once. Since high safety is ensured by virtue of this feature, the recombinant phage is suitable for various uses including clinical applications. Among the recombinant phages of the present invention, those in which the phage genome (however, a part of the virion constituent genes are deleted) is stored in the head and which show a bactericidal ability are expected to be particularly used for phage therapy. On the other hand, recombinant phages, in which a specific plasmid is stored in the head instead of the phage genome, can be expected to be used/applied, as gene introduction tools, in a wide range of applications including modification of drug sensitivity of drug-resistant bacteria, improvement of the productivity of industrial enzyme-producing bacteria, manufacture of foods/beverages (particularly fermented foods and fermented beverages) and pharmaceutical or industrial products (chemical products, etc.), production of bioenergy (e.g., bioethanol), and improvement of bacterial capacity to be used in bioremediation (processing capacity, manufacturing/production capacity, etc.).

The present invention is not limited to the above embodiments and examples of the invention at all. Various modifications are also included in the present invention as long as they can be easily conceived by those skilled in the art without departing from the scope of the claims. The contents of the papers, published patent gazettes, patent gazettes, etc. clarified therein shall be incorporated by reference in their entirety.

SEQUENCE LISTING FREE TEXT

SEQ ID NO: 7: Description of artificial sequence: tail gene-deleted phage genome
SEQ ID NO: 8: Description of artificial sequence: Forward primer
SEQ ID NO: 9: Description of artificial sequence: reverse primer
SEQ ID NO: 10: Description of artificial sequence: Forward primer
SEQ ID NO: 11: Description of artificial sequence: reverse primer
SEQ ID NO: 12: Description of artificial sequence: forward primer
SEQ ID NO: 13: Description of artificial sequence: reverse primer
SEQ ID NO: 14: Description of artificial sequence: forward primer
SEQ ID NO: 15: Description of artificial sequence: reverse primer
SEQ ID NO: 16: Description of artificial sequence: forward primer
SEQ ID NO: 17: Description of artificial sequence: reverse primer
SEQ ID NO: 18: Description of artificial sequence: forward primer
SEQ ID NO: 19: Description of artificial sequence: reverse primer
SEQ ID NO: 20: Description of artificial sequence: forward primer
SEQ ID NO: 21: Description of artificial sequence: reverse primer
SEQ ID NO: 22: Description of artificial sequence: head gene-deleted phage genome
SEQ ID NO: 23: Description of artificial sequence: forward primer
SEQ ID NO: 24: Description of artificial sequence: reverse primer
SEQ ID NO: 25: Description of artificial sequence: forward primer
SEQ ID NO: 26: Description of artificial sequence: reverse primer
SEQ ID NO: 27: Description of artificial sequence: forward primer
SEQ ID NO: 28: Description of artificial sequence: reverse primer
SEQ ID NO: 29: Description of artificial sequence: forward primer
SEQ ID NO: 30: Description of artificial sequence: reverse primer
SEQ ID NO: 31: Description of artificial sequence: forward primer
SEQ ID NO: 32: Description of artificial sequence: reverse primer
SEQ ID NO: 33: Description of artificial sequence: promoter
SEQ ID NO: 34: Description of artificial sequence: forward primer
SEQ ID NO: 35: Description of artificial sequence: reverse primer
SEQ ID NO: 36: Description of artificial sequence: forward primer
SEQ ID NO: 37: Description of artificial sequence: reverse primer
SEQ ID NO: 38: Description of artificial sequence: forward primer
SEQ ID NO: 39: Description of artificial sequence: reverse primer
SEQ ID NO: 40: Description of artificial sequence: reverse primer
SEQ ID NO: 41 Artificial Sequence Description: Forward Primer
SEQ ID NO: 42: Description of artificial sequence: reverse primer
SEQ ID NO: 43: Description of artificial sequence: forward primer
SEQ ID NO: 44: Description of artificial sequence: reverse primer
SEQ ID NO: 45: Description of artificial sequence: forward primer
SEQ ID NO: 46: Description of artificial sequence: forward primer
SEQ ID NO: 47: Description of artificial sequence: reverse primer
SEQ ID NO: 48: Description of artificial sequence: forward primer
SEQ ID NO: 49: Description of artificial sequence: reverse primer

The invention claimed is:

1. A nanoparticle, consisting of a recombinant bacteriophage that includes a head and a tail, and has an ability to infect but no ability to reinfect a host bacterium, the head having stored therein a bacteriophage genome in which a part of a virion constituent gene is deleted, and
wherein the part of the virion constituent gene which is deleted is a tail gene.

2. The host bacterium-specific nanoparticle according to claim 1, wherein the bacteriophage genome is a genome of T7 phage.

3. An antibacterial agent comprising the nanoparticle according to claim 1 as an active ingredient.

4. A composition comprising the antibacterial agent according to claim 3.

5. The composition according to claim 4, which is a pharmaceutical, disinfectant, cleaning agent, or oral composition against bacterial infections.

6. A nanoparticle, consisting of a recombinant bacteriophage that comprises a head and a tail, and has an ability to infect but no ability to re-infect a host bacterium,
the head having stored therein a plasmid comprising a bacteriophage genome in which a part of a virion constituent gene is deleted having a packaging site and encoding the target gene, wherein the part of the virion constituent gene which is deleted is a tail gene.

7. The nanoparticle according to claim 6, wherein the bacteriophage genome is a genome of T7 phage.

8. The nanoparticle according to claim 6, wherein the target gene is one or more genes selected from the group consisting of a marker gene, a reporter gene, an enzyme gene, a gene for genome editing, a gene encoding an antibacterial peptide, an antibacterial gene, and a group of genes constituting a synthetic gene circuit.

9. A composition for transduction, comprising the nanoparticle according to claim 6 as an active ingredient.

10. A recombinant bacteriophage comprising a head and a tail, and having an ability to infect but no ability to re-infect a host bacterium,
    the head having stored therein a bacteriophage genome in which a part of a virion constituent gene is deleted.

11. The recombinant bacteriophage according to claim 10, wherein the recombinant bacteriophage is a virulent phage.

12. A pharmaceutical composition comprising the recombinant bacteriophage according to claim 10 and an excipient.

* * * * *